United States Patent [19]

Ippolito et al.

[11] Patent Number: 5,580,858
[45] Date of Patent: Dec. 3, 1996

[54] IMMUNOSUPPRESSIVE AND TOLEROGENIC MODIFIED LEWIS$^x$ COMPOUNDS

[75] Inventors: Robert M. Ippolito; Wasimul Haque; Cong Jiang; H. Rizk Hanna; Andre P. Venot; Pandurang V. Nikrad; Mohammed A. Kashem; Richard H. Smith, all of Edmonton, Canada

[73] Assignee: Alberta Research Council, Canada

[21] Appl. No.: 337,461

[22] Filed: Nov. 4, 1994

Related U.S. Application Data

[63] Continuation of Ser. No. 895,930, Jun. 9, 1992, abandoned, which is a continuation-in-part of Ser. No. 889,017, May 26, 1992, abandoned, which is a continuation-in-part of Ser. No. 714,161, Jun. 10, 1991.

[51] Int. Cl.$^6$ .......................... A61K 31/715; C07H 5/04; C07H 5/10
[52] U.S. Cl. ....................... 514/25; 514/61; 536/17.5; 536/18.5; 536/53; 536/54; 536/55; 536/117; 536/118; 536/119
[58] Field of Search ................... 536/17.5, 18.5, 536/53, 54, 55, 117, 118, 119; 514/54, 61

[56] References Cited

U.S. PATENT DOCUMENTS

| | | | |
|---|---|---|---|
| 4,563,445 | 1/1986 | Feizi et al. | 514/25 |
| 4,612,132 | 9/1986 | Wollenberg et al. | 252/51.5 A |
| 5,079,235 | 1/1992 | Purifoy et al. | 514/49 |
| 5,079,353 | 1/1992 | Ratcliffe et al. | 536/53 |
| 5,143,712 | 9/1992 | Brandley et al. | 424/1.73 |
| 5,211,936 | 5/1993 | Brandley et al. | 424/1.73 |
| 5,211,937 | 5/1993 | Brandley et al. | 424/1.73 |

FOREIGN PATENT DOCUMENTS

| | | | |
|---|---|---|---|
| WO92/19633 | 11/1992 | WIPO | C07H 15/04 |
| WO94/06442 | 3/1994 | WIPO . | |

OTHER PUBLICATIONS

Aruffo, et al., *Cell*, 67:34–44 (1991).
Capon, et al., *Eur. J. Biochem.*, 183:139–152 (1989).
Chardrasekaren, et al., *Abstracts of the 11th International Symposium of Glycoconjugates*, 8:3 (1991).
Tanphaichitr, et al., *Abstracts of the 11th International Symposium of Glycoconjugates*, 11.18 (1991).
Yuen, et al., *Biochemistry*, 31:9126–9131 (1992).
Roberts et al; Arch. Biochem. Biophys. 267(2): 405–415 (1988).
Ginsburg et al; Biochimie 70:1651–1659 (1988).
Green et al; Biochem. Biophys. Res. Commun. 188(1): 244–251 (Oct. 15, 1992).
El Khadem; *Carbohydrate Chemistry* pp. 104–181 (1988).
Stults et al; Meth Enzymol. 179:167, 170–175; 200–213 (1989).
Mc Omie; *Protective Groups in Organic Chemistry* (1973) pp. 109–118.

Shin et al; Carb. Res. 76:165–176 (1979).
Tsutsumi et al; Carb. Res. 88:61–75 (1981).
Mehmet et al; Eur. J. Biochem. 157:385–391 (1986).
Derappe et al; Carb. Res. 150:273–284 (1986).
Ali, et al., "Thio and epidithio derivatives of methyl β-lactoside", *Carbohydrate Res.*, 216:271–287 (1991).
Jain et al., "Synthesis of the sodium salts of methyl 2-O-α-L-fucopyranosyl-α-L-fucopyranoside 3–and 4–sulfate", *Carbohydrate Res.*, 208: 51–58 (1990).
Srivastava et al., "Synthesis of Phosphorylated Pentasaccharides Found on Asparagine–Linked Carbohydrate Chains of Lysosomal Enzymes", *J. Org. Chem.*, 52: 2869–2875 (1987).
Chandrasekaran, et al., Journal of Biological Chemistry, 267:23506–23814 (1992).
Ichikawa, et al., J. Am. Chem. Soc., 113:6300–6302 (1991).
Kato, et al., The Journal of Biological Chemistry, 264:3364–3371 (1989).
Lasky, Science, 258:964–969 (1992).
Abbas et al., "Sialic Acids 1988" Proc. Japanese–German Symp. Berlin, pp. 20–21 (1988).
Amvam–Zollo et al., "Type XIV Polysaccharide: Synthesis of A Repeating Branched Tetrasaccharide with Dioxa–Type Spacer–Arms" Carbohydr. Res. 150:199–212 (1986).
Bernotas et al., "Easy assembly of ligands for glycosidase affinity chromatography" Biochem. J., 270:539–540 (1990).
Chernyak et al., "A New Type of Carbohydrate–Containing Synthetic Antigen: Synthesis of Carbohydrate–Containing Poly–Acrylamide Copolymers Having the Specificity of 0:3 and 0:4 Factors of *Salmonella* Carbohydr. Res. 128:269–282 (1984).
Dahmen et al., "2–Bromethyl glycosides: applications in the synthesis of spacer–arm glycosides" Carbohydr. Res. 118:292–301 (1983).
Dumas et al., "Enzymatic Synthesis of Sialyl Le$^x$ and Derivatives Based on a Recombinant Fucosyltransferase" Bioorg. Med. Letters, 1:425–428 (1991).
Ekborg et al., "Synthesis of Three Disaccharides for the Preparation of Immunogens Bearing Immunodeterminants Known to Occur on Glycoproteins" Carbohydr. Res. 110:55–67 (1982).
Eppenberger–Castori et al., "Purification of the N–Acetylgulcosaminide α(1–¾) Fucosyltransferase of Human Milk" Glycocon. J. 6:101–114 (1989).
Fernandez–Santana et al., "Glycosides of Monoallyl Diethylene Glycol. A New Type of Spacer Group for Synthetic Oligosaccharides" J. Carbohydr. Chem. 8:531–537 (1989).
Fügedi et al., "Thioglycosides as Glycosylating Agents in Oligosaccharide Synthesis" Glycoconj. J. 4:97–108 (1987).

(List continued on next page.)

Primary Examiner—Douglas W. Robinson
Assistant Examiner—Kathleen Kahler Fonda
Attorney, Agent, or Firm—Burns, Doane, Swecker & Mathis

[57] ABSTRACT

Disclosed are novel Lewis$^x$ and Lewis$^a$ analogues, pharmaceutical compositions containing such analogues, methods for their preparation and methods for their use.

10 Claims, 21 Drawing Sheets

OTHER PUBLICATIONS

Gokhale et al., "Chemical synthesis of GDP–fucose analogs and their utilization by the Lewis α–(1→4) fucosyltransferase" Can. J. Chem. 68:1063–1071 (1990).

Greig et al., "The Preparation of Phenyl 2–Amino–2–deoxy–β–D–glucopyranoside and Some 2–Acylamino–derivatives thereof" J. Chem. Soc., p. 879 (1961).

Inazu et al., "New Synthetic Methods and Reagents for Complex Carbohydrates. II. Synthesis of 2–Acylamino2–deoxy–D–glucopyranose Derivatives by Dimethylphosphinothioic Mixed Anhydride Method" Bull. Soc. Chim., Jap., 611:4467 (1988).

Kameyama et al., "Total synthesis of sialyl Lewis X" Carbohydr. Res., 209:$C_1$–$C_4$ (1991).

Kukowska–Latallo et al., "A cloned human CDNA determines expression of a mouse stage–specific embryonic antigen and the Lewis blood group α(1,3/1,4)fucosyltransferase" Genes and Development, 4:1288–1303 (1990).

Larsen et al., "PADGEM–Dependent Adhesion of Platelets to Monocytes and Neutrophils is Mediated by a Lineage–Specific Carbohydrate, LNF III (CD15)" Cell, 63:467–474 (1990).

Lee et al., "Synthesis of 3–(2–Aminoethylthio)Propyl Glycosides" Carbohydr. Res., 37:193 et seq. (1974).

Lemieux et al., "Synthesis of derivatives of N–acetyl–D–lactosamine from D–lactal hexaacetate" Can. J. Chem. 60:63–67 (1982).

Lemieux et al., "The Properties of a 'Synthetic' Antigen Related to the Human Blood–Group Lewis a" J. Amer. Chem. Soc., 97:4076–4083 (1975).

Lowe et al., "ELAM–1–Dependent Cell Adhesion to Vascular Endothelium Determined by a Transfected Human Fucosyltransferase CDNA" In Cell, 63:475–485 (1990).

Nicolaou et al., "Total Synthesis of the Tumor–Associated $Le^x$ Family of Glycosphingolipids" JACS, 112:3693–3695 (1990).

Nilsson et al., "Synthesis of a Dimeric Lewis X Hexasaccharide Derivative Corresponding to a Tumor–Associated Glycolipid" Carbohydr. Res., 183:71–82. (1988).

Nunez, et al., "The synthesis and Characterization of α–and β–L–fucopyranosyl phosphates and GDP fucose" Can. J. Chem., 59:2086–2095 (1981).

Okamoto et al., "Glycosidation of Sialic Acid" Tetrahedron, vol. 46, No. 17, pp. 5835–5837 (1990).

Palcic et al., "Enzymic Synthesis of Oligosaccharides Terminating in the Tumor–Associated Sialyl–Lewis–a Determinant" Carbohydr. Res., 190:1–11 (1989).

Paulsen et al., "Synthese Von Oligosaccharid–Determinanten Mit Admid–Spacer Vom Typ Des T–Antigens" Carbohydr. Res. 104:195–219 (1982).

Paulsen, "Advances in Selective Chemical Syntheses of Complex Oligosaccharides" Agnew. Chem. Int. Ed. Eng., 21:155–173 (1982).

Petitou et al., "Synthesis of Heparin Fragments" Carbohydr. Res., 147:221–236 (1986).

Phillips et al., "ELAM–1 Mediates Cell Adhesion by Recognition of a Carbohydrate Ligand, Sialyl–$Le^x$" In Science, 250:1130–1132 (1990).

Piekarska–Bartowzewicz et al., "A new method for the synthesis of ureido sugars" Carbohydr. Res., 203:302–307 (1990).

Prieels et al., Co–purification of the Lewis Blood Group N–Acetylglucosaminide α1→4 Fucosyltransferase and an N–Acetylglucosaminide α1→3 Fucosyltransferase from Human Milk" J. Biol. Chem., 256:10456–10463 (1981).

Rana et al., "Synthesis of Phenyl 2–Acetamido–2–Deoxy–3–O–α–L Fucopyra–Nosyl–β–D–Glucopyranoside and Related Compounds" Carbohydr. Res. 91:149–157 (1981).

Reuter, Sialic Acids in "Cell Biology Monographs" Schauer, Editor 10: 263–305 (1982).

Reuter et al., "Suggestions on the Nomenclature of Sialic Acids" Glycoconjugate J. 5:133–135 (1988).

Sato et al., "Total Synthesis of a Stage Specific Embryonic Antigen–1 (SSEA–1) A Glycoheptaosyl Ceramide $V^3FucnLc_6Cer^1$)"Tet. Letters, 29:4759–4761 (1988).

Schmidt, et al., "Stereospecific Synthesis of α–and β–L–Fucopyranosyl Phosphates and of GDP–Fucose via Trichloracetimidate" Liebigs Ann. Chem., 121–124 (1991).

Schmidt, "New Methods for the Synthesis of Glycosides and Oilgosaccharides–Are There Alternatives to the Koenigs–Knorr Method?"Agnew. Chem. Int. Ed. Eng., 25:212–235 (1986).

Sleytr et al., "Structural and chemical characterization of S–layers of selected strains of *Bacillus stearothermophilus* and *Desulfotomaculum nigrificans*", Arch. Microbiol., 146:19–24 (1986).

Smith et al., "Cyclophosphamide and dimethyl dioctadecyl ammonium bromide immunopotentaiate the delayed–type hypersensitivity response to inactivated enveloped viruses", Immunnology, 58:245–250 (1986).

Trumtel et al., "The Synthesis of 2'–Deoxy–β–Disaccharides" Carbohydr. Res., 191:29–52 (1989).

Veeneman, et al., "An approach towards the synthesis of 1,2–*trans* glycosyl phosphates *via* iodonium ion assisted activation of thioglycosides" Tetrahedron Lett., 32:6175–6178 (1991).

Walz et al., "Recognition by ELAM–1 of the Sialyl–$Le^x$ Determinant on Myeloid and Tumor Cells" Science 250:1132 et seq. (1990).

Weinstein et al., "Sialylation of Glycoprotein Oligosaccharides N–linked to Asparagine", J. Biol. Chem., 257:13845–13853 (1982).

Ziola et al., "Adherent Cells Suppress Measles and Herpes Simplex I Virus–Induced Blastogenesis of Multiple Sclerosis Lymphocytes" J. Neuroimmunol., 7:315–330 (1985).

IMMUNOSUPPRESSIVE AND TOLEROGENIC MODIFIED LEWIS$^x$ COMPOUNDS

This application is a continuation of application Ser. No. 07/895,930, filed Jun. 9, 1992, now abandoned; which is a continuation in part of application Ser. No. 07/889,017, filed May 26, 1992, now abandoned; which is a continuation-in-part of application Ser. No. 07/714,161, filed Jun. 10, 1991, currently pending. Each of these applications is incorporated herein by reference in its entirety.

BACKGROUND OF THE INVENTION

1. Field of the Invention

The present invention is directed to novel Lewis$^x$ and Lewis$^a$ analogues, pharmaceutical compositions containing such analogues, methods for their preparation and methods for their use.

2. References

The following references are cited in this application as superscript numbers at the relevant portion of the application:

1. Horowitz, the Glycoconjugates, Vols. I–V, Pigman, Editor, New York Academic Press (1977, 1978, 1982, 1983).
2. Ippolito et al., U.S. patent application Ser. No. 07/714,161, filed Jun. 10, 1991 for "Immunosuppresive and Tolerogenic Oligosaccharide Glycosides".
3. Sialic Acids in "Cell Biology Monographs" Schauer, Editor, Vol. 10 (1982).
4. Lowe et al., Cell, 63:475–485 (1990).
5. Phillips et al., Science, 250:1130–1132 (1990).
6. Walz et al., Science 250:1132 et seq. (1990).
7. Larsen et al., Cell, 63:467–474 (1990).
8. Ratcliffe et al., U.S. Pat. No. 5,079,353, issued Jan. 7, 1992, for "Sialic Acid Glycosides, Antigens, Immunoadsorbents, and Methods for their Preparation".
9. Ratcliffe et al., U.S. Pat. No. 5,296,594, filed Nov. 30, 1988, for "Sialic Acid Glycosides, Antigens, Immunoadsorbents, and Methods for their Preparation".
10. Venot et al., U.S. Pat. No. 5,352,670, "Methods for the Enzymatic Synthesis of Alpha-sialylated Oligosaccharide Glycosides", filed Oct. 2, 1991.
11. Weinstein et al., J. Biol. Chem., 257:13845–13853 (1982).
12. Reuter et al., Glycoconjugate J. 5:133–135 (1988).
13. Palcic et al., Carbohydr. Res., 190:1–11 (1989).
14. Prieels et al., J. Biol. Chem., 256:10456–10463 (1981).
15. Eppenberger-Castori et al., Glycoconj. J. 6:101–114 (1989).
16. Gokhale et al., Can. J. Chem., 68:1063–1071 (1990).
17. Jiang et al., U.S. patent application Ser. No. 07/848,223 filed Mar. 9, 1992, for "Chemical Synthesis of GDP-Fucose".
18. Ekberg et al., Carbohydr. Res. 110:55–67 (1982).
19. Dahmen et al., Carbohydr. Res. 118:292–301 (1983).
20. Rana et al., Carbohydr. Res. 91:149–157 (1981).
21. Amvam-Zollo et al., Carbohydr. Res. 150:199–212 (1986).
22. Paulsen et al., Carbohydr. Res. 104:195–219 (1982).
23. Chernyak et al., Carbohydr. Res. 128:269–282 (1984).
24. Fernandez-Santana et al., J. Carbohydr. Chem. 8:531–537 (1989).
25. Lee et al., Carbohydr. Res., 37:193 et seq. (1974).
26. Norberg et al., Carbohydr. Res. 183:71 et seq. (1988).
27. Matta et al., Carbohydro. Res. 208:51–58 (1980).
28. Chandrasekaren et al., Abstracts of the 11th International Symposium on Glycoconjugates, Jun. 30, 1991.
29. Kukowska-Latallo et al., Genes and Development, 4:1288–1303 (1990).
30. Dumas et al., Bioorg. Med. Letters, 1:425–428 (1991).
31. Okamoto et al., Tetrahedron, Vol. 46, No. 17, pp. 5835–5837 (1990).
32. Abbas et al., Proc. Japanese-German Symp. Berlin, pp. 20–21 (1988).
33. Paulsen, Agnew. Chem. Int. Ed. Eng., 21:155–173 (1982).
34. Schmidt, Agnew. Chem. Int. Ed. Eng., 25:212–235 (1986).
35. Fügedi et al., Glycoconj. J., 4:97–108 (1987).
36. Kameyama et al., Carbohydr. Res., 209:$C_1$–$C_4$ (1991).
37. Inazu et al., Bull. Soc. Chim., Jap., 611:4467 (1988).
38. Bernotas et al., Biochem. J., 270:539–540 (1990).
39. Wollenberg et al., U.S. Pat. No. 4,612,132, for Issued Sep. 21, 1986 for "Modified Succinimides".
40. Greig et al., J. Chem. Soc., p. 879 (1961).
41. Piekarska-Bartowzewicz et al., Carbohydr. Res., 203:302–307 (1990).
42. Petitou et al., Carbohydr. Res., 147:221–236 (1986).
43. Trumtez et al., Carbohydr. Res., 191:29–52 (1989).
44. Lemieux et al., J. Amer. Chem. Soc., 97: 4076–4083 (1975).
45. Ogawa et al., Tet. Letters, 29:4759–4761 (1988).
46. Lemieux et al., Can. J. Chem. 60:63–67 (1982).
47. Nicolaou et al., JACS, 112:3693–3695 (1990).
48. Hindsgaul et al., J. Org. Chem., 52:2869–2875 (1975)
49. Richardson et al., Carbohydr. Res. 216:271–287 (1991)
50. Smith et al., Immunology, 58:245 (1986).
51. Sleytr et al., Arch. Microbiol., 146:19 (1986).
52. Ziola et al., J. Neuroimmunol., 7:315–330 (1985).
53. Gokhale et al., Can. J. Chem., 68:1063–1071 (1990)
54. Schmidt, et al., Liebigs Ann. Chem., 121–124 (1991)
55. Nunez, et al., Can. J. Chem., 59:2086–2095 (1981)
56. Veeneman, et al., Tetrahedron Lett., 32:6175–6178 (1991)

All publications and patent applications mentioned in this specification are indicative of the level of skill of those skilled in the art to which this invention pertains. All publications and patent applications are herein incorporated by reference in their entirety to the same extent as if each individual publication or patent application was specifically and individually indicated to be incorporated by reference in its entirety.

STATE OF THE ART

Carbohydrates and/or oligosaccharides are present on a variety of natural and pathological glycoconjugates[1]. Of particular interest are carbohydrates and oligosaccharides containing sialyl and/or fucosyl residues3. Such sialyl and/or fucosyl carbohydrates and oligosaccharides are present in a number of products which have been implicated in a wide range of biological phenomena based, in part, on the concept of recognition signals carried by the carbohydrate structures and by their binding to specific ligands.

Specifically, a number of sialylated and sialylated/fucosylated oligosaccharide glycosides have been proposed as mediators of cell adhesion in that they are ligands for selectins (or LEC-CAM's)[4,5,6,7]. Sialylated, fucosylated, and sialylated and fucosylated oligosaccharide structures relating to blood group determinants, including Lewis$^x$, Lewis$^a$, sialyl Lewis$^x$ and sialyl Lewis$^a$, have also been shown by Ippolito et al.[2] to possess in vivo immunomodulating and tolerogenic properties in mammals including anti-inflammatory immunomodulating properties. In this regard, the DTH anti-inflammatory immunomodulating properties of Lewis[x] and sialyl Lewis[x] reported by Ippolito et al.[2] demonstrate that the presence of the sialyl residue on sialyl Lewis[x] results in enhanced anti-inflammatory activity as compared to Lewis[x].

Contrarily, sialyl Lewis[x], and sialyl Lewis[a] and related compounds are difficult to chemically synthesize in high yield with anomeric specificity for the α(2→3) linkage of Neu5Ac to galactose. Known chemical methodologies include a multistep synthesis which first generates a blocked αNeu5Ac(2→3)Gal disaccharide having a suitable leaving group at the reducing sugar terminus of the galactose[8,9]. This disaccharide is then reacted with a suitably protected GlcNAc-OR saccharide glycoside and then a suitably protected L-fucose derivative which, after deprotection, provides for the sialyl Lewis[x] glycoside [αNeu5Ac(2→3)βGal(1→4)[αFuc(1→3)]-βGlcNAc-OR] or the sialyl Lewis[a] glycoside [i.e., αNeu5Ac(2→3)βGal(1→3)[αFuc(1→4)]βGlcNAc-OR] where R is an aglycon of at least one carbon atom.

Additionally, sialyl Lewis[x], sialyl Lewis[a] and related compounds can also be synthesized via chemical/enzymatic synthesis 2,9,10. In general, the βGal(1→4)βGlcNAc-OR, the derivatized βGal(1→4)βGlcNAc-OR, the βGal(1→3)βGlcNAc-OR, or the derivatized βGal(1→3)βGlcNAc-OR backbone is first synthesized chemically and then the sialic acid residue (e.g., Neu5Ac) is attached to the galactose to form the αNeu5Ac(2→3)βGal(1→3)βGlcNAc-OR or the αNeu5Ac(2→3)βGal(1→4)βGlcNAc-OR structures by use of a compatible sialyltransferase and the fucose residue is then attached to the 4-hydroxyl position of the N-acetylglucosamine residue by use of a compatible fucosyltransferase.

However, the enzymatic synthesis of sialyl Lewis[x] and related compounds is restricted by the availability of compatible sialyltransferases. For example, the βGal(1→¾)βGlcNAc α(2→3)sialyltransferase disclosed in the art for sialylating the βGal(1→4)βGlcNAc backbone is currently recovered from rat livers[11].

In any event, the inclusion of a sialyl residue on Lewis[x], Lewis[a] and related compounds so as to provide for sialyl Lewis[x], sialyl Lewis[a] and related compounds results in a more complex and costly synthesis.

SUMMARY OF THE INVENTION

The present invention is directed, in part, to the discovery that modified Lewis[x] and modified Lewis[a] compounds having a sulfate, a phosphate or a carboxylate containing group possess enhanced immunosuppressive and tolerogenic properties as compared to similar compounds lacking such substitution. Moreover, the 3-sulfate Lewis[x] compound possesses at least equivalent immunosuppressive and tolerogenic properties as compared to sialyl Lewis[x]. This result is particularly surprising insofar as unmodified Lewis[x] possesses inferior immunosuppressive and tolerogenic properties as compared to sialyl Lewis[x]. Additionally, because these modified Lewis[x] and modified Lewis[a] compounds do not contain a sialyl residue at the 3-position of the galactose so as to form an α(2→3) linkage, the problems inherent with forming such a linkage are avoided.

Accordingly, in one of its composition aspects, the present invention is directed to compounds of Formula I:

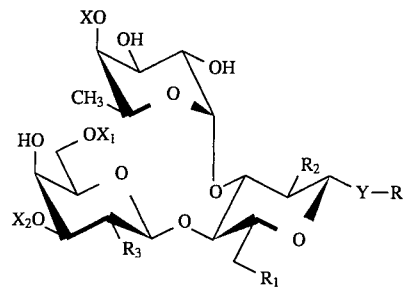

where R is selected from the group consisting of hydrogen, a saccharide-$OR_{14}$, an oligosaccharide-$OR_{14}$, or an aglycon having at least 1 carbon atom where $R_{14}$ is hydrogen or an aglycon of at least one carbon atom;

Y is selected from the group consisting of oxygen, sulfur, and —NH—;

$R_1$ is selected from the group consisting of hydrogen, —$NH_2$, —$N_3$, —$NHSO_3H$, —$NR_5C(O)R_4$, —N=$C(R_5)_2$, —$NHCH(R_5)_2$, —$NHR_6$, —$N(R_6)_2$, —OH, —$OR_6$, —$S(O)R_6$, —$S(O)_2R_6$ and sulfate, wherein $R_4$ is selected from the group consisting of hydrogen, alkyl of from 1 to 4 carbon atoms;

—$OR_7$ wherein $R_7$ is alkyl of from 1 to 4 carbon atoms, or alkyl of from 2 to 4 carbon atoms substituted with a hydroxyl group, and —$NR_8R_9$ wherein $R_8$ and $R_9$ are independently selected from the group consisting of hydrogen and alkyl of from 1 to 4 carbon atoms, each $R_5$ is selected from the group consisting of hydrogen and alkyl of from 1 to 4 carbon atoms, each $R_6$ is alkyl of from 1 to 4 carbon atoms, $R_2$ is selected from the group consisting of hydrogen, —$N_3$, —$NH_2$, —$NHSO_3H$, —$NR_{11}C(O)R_{10}$, —N=$C(R_{11})_2$, —$NHCH(R_{11})_2$, —$NHR_{12}$, —$N(R_{12})_2$, —OH and —$OR_{12}$, wherein $R_{10}$ is selected from the group consisting of hydrogen, alkyl of from 1 to 4 carbon atoms, —$OR_{13}$ wherein $R_{13}$ is alkyl of from 1 to 4 carbon atoms, or alkyl of from 2 to 4 carbon atoms substituted with a hydroxyl group, and —$NR_{14}R_{15}$ wherein $R_{14}$ and $R_{15}$ are independently selected from the group consisting of hydrogen and alkyl of from 1 to 4 carbon atoms, each $R_{11}$ is selected from the group consisting of hydrogen and alkyl of from 1 to 4 carbon atoms;

each $R_{12}$ is alkyl of from 1 to 4 carbon atoms, $R_3$ is selected from the group consisting of hydrogen, fluoro, sulfate and hydroxy;

X is selected from the group consisting of hydrogen, sulfate, and phosphate;

$X_1$ is selected from the group consisting of hydrogen, sulfate, phosphate, and —$CHR_{18}COOH$ where $R_{18}$ is selected from the group consisting of hydrogen, alkyl of from 1 to 7 carbon atoms and —COOH;

$X_2$ is selected from the group consisting of hydrogen, sulfate, phosphate, and —$CHR_{18}COOH$ where $R_{18}$ is selected from the group consisting of hydrogen, alkyl of from 1 to 7 carbon atoms and —COOH; and pharmaceutically acceptable salts thereof;

and with the proviso that either at least one of X, $X_1$, or $X_2$ is sulfate or phosphate or at least one of $X_1$ or $X_2$ is —$CHR_{18}COOH$.

The present invention is also directed to compounds of Formula II:

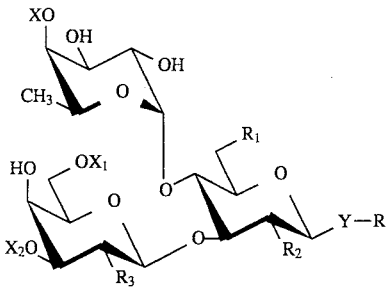

where R is selected from the group consisting of hydrogen, a saccharide-$OR_{14}$, an oligosaccharide-$OR_{14}$, or an aglycon having at least 1 carbon atom where $R_{14}$ is hydrogen or an aglycon of at least one carbon atom;

Y is selected from the group consisting of oxygen, sulfur, and —NH—;

$R_1$ is selected from the group consisting of hydrogen, —$NH_2$, —$N_3$, —$NHSO_3H$, —$NR_5C(O)R_4$, —$N=C(R_5)_2$, —$NHCH(R_5)_2$, —$NHR_6$, —$N(R_6)_2$, —OH, —$OR_6$, —$S(O)R_6$, —$S(O)_2R_6$ and sulfate, wherein $R_4$ is selected from the group consisting of hydrogen,
alkyl of from 1 to 4 carbon atoms;
—$OR_7$ wherein $R_7$ is alkyl of from 1 to 4 carbon atoms, or alkyl of from 2 to 4 carbon atoms substituted with a hydroxyl group, and
—$NR_8R_9$ wherein $R_8$ and $R_9$ are independently selected from the group consisting of hydrogen and alkyl of from 1 to 4 carbon atoms, each $R_5$ is selected from the group consisting of hydrogen and alkyl of from 1 to 4 carbon atoms, each $R_6$ is alkyl of from 1 to 4 carbon atoms, $R_2$ is selected from the group consisting of hydrogen, —$N_3$, —$NH_2$, —$NHSO_3H$, —$NR_{11}C(O)R_{10}$, —$N=C(R_{11})_2$, —$NHCH(R_{11})_2$, —$NHR_{12}$, —$N(R_{12})_2$, —OH and —$OR_{12}$, wherein $R_{10}$ is selected from the group consisting of hydrogen,
alkyl of from 1 to 4 carbon atoms,
—$OR_{13}$ wherein $R_{13}$ is alkyl of from 1 to 4 carbon atoms, or alkyl of from 2 to 4 carbon atoms substituted with a hydroxyl group, and
—$NR_{14}R_{15}$ wherein $R_{14}$ and $R_{15}$ are independently selected from the group consisting of hydrogen and alkyl of from 1 to 4 carbon atoms, each $R_{11}$ is selected from the group consisting of hydrogen and alkyl of from 1 to 4 carbon atoms;

each $R_{12}$ is alkyl of from 1 to 4 carbon atoms, $R_3$ is selected from the group consisting of hydrogen, fluoro, sulfate and hydroxy;

X is selected from the group consisting of hydrogen, sulfate, and phosphate;

$X_1$ is selected from the group consisting of hydrogen, sulfate, phosphate, and —$CHR_{18}COOH$ where $R_{18}$ is selected from the group consisting of hydrogen, alkyl of from 1 to 7 carbon atoms and —COOH;

$X_2$ is selected from the group consisting of hydrogen, sulfate, phosphate, and —$CHR_{18}COOH$ where $R_{18}$ is selected from the group consisting of hydrogen, alkyl of from 1 to 7 carbon atoms and —COOH; and pharmaceutically acceptable salts thereof;

and with the proviso that either at least one of X, $X_1$, or $X_2$ is sulfate or phosphate or at least one of $X_1$ or $X_2$ is —$CHR_{18}COOH$.

The compounds of Formula I and II are particularly useful in modulating a cell-mediated immune response to an antigen and in particular a cell-mediated immune inflammatory response to an antigen. In this regard, when the compounds of Formula I and II are administered to a mammal in response to an antigen challenge, such administration induces tolerance to later challenges from this same antigen.

In another of its composition aspects, the present invention is directed to a pharmaceutical composition suitable for administration to a mammal (e.g., human) which comprises a pharmaceutically inert carrier and an effective amount of the compound of Formula I or Formula II to modulate a cell-mediated immune response in said mammal.

In still another of its composition aspects, the present invention is directed to novel intermediates useful in preparing the compounds of Formula I and Formula II. In this regard, some of the intermediate monosaccharides disclosed herein are highly crystalline and can be produced in large quantities in high purity without the need for chromatography to separate these compounds.

In one of its method aspects, the present invention is directed to a method for modulating a cell-mediated immune response to an antigen in a mammal which method comprises administering to said mammal an amount of a compound of Formula I or Formula II effective in modulating said immune response.

In another of its method aspects, the present invention is directed to a method for preparing the compounds of Formula I and II above and to the preparation of intermediates useful in preparing the compounds of Formula I and II.

In this figure, because the 3,4-dihydroxyl groups of the 6-benzyl and 2-N-phthaloyl blocked glucosamine 15 are not blocked, reaction with 1-bromo-2,3,4,6-tetraacetyl galactose will result in formation of both the blocked βGal(1→4)βGlcNH$_2$ derivative 48 and the blocked βGal(1→3)βGlcNH$_2$ derivative (not shown).

In turn, these materials can be further derivatized at an appropriate point in the synthesis so as to provide for N-functionalized derivatives of Lewis$^x$ and Lewis$^a$.

Figure 7A:
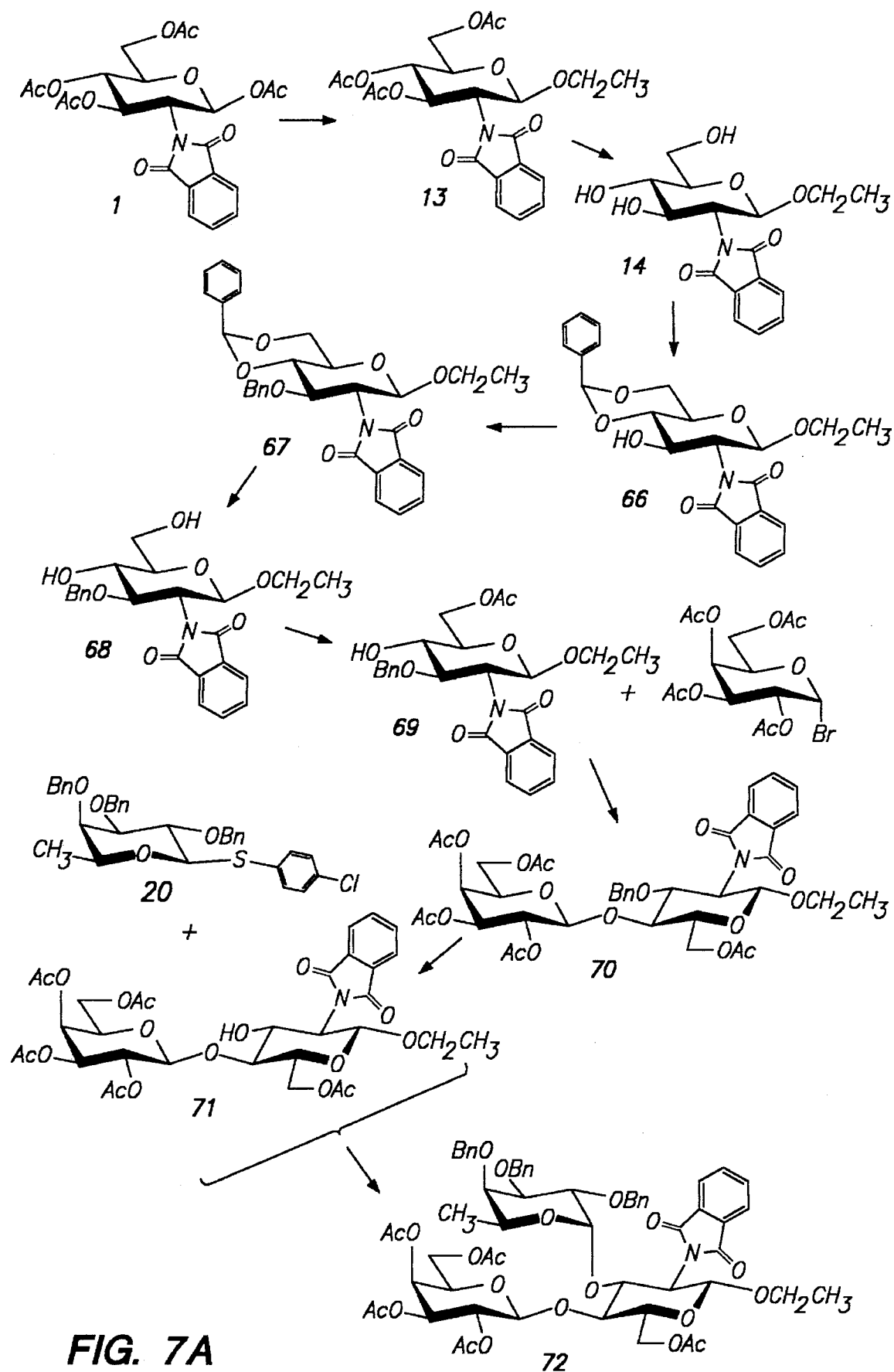
Figure 7B:
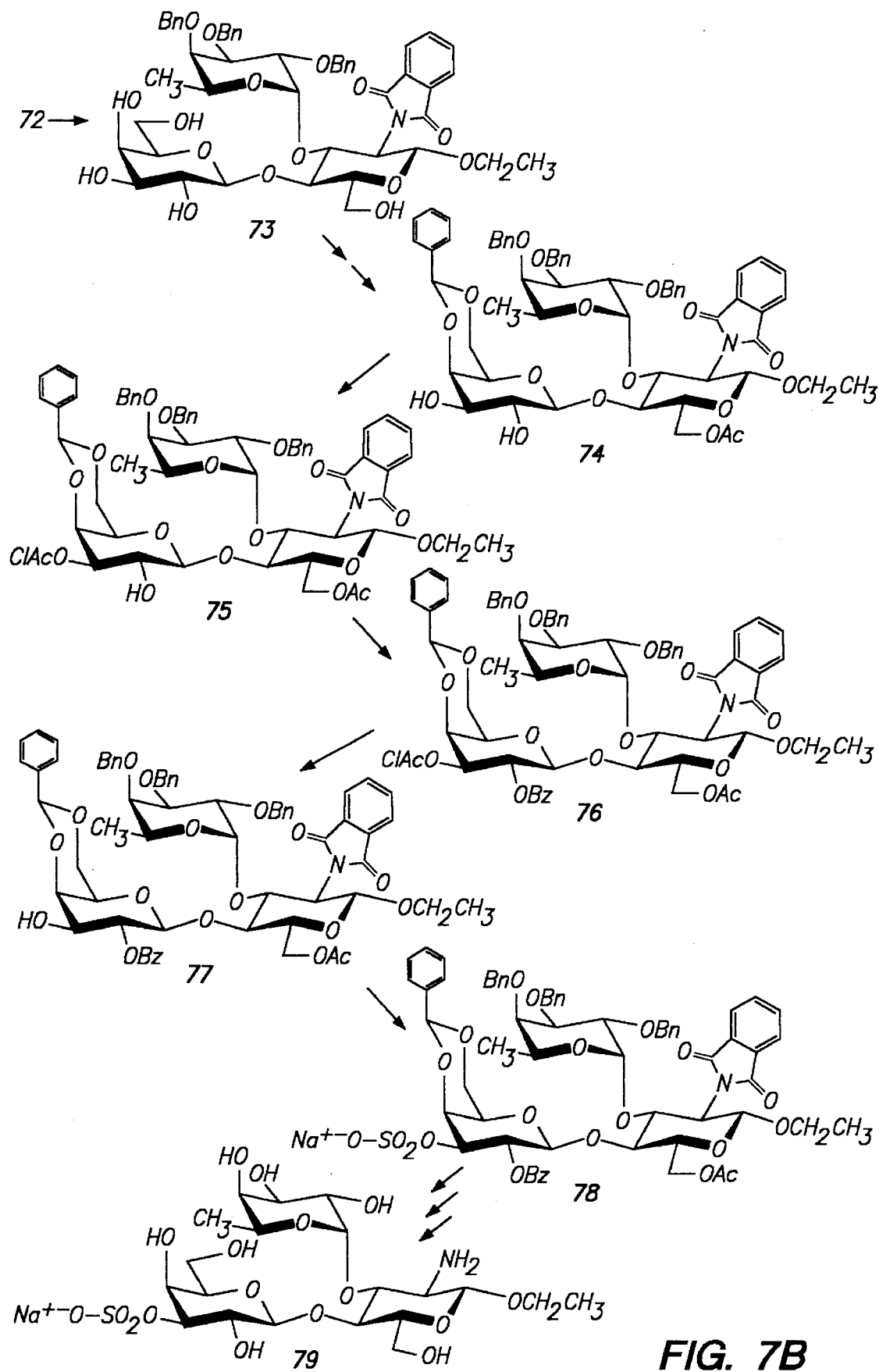

FIGS. 7A and 7B illustrates a second synthesis of modified Lewis$^x$ compounds bearing a sulfate substituent at the 3-position of the galactose and which utilize a different N-phthaloyl blocked glucosamine intermediate that allows for the selective preparation of 2-amino or N-functionalized Lewis$^x$ derivatives. In this figure, only the 4-position of the glucosamine is not blocked so that only the blocked βGal(1→4)βGlcNH$_2$ derivative 68 is formed.

Figure 8A:
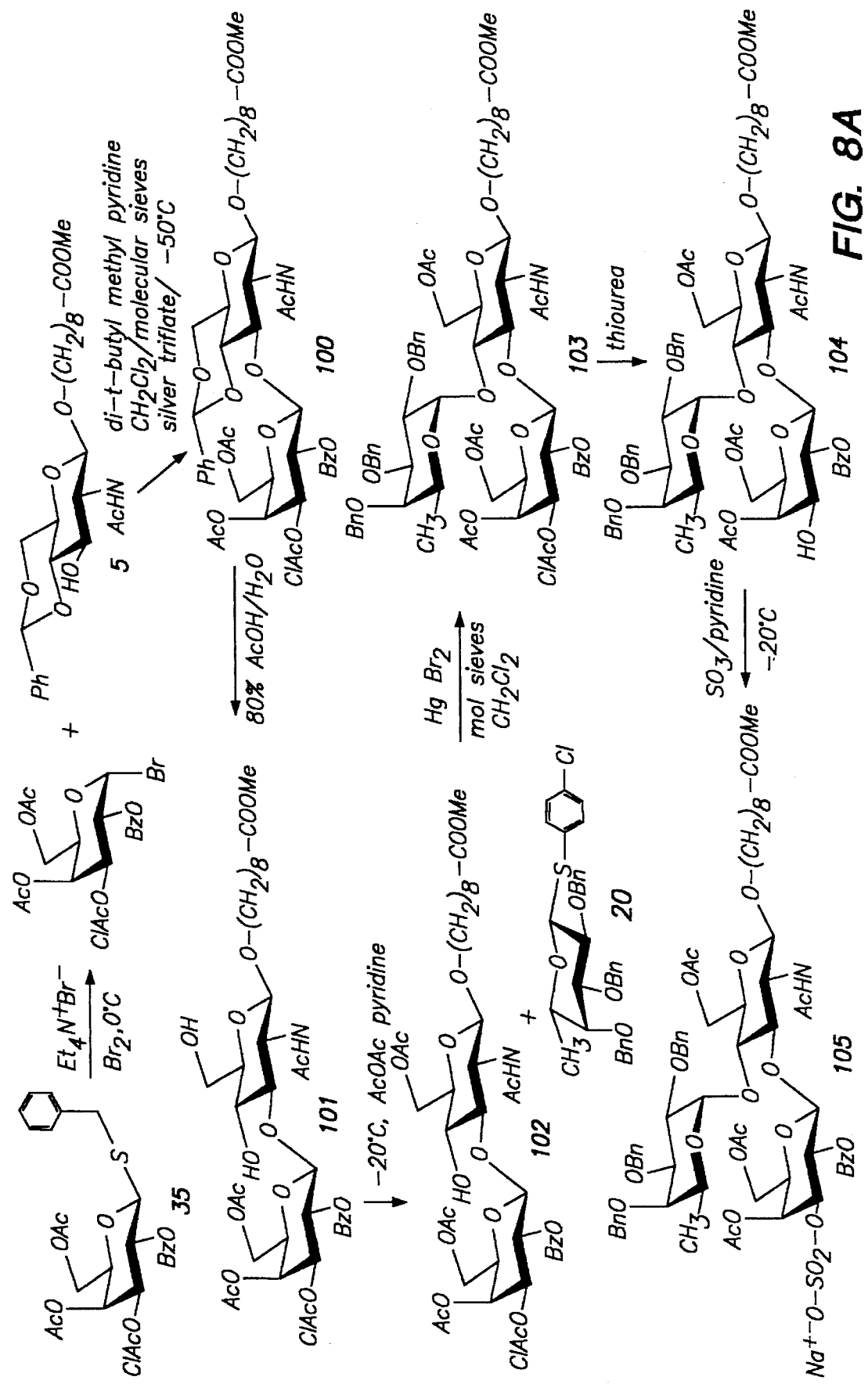
Figure 8B:
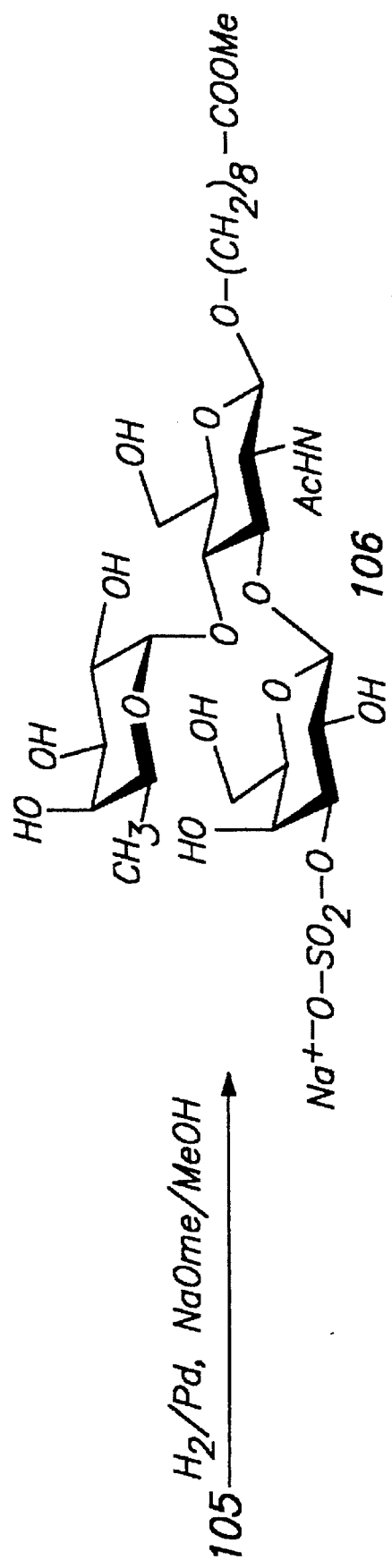

FIGS. 8A and 8B illustrates the preparation of modified Lewis$^a$ analogues having a sulfate substituent in the 3 position of the galactose unit. In this scheme, the 2,3 positions of galactose are differentially blocked so that the 3-position can be selectively deblocked and then selectively converted to the sulfate substituent.

Figure 9:
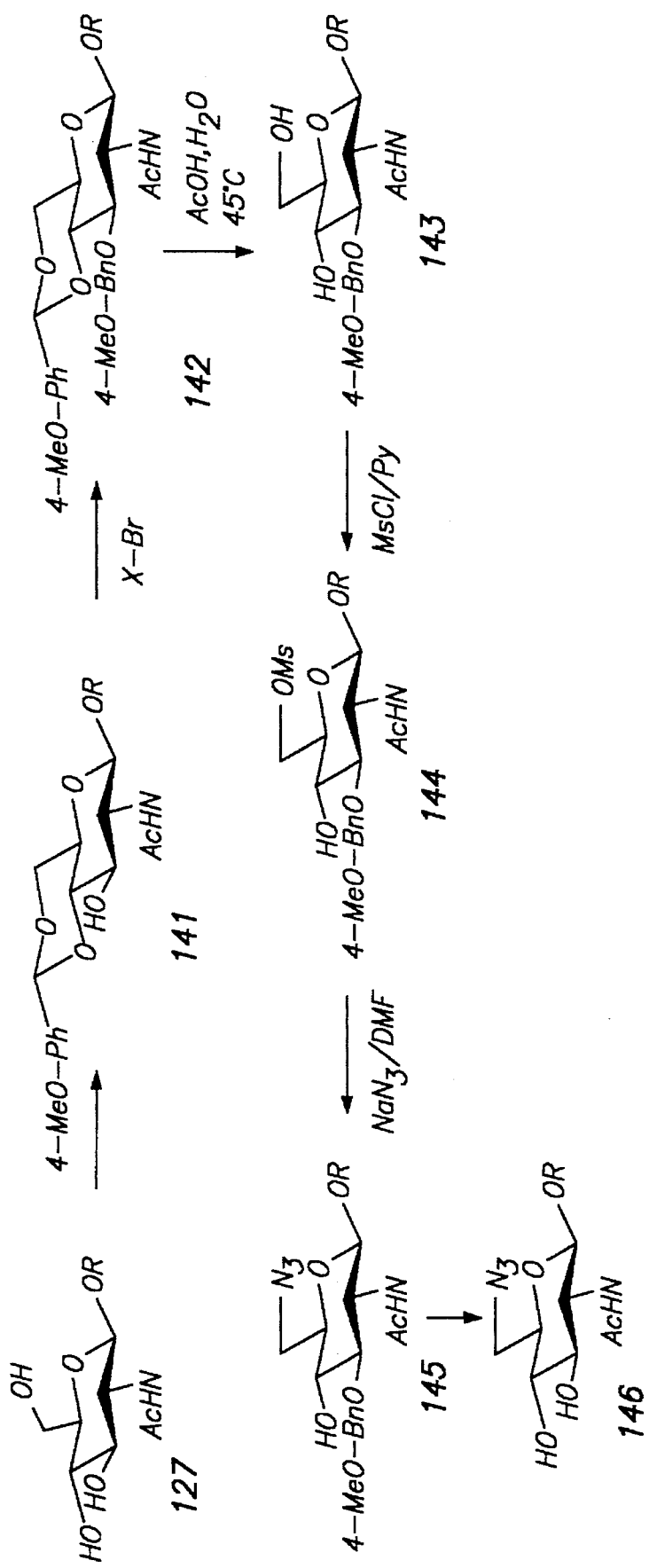

FIG. 9 illustrates the synthesis of the 6-azido derivative of GlcNAc-OR.

Figure 10:
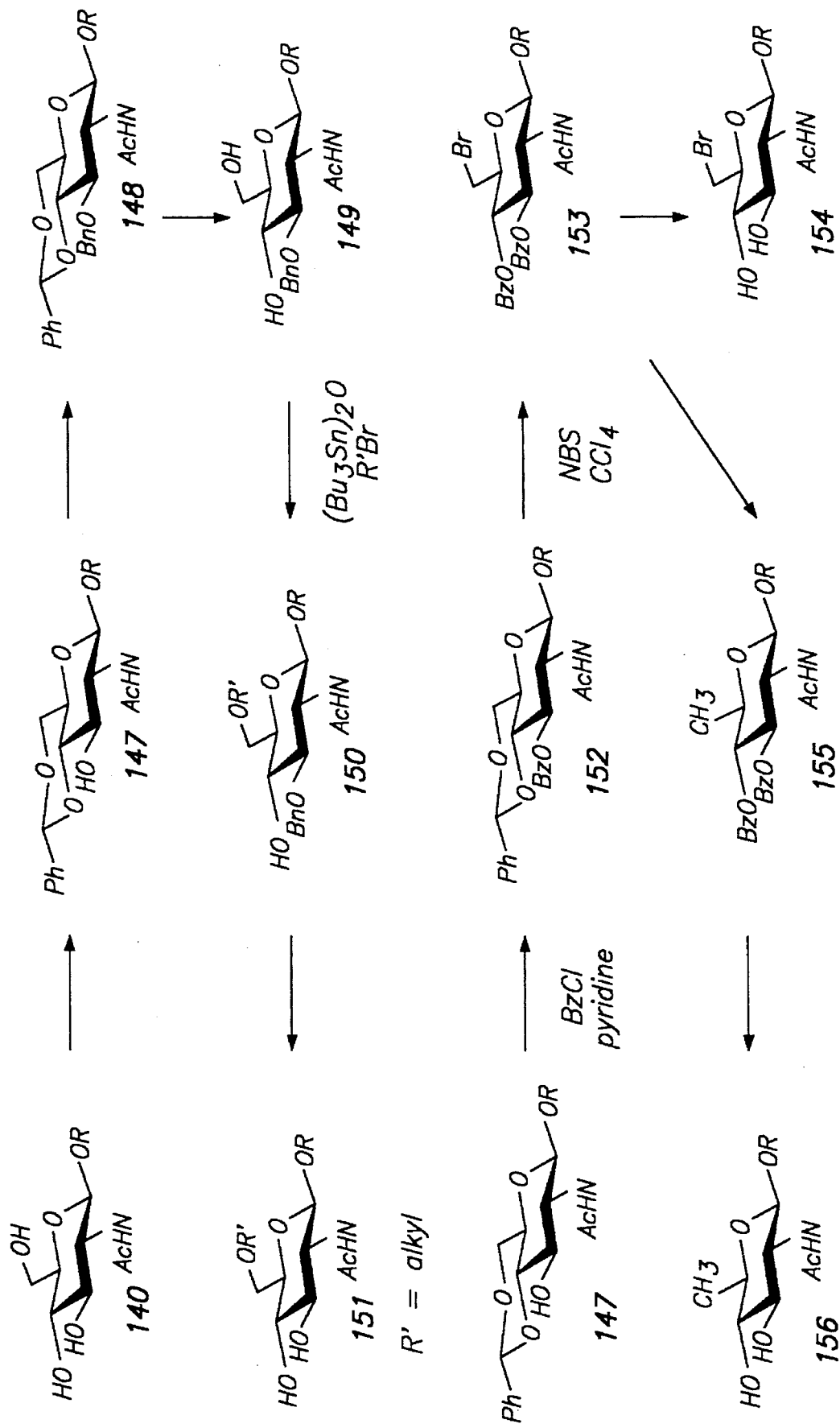

FIG. 10 illustrates the synthesis of the 6-alkoxy derivatives and the 6-deoxy derivatives of GlcNAc.

Figure 11:
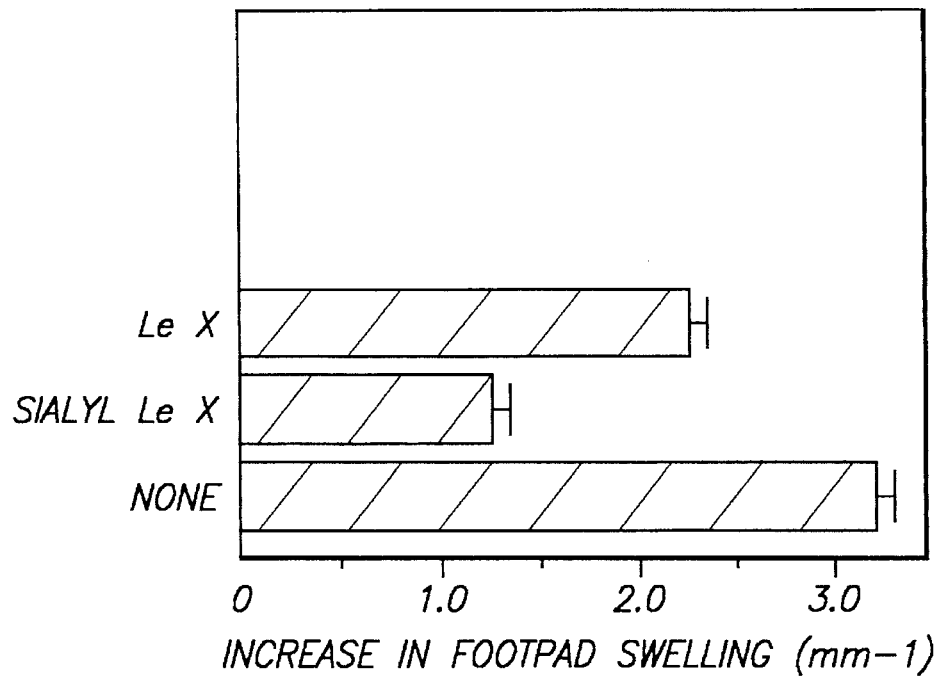

FIG. 11 illustrates the increase in footpad swelling of immunized mice arising from a DTH inflammatory response measured 24 hours after challenge with 10 μg of the L111 S-Layer protein antigen wherein some of the mice have been treated at 5 hours after the challenge with 100 μg of Lewis$^x$-OR and sialyl Lewis$^x$-OR (R=—O(CH$_2$)$_8$COOCH$_3$).

Figure 12:
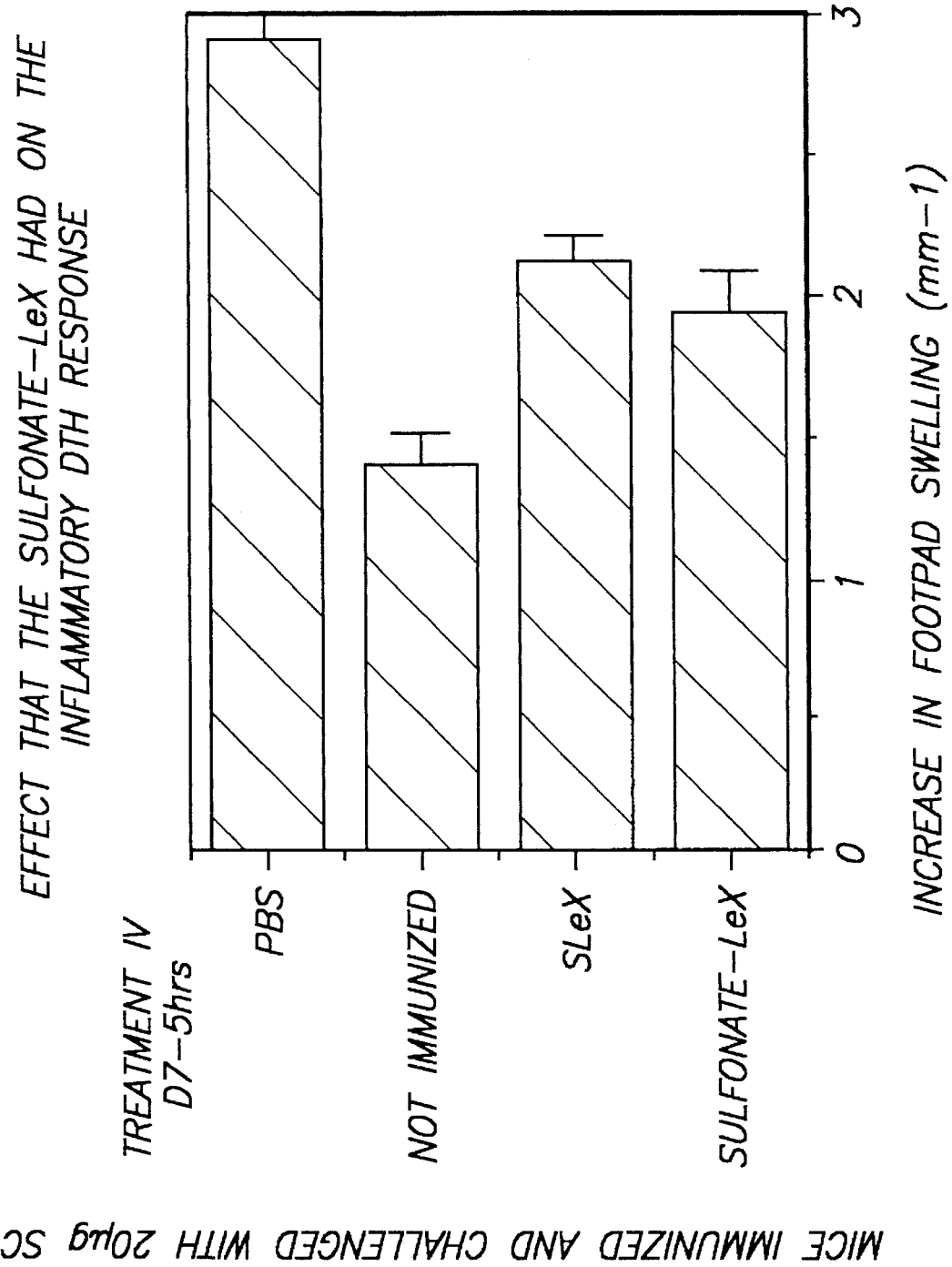

FIG. 12 illustrates the increase in footpad swelling of immunized mice arising from a DTH inflammatory response measured 24 hours after challenge with 20 μg of SuperCarrier (from Pierce, Rockford, Ill. 61105) antigen wherein some of the mice have been treated at 5 hours after the challenge with 100 μg of sialyl Lewis$^x$-OR (SLeX) and with 3-O-sulphate (on the galactose moiety) of the Lewis$^x$-OR (SULFONATE-LeX) where R is —O(CH$_2$)$_8$COOCH$_3$ in both cases.

Figure 13:
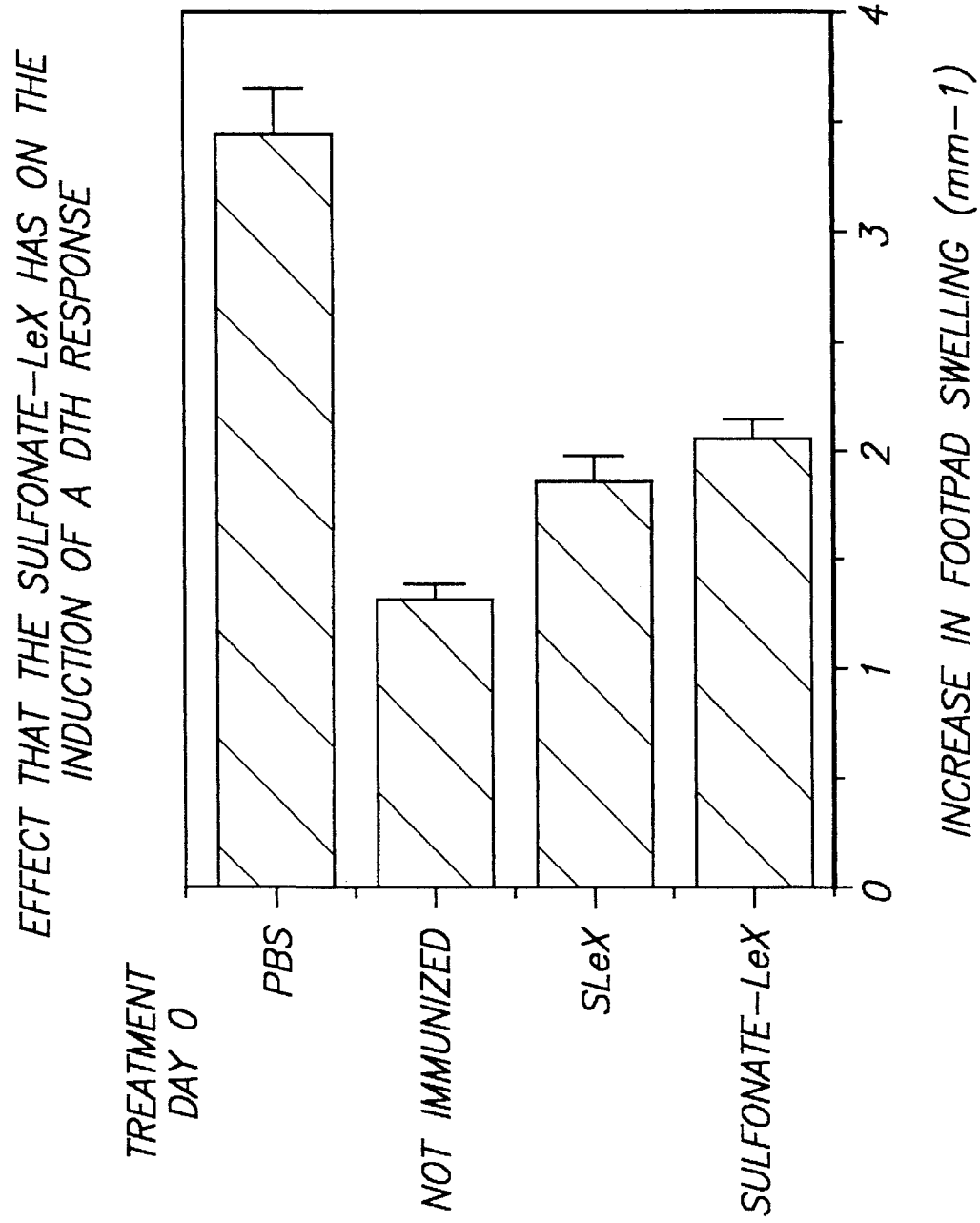

FIG. 13 demonstrates the effect that sulfated Lewis$^x$-OR (SULFONATE-LeX) has on the induction of an immune response to an antigen where R is as defined in FIG. 12.

Figure 14:
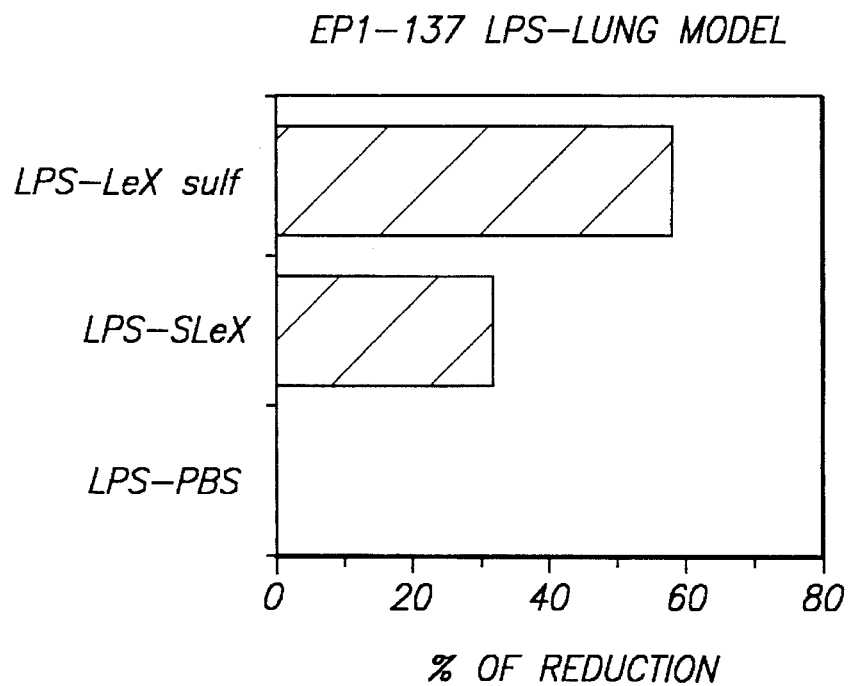

FIG. 14 illustrates the effect that sulfated Lewis$^x$-OR (LeXsulf) and sialyl Lewis$^x$-OR (SleX) on lung injury arising from the intranasal administration of LPS to mice (R is as defined in FIG. 12).

Figure 15:
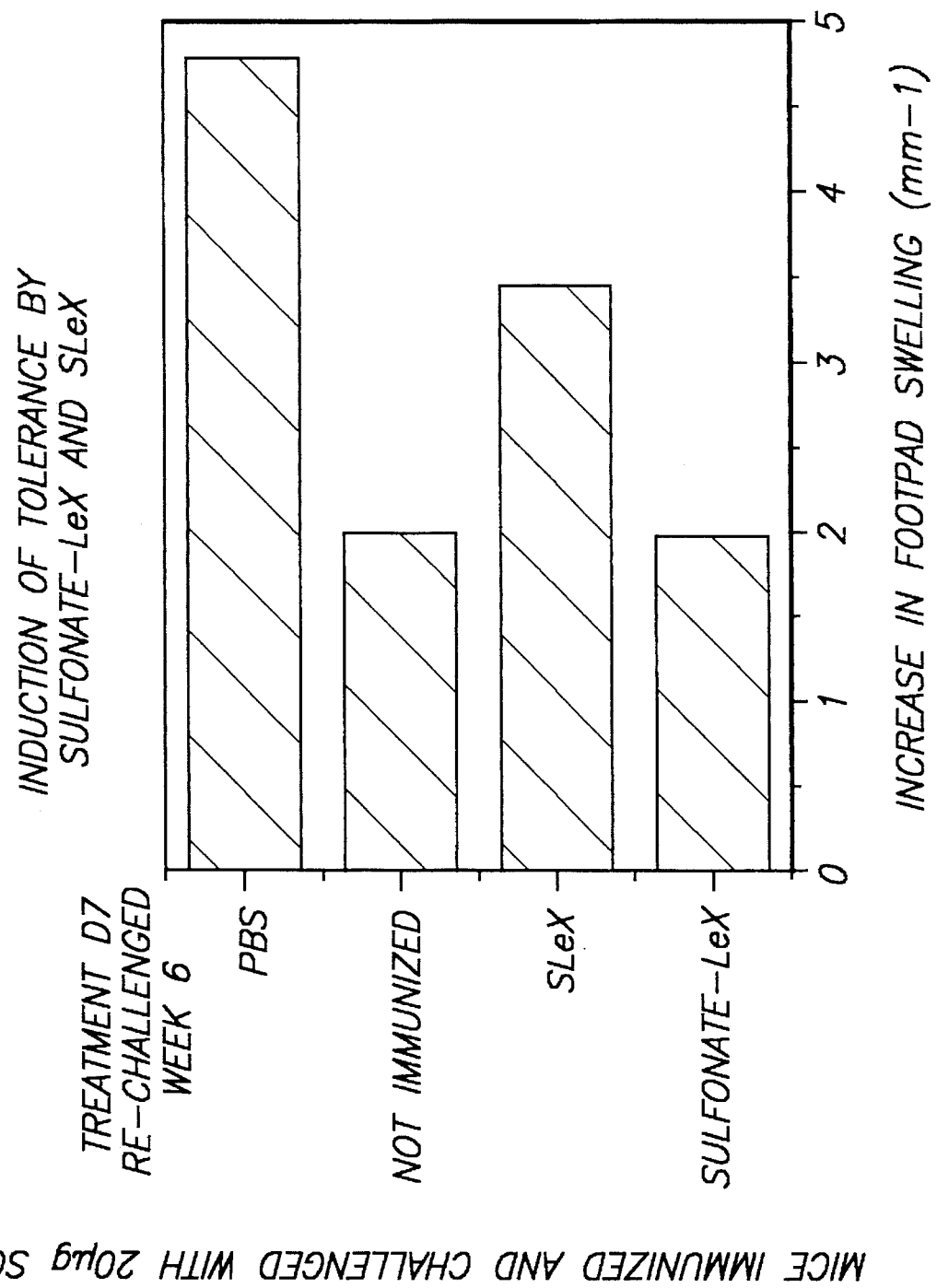

FIG. 15 demonstrates the long term tolerogenic effect of sulfated Lewis$^x$-OR (SULFONATE-LeX) and sialyl Lewis$^x$-OR (SLeX) on an immune response to an antigen where R is as defined in FIG. 12).

DETAILED DESCRIPTION OF THE PREFERRED EMBODIMENTS

As noted above, the present invention is directed, in part, to the discovery of novel Lewis$^x$ and novel Lewis$^a$ analogues which, in mammals, including humans, are useful for in vivo modulation (e.g., suppression) of a cell mediated immune response including cell-mediated and immune directed inflammatory responses to an antigen in a mammal (e.g., a DTH response).

Additionally, the present invention is directed, in part, to novel methods for the synthesis of Lewis$^x$ and for the synthesis of Lewis$^a$ analogues and to novel intermediates useful in these syntheses.

However, prior to discussing this invention in further detail, the following terms will first be defined.

Definitions

As used herein, the following terms have the definitions given below:

The term "cell-mediated immune response to an antigen in a mammal" refers to those mammalian immune responses which are mediated by cell-cell interactions. Included within this term are cell mediated inflammatory responses to an antigen such as DTH responses as well as cell-mediated inflammatory responses arising from myocardial infarction, virus-induced pneumonia, shock and sequelae (e.g., multiple organ failure), adult respiratory distress syndrome, psoriasis, arthritis, and the like. Preferably, the cell-mediated immune response is a leucocyte-mediated response.

The term "LacNAc" refers to the disaccharide βGal(1→4)βGlcNAc which is represented by the formula:

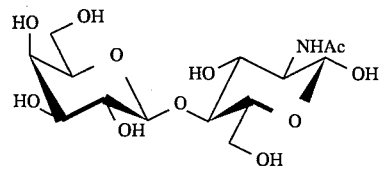

The term "LacNH$_2$" refers to the LacNAc derivative wherein the N-acetyl group of LacNAc has been replaced with an amine (—NH$_2$).

The term "LacN$_3$" refers to the LacNAc derivative wherein the N-acetyl group of LacNAc has been replaced with an azido (—N$_3$).

The term "Lewis$^x$" (sometimes referred to "Le$^x$") refers to the trisaccharide having the following structure:

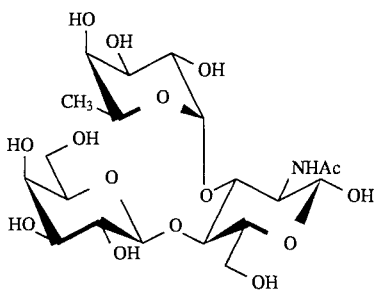

Because of its relationship to blood group determinants, the core βGal(1→4)βGlcNAc structure of Lewis$^x$ is often referred as a "type II structure" or "LacNAc structure".

The term "Lewis$^a$" (sometimes referred to "Le$^a$") refers to the trisaccharide having the following structure:

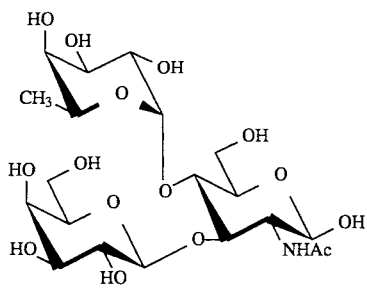

Because of its relationship to blood group determinants, the core βGal(1→3)βGlcNAc structure of Lewis$^a$ is often referred as a "type I structure".

The term "modified Lewis$^x$ glycosides and derivatives thereof" refer to derivatives of the Le$^x$ modified in one or more of the fucose, galactose and N-acetylglucosamine saccharide units of Lewis$^x$ and which have an —YR substituent as defined above. When the R substituent is an aglycon group, this group has at least one carbon atom, but nevertheless are different from glycoconjugates because such aglycon moieties are neither a protein nor a lipid capable of forming a micelle or other large aggregate structure.

The term "modified Lewis$^a$ glycosides and derivatives thereof" refer to derivatives of the Le$^a$ modified in one or more of the fucose, galactose and N-acetylglucosamine saccharide units of Lewis$^a$ and which have an —YR substituent as defined above. When the R substituent is an aglycon group, this group has at least one carbon atom, but nevertheless are different from glycoconjugates because such aglycon moieties are neither a protein nor a lipid capable of forming a micelle or other large aggregate structure.

The term "aglycon of at least one carbon atom" refers to non-saccharide containing residues having at least one carbon atom. Preferably, the aglycon is selected from the group consisting of —(A)—Z wherein A represents a bond, an alkylene group of from 2 to 10 carbon atoms, and a moiety of the form —(CH$_2$—CR$_{15}$G)$_n$— wherein n is an integer equal to 1 to 5; R$_{15}$ is selected from the group consisting of hydrogen, methyl, or ethyl; and G is selected from the group consisting of hydrogen, halogen, oxygen, sulphur, nitrogen, phenyl and phenyl substituted with 1 to 3 substituents selected from the group consisting of amine, hydroxyl, halo, alkyl of from 1 to 4 carbon atoms and alkoxy of from 1 to 4 carbon atoms; and Z is selected from the group consisting of hydrogen, methyl, phenyl, nitrophenyl and, when G is not oxygen, sulphur or nitrogen and A is not a bond, then Z is also selected from the group consisting of —OH, —SH, —NH$_2$, —NHR$_{16}$, —N(R$_{16}$)$_2$, —C(O)OH, —C(O)OR$_{21}$, —C(O)NH—NH$_2$, —C(O)NH$_2$, —C(O)NHR$_{16}$, —C(O)N(R$_{16}$)$_2$, and —OR$_{17}$ wherein each R$_{16}$ is independently alkyl of from 1 to 4 carbon atoms and R$_{17}$ is an alkenyl group of from 3 to 10 carbon atoms.

Numerous aglycons are known in the art. For example, an aglycon comprising a para-nitrophenyl group (i.e., —YR= —OC$_6$H$_4$pNO$_2$) has been disclosed by Ekberg et al.[18] At the appropriate time during synthesis, the nitro group is reduced to an amino group which can be protected as N-trifluoroacetamido. When desired, the trifluoroacetamido group is removed thereby unmasking the amino group.

An aglycon containing sulfur is disclosed by Dahmen et al.[19]. Specifically, the aglycon is derived from a 2-bromoethyl group which, in a substitution reaction with thionucleophiles, has been shown to lead to aglycons possessing a variety of terminal functional groups such as —OCH$_2$CH$_2$SCH$_2$CO$_2$CH$_3$ and —OCH$_2$CH$_2$SC$_6$H$_4$—pNH$_2$.

Rana et al.[20] discloses a 6-trifluoroacetamidohexyl aglycon (—O—(CH$_2$)$_6$—NHCOCF$_3$) in which the trifluoroacetamido protecting group can be removed unmasking the primary amino group.

Other exemplification of known aglycons include the 7-methoxycarbonyl-3,6,dioxaheptyl aglycon[21] (—OCH$_2$—CH$_2$)$_2$OCH$_2$CO$_2$CH$_3$; the 2 -(4-methoxycarbonylbutancarboxamido)ethyl[22](—OCH$_2$CH$_2$NHC(O)(CH$_2$)$_4$CO$_2$CH$_3$); and the allyl aglycon[23] (OCH$_2$CH=CH$_2$) which, by radical co-polymerization with an appropriate monomer,leads to co-polymers; other allyl linking aglycons[24] are known [e.g., —O(CH$_2$CH$_2$O)$_2$CH$_2$CH=CH$_2$]. Additionally, allyl linking arms can be derivatized in the presence of 2-aminoethanethiol[25] to provide for aglycons —OCH$_2$CH$_2$CH$_2$SCH$_2$CH$_2$NH$_2$. Still other aglycons are illustrated hereinbelow.

Additionally, as shown by Ratcliffe et al.[9], the R group can be an additional saccharide-OR$_{14}$ or an oligosaccharide-OR$_{14}$ at the reducing sugar terminus (where R$_{14}$ is as defined above).

Preferably, the aglycon moiety is a hydrophobic group and most preferably, the aglycon moiety is a hydrophobic group selected from the group consisting of —(CH$_2$)$_8$COOCH$_3$, —(CH$_2$)$_5$OCH$_2$CH=CH$_2$ and —(CH$_2$)$_8$CH$_2$OH.

The term "oligosaccharide" refers to a carbohydrate structure having from 2 to about 10 saccharide units. The particular saccharide units employed are not critical and include, by way of example, all natural and synthetic derivatives of glucose, galactose, N-acetylglucosamine, N-acetylgalactosamine, fucose, sialic acid, 3-deoxy-D,L-octulosonic acid, and the like.

In addition to being in their pyranose form, all saccharide units described herein are in their D form except for fucose which is in its L form.

The term "sialic acid" or "sialyl" means all naturally occurring structures of sialic acid and analogues of sialic acid. Naturally occurring structures of sialic acid include, by way of example, 5-acetamido-3,5-dideoxy-D-glycero-D-galactononulo-pyranosylonic acid ("Neu5Ac"), N-glycoyl neuraminic acid (Neu5Gc) and 9-O-acetyl neuraminic acid (Neu5,9Ac$_2$). Analogues of sialic acid refers to analogues of naturally occurring structures of sialic acid including those wherein the sialic acid unit has been chemically modified so as to introduce and/or remove one or more functionalities from such structures. For example, such modification can result in the removal of an —OH functionality, the introduction of an amine functionality, the introduction of a halo functionality, and the like.

Certain analogues of sialic acid are known in the art and include, by way of example, 9-azido-Neu5Ac, 9-amino-Neu5Ac, 9-deoxy-Neu5Ac, 9-fluoro-Neu5Ac, 9-bromo-Neu5Ac, 7-deoxy-Neu5Ac, 7-epi-Neu5Ac, 7,8-bis-epi-Neu5Ac, 4-O-methyl-Neu5Ac, 4-N-acetyl-Neu5Ac, 4,7-dideoxy-Neu5Ac, 4-oxo-Neu5Ac, as well as the 6-thio analogues of Neu5Ac. The nomenclature employed herein in describing analogues of sialic acid is as set forth by Reuter et al.[12]

The term "fucose" or "fucosyl" refers to L-fucose and analogues thereof. The fucose substituent can be attached to the derivatized Galβ(1→3)GlcNAcO-disaccharide (type I) or the derivatized Galβ(1→4)GlcNAcO-disaccharide (type II) so as to form the Lewis$^a$ or Lewis$^x$ moiety by either chemical or enzymatic means. While chemical means are illustrated in the figures, enzymatic means for attaching L-fucose to the 3-position of the GlcNAc unit of βGal(1→4)βGlcNAcO-lipid containing a sulfate on the 3-position of the galactose unit has been reported[28]. In such cases, the fucose employed, as its GDP-derivative, is one which is compatible with the fucosyltransferase (e.g., βGal(1→¾)βGlcNAc α(1→¾)fucosyltransferase). The βGal(1→¾)βGlcNAc α(1→¾)fucosyltransferase is readily isolated from human milk[13,14,15]. Additionally, it is contemplated that these fucose or fucosyl compounds will also be compatible with other fucosyltransferases of appropriate specificity such as cloned fucosyltransferases[29,30].

In regard to the above, any fucose compound which, as its GDP-derivative, is recognized by the βGal(1→¾)-βGlcNAc α(1→¾)fucosyltransferase so as to bind to the enzyme and is then available for transfer to the compound of Formula III or IV:

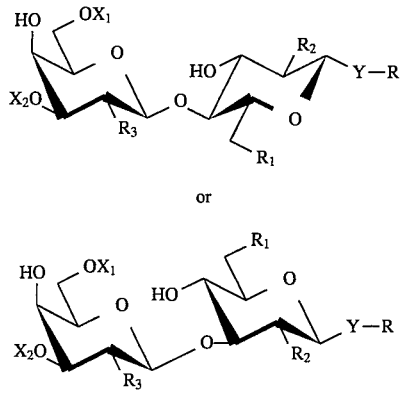

where R, R$_1$, R$_2$, R$_3$, X$_1$ and X$_2$ are as defined above, is said to be compatible with this fucosyltransferase.

Analogues of fucose refer to naturally occurring and synthetic analogues of fucose including those where the fucose unit has been chemically modified so as to introduce and/or remove one or more functionalities from this structure. For example, such modification can result in the removal of an -OH functionality, the introduction of an amine functionality, the introduction of a halo functionality, and the like.

Certain compatible analogues of fucose are known in the art and include, by way of example, 3-deoxy-fucose, arabinose, and the like.[16]

The GDP-derivative of fucose refers to guanosine 5'-(β-L-fucopyranosyl)diphosphate and any and all compatible salts thereof which has the formula:

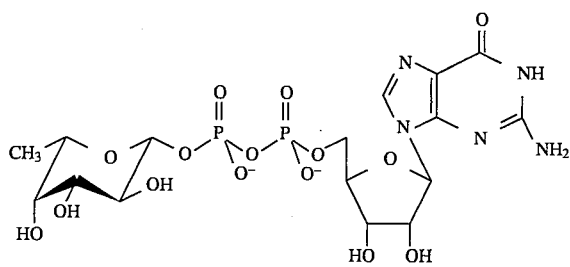

Methods for preparing GDP-fucose are known in the art. However, GDP-fucose is preferably prepared by the method described by Jiang et al.[17] in U.S. patent application Ser. No. 07/848,223 which is incorporated herein by reference in its entirety.

The term "compatible salts" as it is used in relation to guanosine 5'-(β-L-fucopyranosyl)diphosphate refers to those salts of guanosine 5'-(β-L-fucopyranosyl)diphosphate which readily form counter ions (i.e., cations) and which are compatible with the intended reactions and/or purifications. Suitable compatible salts include those prepared from counter ions such as sodium, potassium, lithium, calcium, magnesium, ammonium, mono-, di-, tri- or tetra-alkylammonium, iron, zinc, and the like.

The term "pharmaceutically acceptable salts" includes the pharmaceutically acceptable addition salts of the compounds of Formula I derived from a variety of organic and inorganic counter salts well known in the art and include, by way of example only, sodium, potassium, calcium, magnesium, ammonium, tetraalkylammonium, and the like.

The term "sulfate" such as used to define the substituents —OX, —OX$_1$, and —OX$_2$ refers to substituents which, with the oxygen of a hydroxyl group of the galactose unit and/or fucose group, form a sulfate group (i.e., —O—S(O)$_2$—OH). Thus, when X, X$_1$ or X$_2$ is a sulfate, the resulting —OX, —OX$_1$ and/or —OX$_2$ group is —O—S(O)$_2$—OH, which readily forms pharmaceutically acceptable salts thereof (e.g., —O—S(O)$_2$—O$^-$Na$^+$).

The term "phosphate" such as used to define the substituents —OX, —OX$_1$, and —OX$_2$ refers to substituents which, with the oxygen of a hydroxyl group of the galactose unit and/or fucose group, form a phosphate group (i.e., —O—P(O)$_2$—OH). Thus, when X, X$_1$ or X$_2$ is a phosphate, the resulting —OX, —OX$_1$ and/or —OX$_2$ group is —O—P(O)$_2$—OH, which readily forms pharmaceutically acceptable salts thereof (e.g., —O—P(O)$_2$—O$^-$Na$^+$).

The term "removable blocking group" refers to any group which when bound to one or more hydroxyl groups of the galactose, the N-acetylglucosamine, and/or the fucose units of Lewis$^x$ and Lewis$^a$ moieties prevents reactions from occurring at these hydroxyl groups and which protecting group can be removed by conventional chemical or enzymatic steps to reestablish the hydroxyl group. The particular removable blocking group employed is not critical and preferred removable hydroxyl blocking groups include conventional substituents such as benzyl, benzoyl, acetyl, chloroacetyl, benzylidine, t-butyldiphenylsilyl and any other group that can be introduced either enzymatically or chemically onto a hydroxyl functionality and later selectively removed either by enzymatic or chemical methods in mild conditions compatible with the nature of the product. One such additional contemplated blocking group is a α-galactose which can be removed enzymatically with an α-galactosidase.

2. Methodology

The modified Lewis$^x$ and modified Lewis$^a$ compounds disclosed herein are readily prepared either by complete chemical syntheses or by chemical/enzymatic syntheses wherein glycosyltransferases are employed to effect the sequential addition of one or more sugar units onto a GlcNAc-OR saccharide structure, a derivatized GlcNAc-OR saccharide structure, a LacNAc-OR disaccharide structure, a derivatized LacNAc-OR saccharide structure, a βGal(1→3)βGlcNAc-OR disaccharide structure, or a derivatized βGal(1→3)βGlcNAc-OR disaccharide structure.

The figures attached hereto elaborate on a variety of complete chemical synthetic schemes which result in the preparation of modified Lewis$^x$ and modified Lewis$^a$ compounds.

Enzymatic means to prepare modified Lewis$^x$ compounds and modified Lewis$^a$ compounds can be used at different steps. For example, L-fucose can be enzymatically transferred onto the deblocked sulfate, phosphate, or carboxylate containing derivatives of:

a LacNAc-OR structure or a derivatized LacNAc-OR structure (modified Lewis$^x$ compounds); or a βGal(1→3)βGlcNAc-OR structure or a derivatized βGal(1→3)βGlcNAc-OR structure (modified Lewis$^a$ compounds)

by an appropriate fucosyltransferase such as the βGal(1→¾)βGlcNAc α(1→¾)fucosyltransferase which is readily obtained from human milk[13,14,15].

The LacNAc-OR disaccharide can be made enzymatically from an N-acetyl glucosamine glycoside and the known β-galactose(1→4)transferase. The βGal(1→3)βGlcNAc-OR disaccharide glycoside can be made chemically.

Additionally, it is contemplated that sulfotransferases may be used to effect sulfation at the 3-position of galactose on either the type I or type II structures. As is apparent, this can be followed by transfer of fucose using an appropriate fucosyltransferase as described above.

Alternatively, chemical and enzymatic means can be coupled wherein, for example, the sulfated, phosphorylated, or —CHR$_{18}$COOH substituted LacNAc-OR structure or sulfated, phosphorylated, or —CHR$_{18}$COOH substituted βGal(1→3)βGlcNAc-OR structure is made chemically and the fucosyl group transferred enzymatically.

Chemical synthesis is a convenient method for preparing either the complete oligosaccharide glycoside; for chemically modifying a saccharide unit which can then be chemically or enzymatically coupled to an oligosaccharide glycoside; or for chemically preparing an oligosaccharide glycoside to which can be enzymatically coupled one or more saccharide units.

Several chemical syntheses of blocked intermediates exist[46,47,48]. These intermediates are suitable for the modifications described herein. Syntheses of these intermediates or similar ones utilizing methods known in the art allow the synthesis of the modified Lewis$^x$ and modified Lewis$^a$ compounds contained herein.

Figure 2:
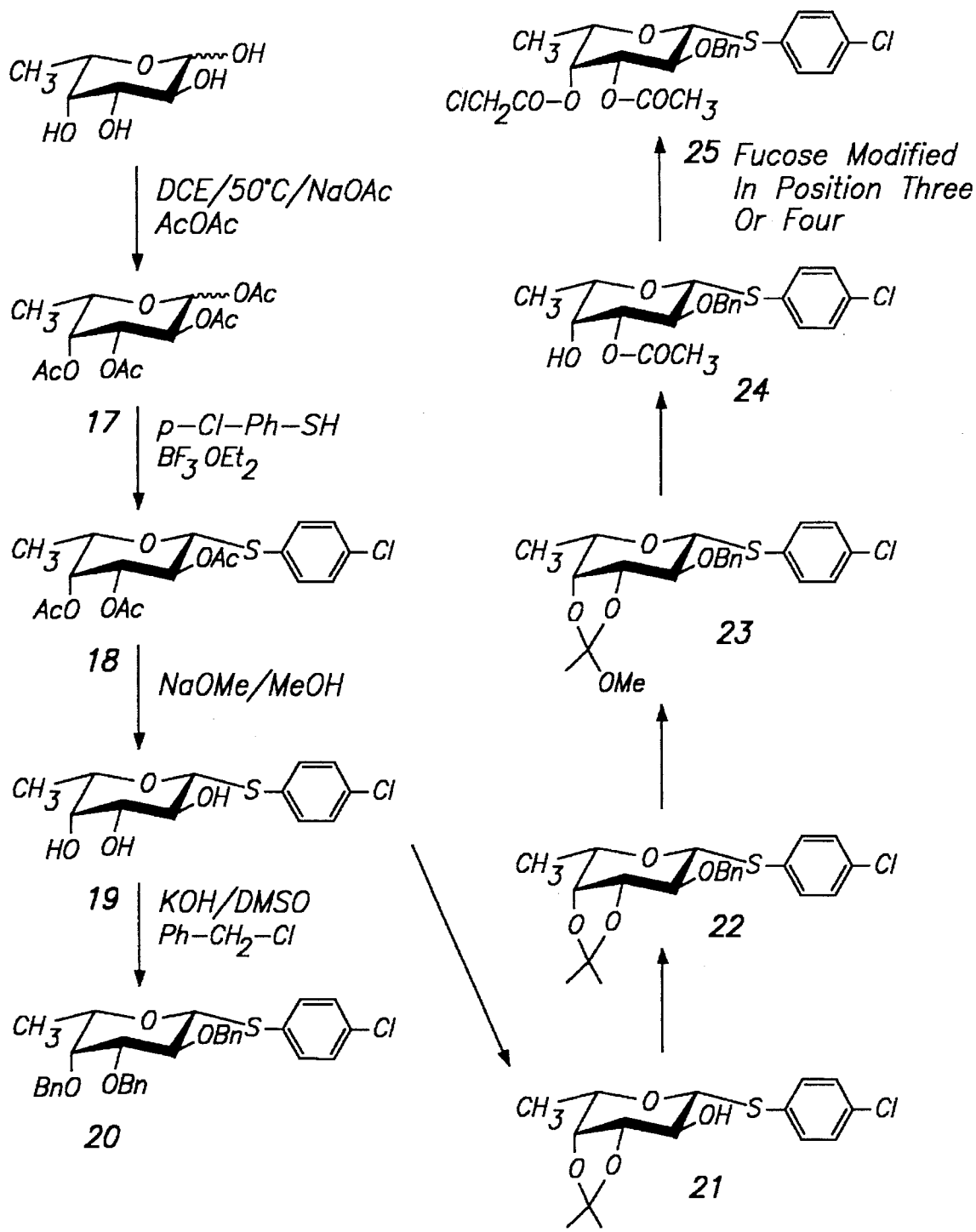
FIG. 2 illustrates reaction schemes for the synthesis of blocked fucose derivatives which are then used to prepare either modified Lewis$^x$ or modified Lewis$^a$ compounds.

Chemical modifications include introduction of the sulphate or phosphate group or a —OCHR$_{18}$COOH at the 3 and/or 6 position of the terminal galactose. Additionally the 3 or 4 position of the fucose can be sulphated or phosphorylated if the fucose intermediate 25 of FIG. 2 is employed rather than fucose intermediate 20.

2A. CHEMICAL SYNTHESIS OF SACCHARIDE MONOMERS

Chemical methods for the synthesis of Lewis$^x$ and Lewis$^a$ and some analogues thereof are known in the art. These materials are generally assembled using suitably protected individual monosaccharides including the desirable glucosamine, fucose and galactose or disaccharides such as lactose or βGal(1→3)βGlcNAc intermediates. The modifications to the final structures are accomplished using known methods for sulfation or phosphorylation after appropriate selective deblocking of the to-be functionalized hydroxyl group(s) of the fully blocked Lewis$^x$ or Lewis$^a$.

The specific methods employed are generally adapted and optimized for each individual structure to be synthesized. In general, the chemical synthesis of all or part of the oligosaccharide glycosides first involves formation of a glycosidic linkage on the anomeric carbon atom of the reducing sugar. Specifically, an appropriately protected form of a naturally occurring or of a chemically modified saccharide structure (the glycosyl donor) is selectively modified at the anomeric center of the reducing unit so as to introduce a leaving group comprising halides, trichloroacetimidate, acetyl, thioglycoside, etc. The donor is then reacted under catalytic conditions well known in the art with an aglycon or an appropriate form of a carbohydrate acceptor which possess one free hydroxyl group at the position where the glycosidic linkage is to be established. A large variety of aglycon moieties are known in the art and can be attached with the proper configuration to the anomeric center of the reducing unit. Appropriate use of compatible blocking groups, well known in the art of carbohydrate synthesis, will allow selective modification of the synthesized structures or the further attachment of additional sugar units or sugar blocks to the acceptor structures.

After formation of the glycosidic linkage, the saccharide glycoside can be used to effect coupling of additional saccharide unit(s) or chemically modified at selected positions or, after conventional deprotection, used in an enzymatic synthesis. In general, chemical coupling of a naturally occurring or chemically modified saccharide unit to the saccharide glycoside is accomplished by employing established chemistry well documented in the literature. See, for example, Okamoto et al.[31], Ratcliffe et al.[8], Abbas et al.[32], Paulsen[33], Schmidt[34], Fugedi et al.[35], and Kameyama et al.[36]

Figure 1A:
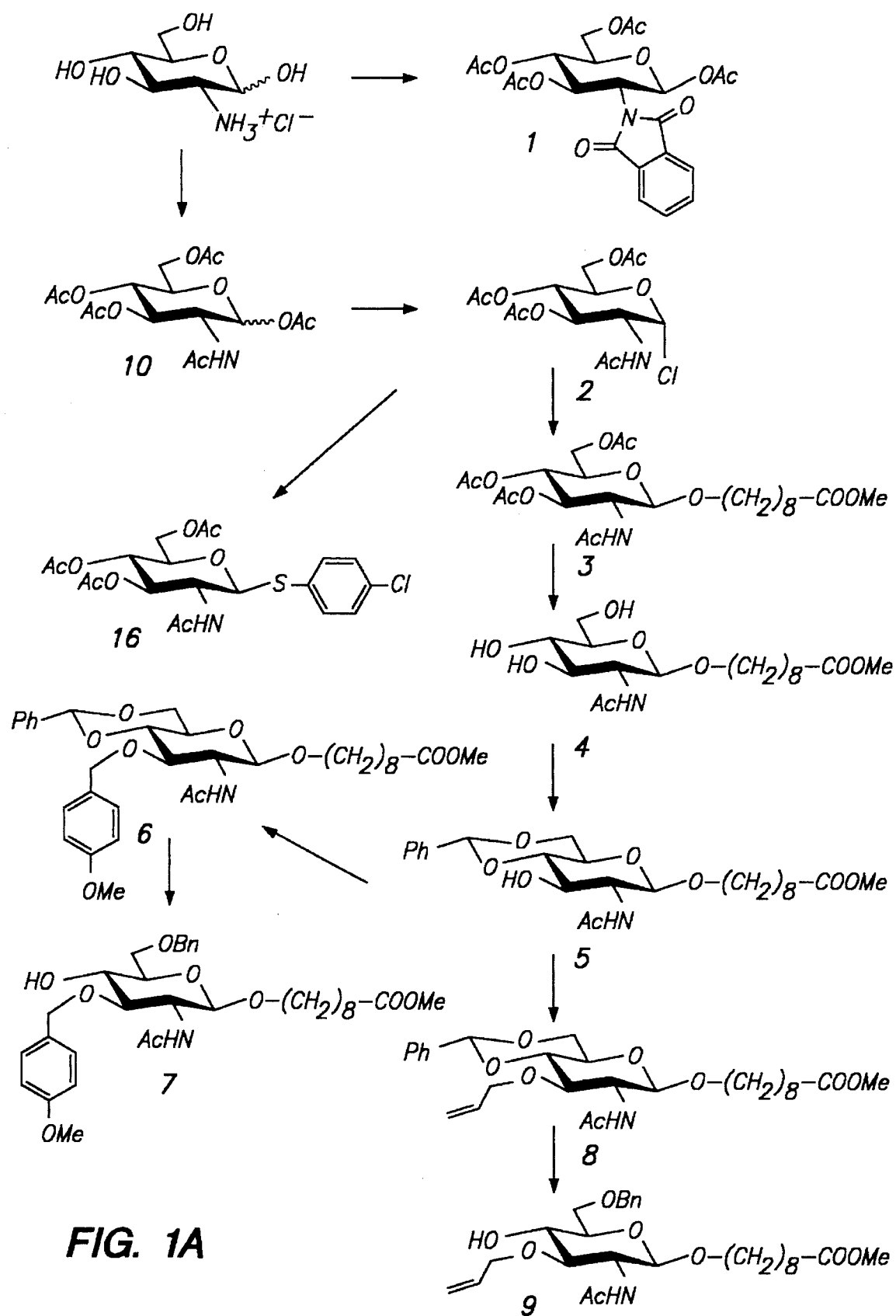
FIGS. 1A and 1B illustrates reaction schemes for the synthesis of partially blocked N-acetyl glucosamine derivatives which are then used to prepare either modified Lewis$^x$ compounds or modified Lewis$^a$ compounds.
Figure 1B:
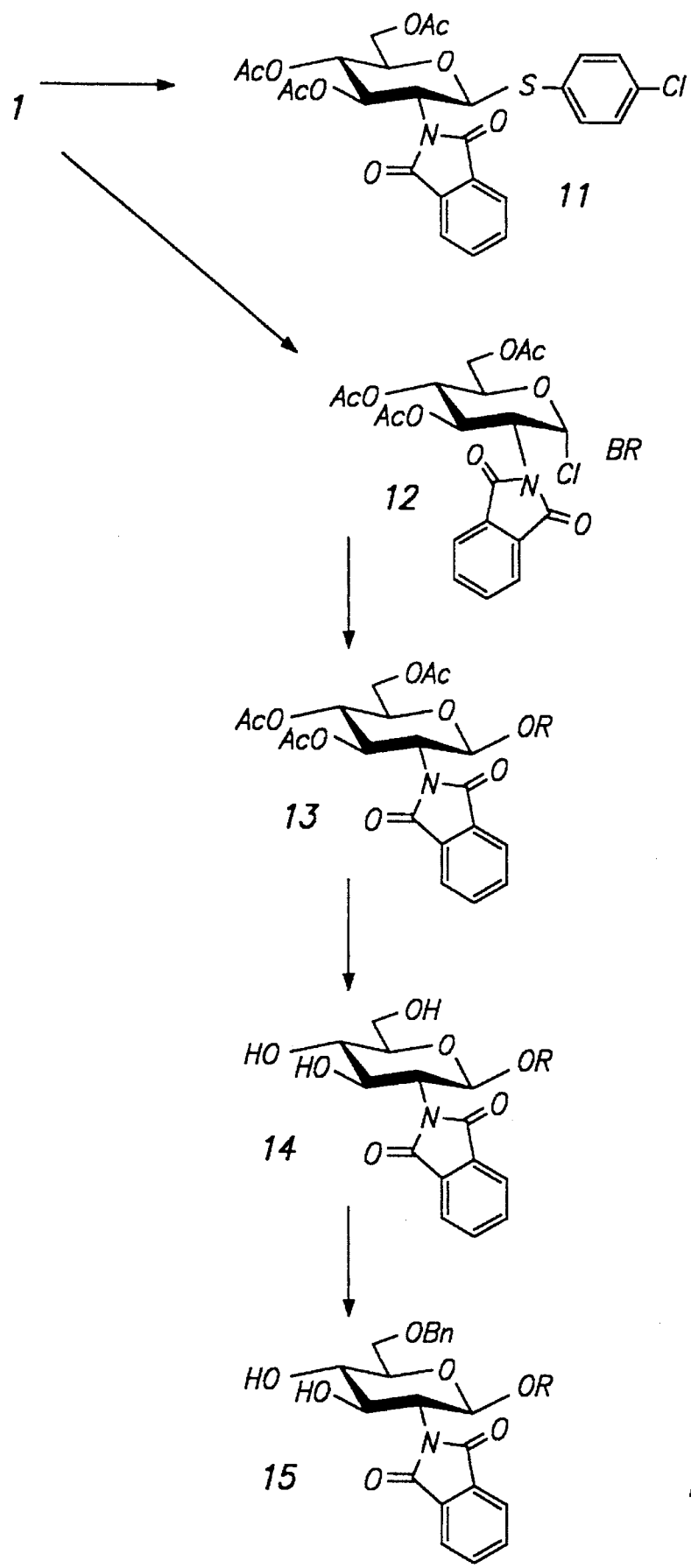

With reference to the figures, FIGS. 1A and 1B illustrates the synthesis of numerous blocked derivatives of glucosamine and N-acetylglucosamine which are then useful in the preparation of blocked LacNH$_2$-OR, LacNAc-OR, βGal(1→3)βGlcNAc-OR, βGal(1→3)βGlcNH$_2$-OR, etc. structures. Specifically, in FIGS. 1A and 1B, glucosamine hydrochloride is slurried in dichloroethane containing an equivalent of anhydrous sodium acetate to which acetic anhydride is added dropwise and, after addition is completed, the solution is refluxed for a period of from about 12–16 hours to provide for the peracylated compound 10 (about 3:1 ratio of α/β).

Alternatively, the glucosamine hydrochloride is first taken up in methanol and then treated with 1 equivalent of metallic sodium to neutralize the HCl. Phthalic anhydride is then quickly to the reaction mixture followed shortly thereafter by triethylamine to provide for the phthalimido derivative. This compound is then isolated and acetylated with acetic anhydride/pyridine using conventional techniques to provide for peracylated compound 1 having a phthalimide blocking group protecting the amine.

Afterwards, the aglycon is formed by conventional techniques. For example, compound 10 is converted to 1-α-chloro compound 2 by well known chemistry which involves bubbling saturating amounts of hydrogen chloride directly into a dichloroethane solution of compound 10. In this regard, the solution used to prepare compound 10 can be used in this reaction after that solution has been quenched into water to remove acetic anhydride and sodium acetate, dried and recovered. The reaction generally proceeds over a period of about 4–6 days and hydrogen chloride is bubbled into the solution periodically (e.g., about once every 1–2 days). After reaction completion, the solution is quenched in aqueous sodium bicarbonate at about 0°–5° C. and the product is recovered after drying the organic layer and stripping the solution to provide for compound 2 (one spot on t.l.c.)

Compound 2 is then converted to the 1-β-(CH$_2$)$_8$COOCH$_3$ aglycon by well known chemistry which involves reaction of compound 2 with HO(CH$_2$)$_8$COOCH$_3$ in anhydrous dichloromethane containing molecular sieves in the presence of an equivalent amount of mercuric cyanide. The reaction is generally conducted at room temperature for a period of about 12 to 24 hours. Upon reaction completion (as evidenced by t.l.c.), the reaction solution is filter through silica and the resulting solution is quenched by adding the reaction solution to cold water. The organic layer is recovered and the washed twice with an aqueous potassium iodide (5 weight/vol percent) solution and then with a saturated aqueous sodium bicarbonate solution. The resulting organic solution is then dried and the solvent removed by stripping to provide for compound 3.

The 3, 4, and 6 hydroxyl groups of compound 3 are then deprotected by reaction with sodium methoxide in methanol to provide for N-acetyl-glucosamine-OR, compound 4. This compound can reacted with C$_6$H$_5$CH(OCH$_3$)$_2$ in, for example, an acidic medium in an appropriate solvent at around 40°–50° C. for about 4–6 hours to provide for the 4,6-O-diprotected benzylidine compound 5. In turn, compound 5 can be reacted with p-methoxybenzyl trichloroacetimidate in an appropriate solvent (e.g., DMF, dichloromethane) in the presence of a catalytic amount of an acid (e.g., p-toluenesulfonic acid) to provide for the p-methoxybenzyl protected 3-hydroxy compound 6. Treatment of compound 6 with sodium cyanoborohydride in acetonitrile followed by the dropwise addition of HCl saturated ether at about 0° C. leads to compound 7.

Alternatively, compound 5 can be blocked at the 3-hydroxyl group by reaction with, for example, allyl bromide and base (e.g., barium hydroxide/barium oxide) to provide for compound 8. Treatment of compound 8 with sodium cyanoborohydride in tetrahydrofuran followed by the dropwise addition of HCl saturated ether at about 0° C. leads to compound 9.

Because compounds 7 and 9 contain only a free hydroxyl group at the 4-position of the blocked GlcNAc-OR saccharide, subsequent reaction with an appropriately blocked galactose will result in formation of a type II LacNAc-OR structure [βGal(1→4)βGlcNAc-OR].

Because compound 5 contains a free hydroxyl group only at the 3-position of the blocked GlcNAc-OR saccharide, subsequent reaction with an appropriately blocked galactose will result in formation of a type I structure [βGal(1→3)βGlcNAc-OR].

Alternatively, compound 1 can be converted to compound 11 by reaction of compound 1 with an equivalent of p-chlorothiophenol in dichloromethane at room temperature in the presence of 2 equivalents of boron trifluoride etherate BF$_3$.etherate to provide for compound 11.

In yet another embodiment, compound 1 is converted to compound 12 (or the bromo analogue) by following similar procedures set forth above for compound 2.

Compound 12 is converted to compound 13 (R=—CH$_2$CH$_3$) by reaction with ethanol in manner similar to that of compound 3 with the exception that ethanol replaces HO(CH$_2$)$_8$COOCH$_3$. Compound 13 is then converted to compound 14 with sodium methoxide/methanol and is then converted to compound 15 by reaction with bis[tributyltin] oxide in refluxing toluene containing tetraethylammonium bromide followed by reaction with benzyl bromide.

Because compound 15 contains free hydroxyl groups at the 3- and 4-positions of the blocked GlcNAc-OR saccharide, subsequent reaction with an appropriately blocked galactose will result in formation of both a type I structure [βGal(1→3)βGlcNAc-OR] and type II structure [βGal(1→4)βGlcNAc-OR] which are readily separated by conventional techniques including chromatography.

Compound 16 is prepared by treating p-chlorothiophenol with 0.95 equivalents of potassium hydroxide in ethanol followed by heating the solution to about 40°–50° C. and then adding about 0.5 equivalents of compound 2 to the reaction solution. The reaction is maintained at 40°–50° C. for about 1–2 hours and the product 16 precipitates upon cooling the solution and is recovered by filtration.

In FIG. 2, the synthesis of compounds 17–20 are set forth in the examples hereinbelow. The process to produce the highly crystalline fucose intermediate 20 from L-fucose as shown in FIG. 2 is novel. This procedure optimizes the production of β-fucopyranose tetraacetate 17 by adding acetic anhydride (AcOAc) dropwise to a slurry of fucose and about equimolar amounts (e.g., about 1.1 equivalents) of sodium acetate (NaOAc) maintained at about 50°–55° C. in dichloroethane (DCE) and stirred at this temperature for a sufficient period of time to result in formation of compound 17 (e.g., for about 2–3 days). The reaction mixture is treated with water, quenched into ice water, extracted with additional dichloromethane and dried and partially concentrated to provide the peracylated compound 17 (about 4:1 β/α ratio of 1-acetate).

Compound 17 is then reacted with an approximately equivalent amount of p-chlorothiophenol (p-Cl-Ph-SH) and approximately 1 to 3 (preferably 2) equivalents of boron trifluoride etherate (BF$_3$.OEt$_2$) in a suitable solvent (e.g., dichloromethane) to provide the p-chlorophenyl 2,3,4-tri-O-acetyl-β-thiofucopyranoside, compound 18. The reaction conditions employed are not critical and temperatures of from about 0° to about 25° C. (preferably at room temperature) and reaction times of about 3 to about 16 hours can be used.

Compound 18 is quickly deacetylated under Zemplen conditions (NaOMe, MeOH) to yield p-chlorophenyl β-thiofucopyranoside 19 as a crystalline product in 55–65% overall yield from fucose after recrstallization from an appropriate solvent (e.g., isobutanol). Again, the reaction conditions employed are not critical and temperatures of from about 15° to about 30° C. and reaction times of about 1 to about 10 hours can be used.

Compound 19 is, in turn, readily benzylated with benzyl chloride or benzyl bromide to yield p-chlorophenyl 2,3,4-tri-O-benzyl-β-thiofucopyranoside, compound 20, in 45–50% overall yield from fucose. As before, the reaction conditions employed are not critical and temperatures of from about 15° to about 30° C. and reaction times of about 24 to about 48 hours can be used. In general, at least 3 equivalents of benzyl chloride or bromide are employed and the reaction is generally conducted in the presence of at least about 4–5 equivalents of a suitable base (e.g., potassium hydroxide—KOH) in a suitable inert solvent (e.g., dimethoxysulfoxide—DMSO).

In a preferred embodiment, about 3 equivalent of base are added to the reaction system prior to addition of about 3 equivalents benzyl chloride or benzyl bromide. After about 18 hours, an additional 1.5 equivalents of base and an additional equivalent of benzyl chloride are added.

The simple reagents, easy processing and highly crystalline products eliminate the chromatography that frequently has been required using heretofore described methodology.

Thus, in this aspect, the present invention relates to a method for the preparation of p-chlorophenyl 2,3,4-tri-O-benzyl-β-thiofucopyranoside which comprises the steps:

(a) contacting L-fucose with sodium acetate in dichloroethane maintained at a temperature of from about 50°–55° C. while adding dropwise at least 4 equivalents of acetic anhydride;

(b) maintaining the solution produced in step (a) above at about 50°–55° C. for a sufficient period of time so as to produce the 1,2,3,4-tetraacetylated derivative of L-fucose;

(c) reacting the product produced in step (b) above with at least one equivalent of p-chlorothiophenol and from about 1 to about 3 equivalents of boron trifluoride etherate under conditions sufficient to provide the p-chlorophenyl 2,3,4-tri-O-acetyl-β-thiofucopyranoside;

(d) removing the acetyl blocking groups by contacting the p-chlorophenyl 2,3,4-tri-O-acetyl-β-thiofucopyranoside with sodium methoxide and methanol under conditions sufficient to provide for p-chlorophenyl β-thiofucopyranoside; and (e) contacting the p-chlorophenyl β-thiofucopyranoside produced in step (d) with benzyl chloride or benzyl bromide in the presence of a base and under conditions sufficient to provide for p-chlorophenyl 2,3,4-tri-O-benzyl-β-thiofucopyranoside.

The synthesis of compounds 21–24 are conducted by following known techniques, for example those described by Matta et al.[27] In the procedure of Matta et al., compound 23 can be converted to either a 3-acetyl (compound 24) or the 4-acetyl blocking group (not shown). In turn, both of these compounds are then blocked at the remaining hydroxyl group with a chloroacetyl blocking group by acetylation with chloroacetylchloride in pyridine/dichloromethane at about 0° C.

This results in compounds which have differentially protected 3,4-hydroxy groups. The chloroacetyl blocking group in either compound can be selectively removed at the appropriate point in the synthesis by treatment with thiourea in pyridine/ethanol (6:1) and then reacted to form the sulfate or phosphate in the manner described below.

Figure 3A:
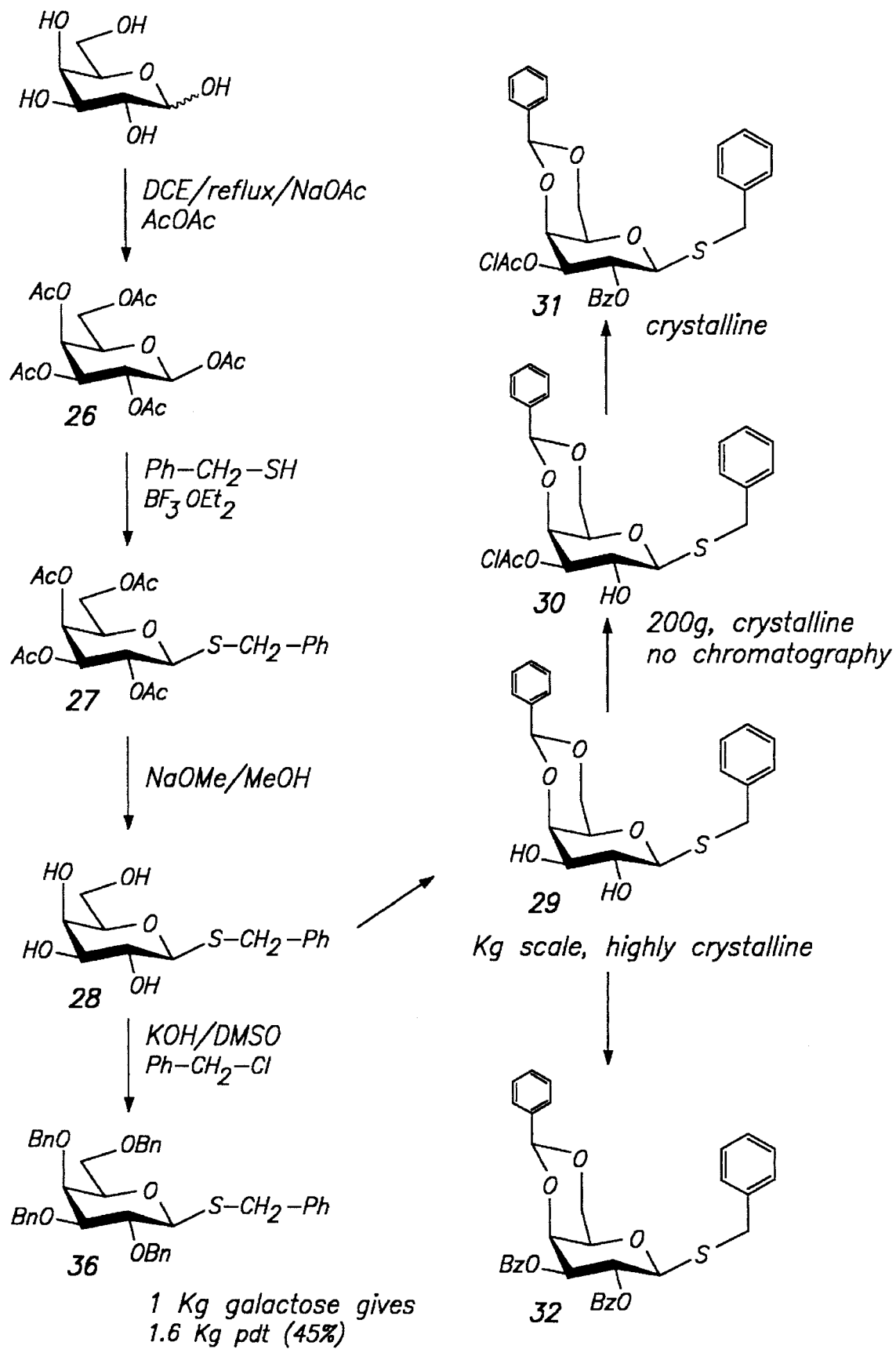
FIGS. 3A and 3B illustrates reaction schemes for the synthesis of partially blocked galactose derivatives which are then used to prepare either modified Lewis$^x$ compounds or modified Lewis$^a$ compounds.
Figure 3B:
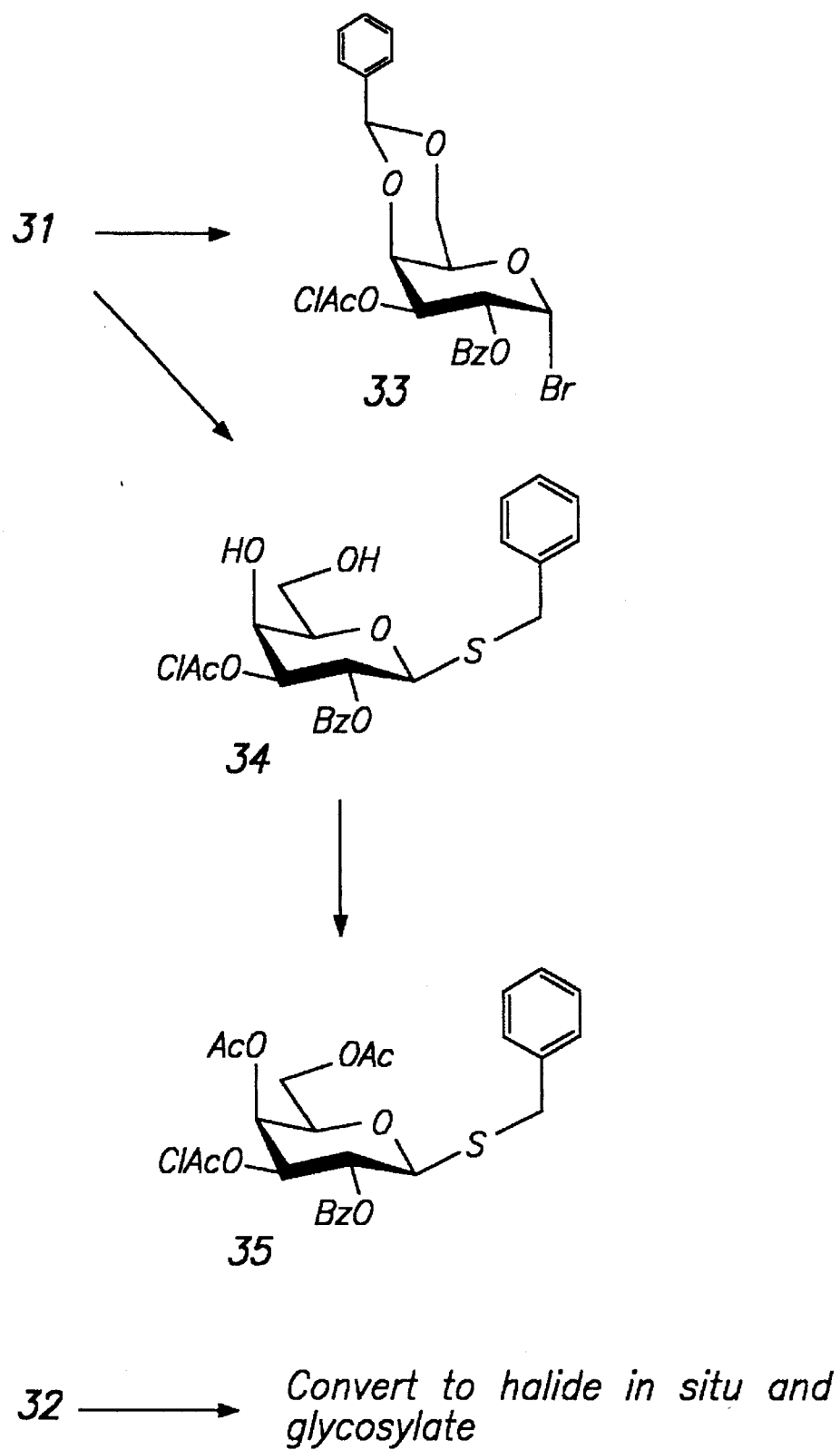

The synthesis of compounds 26–31 are depicted in FIGS. 3A and 3B and are set forth in the examples hereinbelow. In this figure, the synthesis of compounds 26, 27, 28, and 36 parallels that of compounds 17, 18, 19, and 20 as set forth above and illustrated in FIG. 2. In this regard, benzyl 4,6-O-benzylidene-2-O-benzoyl-3-O-chloroacetyl-β-D-thiogalactopyranoside (compound 31) has been produced without the necessity of chromatography. D-Galactose pentaacetate 26 is produced by slurring D-galactose and about an equimolar amount (e.g., about 1.1 equivalents) of sodium acetate (NaOAc) in dichloroethane (DCE), heating to reflux and adding at least 5 equivalents of acetic anhydride (AcOAc) dropwise to the refluxing solution (about 80°–85° C.) and then maintaining the reaction system at this temperature for a sufficient period of time (about 16–32 hours) to result in formation of compound 26. This procedure optimizes the yield of β-D-galactose pentaacetate 26 and controls the exotherm of heretofore known procedures.

After workup of the solution in a similar manner to that described above for compound 17, the product is treated with approximately equimolar amounts of benzyl mercaptan (Ph-CH$_2$-SH) and from about 1–3 (preferably two) equivalent of boron trifluoride etherate (BF$_3$.OEt$_2$) in dichloromethane. The reaction conditions are not critical and the reaction is preferably conducted at from about 0° C. to about 30° C. for a period about 6 to 16 hours to yield after crystallization from hot methanol or hot isopropanol 55–65% of benzyl 2,3,4,6-tetra-O-acetyl β-D-thiogalactopyranoside, compound 27.

Deacetylation under Zemplen conditions (sodium methoxide/methanol) leads to compound 28. Deacetylation reaction conditions are not critical and the reaction is generally conducted at room temperature for a period of from about 2 to about 15 hours. After the deacetylation reaction is complete (as judged by t.l.c.), the solution is neutralized with an acid ion exchange resin, filtered and evaporated to dryness to provide for compound 28. The residue is crystallized from hot acetone and the product is taken up in dimethylformamide or acetonitrile and treated with from 1 to 2 equivalents (preferably 1.4 equivalents) of benzaldehyde dimethyl acetal and about 0.25 to 3 weight percent of p-toluenesulphonic acid (based on compound 28). The reaction conditions are not critical and preferably the reaction is conducted at room temperature and is generally complete in about 12 to 24 hours. After neutralization, the benzyl 4,6-O-benzylidene β-D-thiogalactopyranoside, 29, is isolated and crystallized from hot isopropanol.

Benzyl 4,6-O-benzylidene-3-O-chloroacetyl-β-D-thiogalactopyranoside 30 is prepared by chloroacetylation using from about 1 to 3 (preferably 2) equivalents of chloroacetylchloride which is added to a dimethylformamide (DMF) solution containing benzyl 4,6-O-benzylidene β-D-thiogalactopyranoside 29. The chloroacetylchloride is added dropwise while maintaining the DMF solution at from about −40° to about −15° C. (preferably at −25° C.). Under these conditions, it is unexpectedly been found that the use of DMF permits selective chloroacetylation of compound 29 without the need for additional base. The reaction is generally complete in about 10–24 hours.

Benzyl 4,6-O-benzylidene-3-O-chloroacetyl-β-D-thiogalactopyranoside (compound 30) is benzoylated with at least 1 equivalent (and preferably about 2 equivalents) of benzoyl chloride in a suitable solvent containing a base (e.g., pyridine/methylene chloride) with from about 0.1 to about 1 weight percent of dimethylaminopyridine [DMAP] as a catalyst. The reaction conditions are not critical and preferably the reaction is conducted at from about 0° C. to about 30° C. and for about 1 to about 4 hours (preferably room temperature for 2 hours) to give crystalline benzyl 4,6-O-benzylidene 2-O-benzoyl-3-O-chloroacetyl-β-D-thiogalactopyranoside, compound 31, in approximately 10–20% overall yield from galactose.

The advantage of this approach is that after subsequent assembly the blocked intermediates will be simply deblocked and modified by sulfation or phosphorylation. The material is crystalline and the process obviates the need for chromatography. The sulfates and phosphates of the galactose moiety of blocked Lewis$^a$ and Lewis$^x$ can also be made using compound 32 in the synthesis of these compound. This compound is made by direct benzoylation of both the 2,3-hydroxyl groups of compound 29. However, after deblocking, both the 2 and 3 hydroxyl groups of galactose are then available for sulfation and phosphorylation and the selectivity is not as efficient. Compound 29 can be converted to the 2,3-dibenzoyl protected compound 32 in a manner similar to that described above for the preparation of compound 31. In this case, 3–5 equivalents of benzoyl chloride are generally employed.

Compounds 31 and 32 are converted to compounds 33 and 32a (shown in FIGS. 5A and 5B) via known methodology (Norberg et al.[26]) using bromine tetraethylammonium bromide.

Alternatively, compound 31 can be converted to compound 34 by contacting compound 31 with 80% acetic acid/water at approximately 50° C. for about 1–2 hours. Compound 34 is then converted to compound 35 by treatment with acetic anhydride/pyridine in dichloromethane.

In another embodiment, compound 32 is treated with sodium cyanoborohydride and ceric chloride to provide for the benzyl-2,3-O-dibenzoyl-4-O-benzyl-β-D-thiogalactopyranoside (not shown). In turn, this compound is chloroacetylated at the 6-hydroxyl group. After formation of the Lewis$^x$ or Lewis$^a$ structures, the chloroacetyl group can be selectively removed (as described above) and then either phosphorylated or sulphonated so as to provide for the 6-phosphate or 6-sulfate derivative.

Thus, in another of its method aspects, the present invention relates to a method for the preparation of benzyl 4,6-di-O-benzylidene-2-O-benzoyl-3-O-chloroacetyl-β-D-thiogalactopyranoside which comprises the steps:

(a) contacting D-galactose with sodium acetate in dichloroethane maintained at a temperature of from about 75°–85° C. while adding dropwise at least 5 equivalents of acetic anhydride;

(b) maintaining the solution produced in step (a) above at about 75°–85° C. for a sufficient period of time so as to produce the 1,2,3,4,6-pentaacetylated derivative of D-galactose;

(c) reacting the product produced in step (b) above with at least one equivalent of benzyl mercaptan and about 1–3 equivalents of boron trifluoride etherate under conditions sufficient to provide the benzyl 2,3,4,6-tetra-O-acetyl-β-thiogalactopyranoside;

(d) removing the acetyl blocking groups by contacting the benzyl 2,3,4,6-tetra-O-acetyl-β-thiogalactopyranoside with sodium methoxide and methanol under conditions sufficient to provide for phenyl β-thiogalactopyranoside;

(e) contacting the benzyl β-thiogalactopyranoside produced in step (d) above with benzylaldehyde dimethyl acetal and p-toluenesulfonic acid under conditions sufficient to provide the benzyl 4,6-di-O-benzylidene-β-D-thiogalactopyranoside;

(f) adding chloroacetylchloride to a dimethylformamide (DMF) solution containing the benzyl 4,6-di-O-benzylidene-β-D-thiogalactopyranoside produced in step (e) above maintained at a temperature of from about –40° C. to about –15° C. for a sufficient period of time so as to provide benzyl 4,6-di-O-benzylidene-3-O-chloroacetyl-β-D-thiogalactopyranoside; and (g) adding benzoyl chloride or other suitable benzoylating agent to a solution of benzyl 4,6-di-O-benzylidene-3-O-chloroacetyl-β-D-thiogalactopyranoside in a suitable solvent containing a base and dimethylaminopyridine under conditions sufficient to provide for benzyl 4,6-di-O-benzylidene-2-O-benzoyl-3-O-chloroacetyl-β-D-thiogalactopyranoside.

2B. SYNTHESIS OF TYPE LEWIS$^x$ STRUCTURES [βGal(1→4) [αFuc(1→3)]βGlcNAc-OR]

Figure 4A:
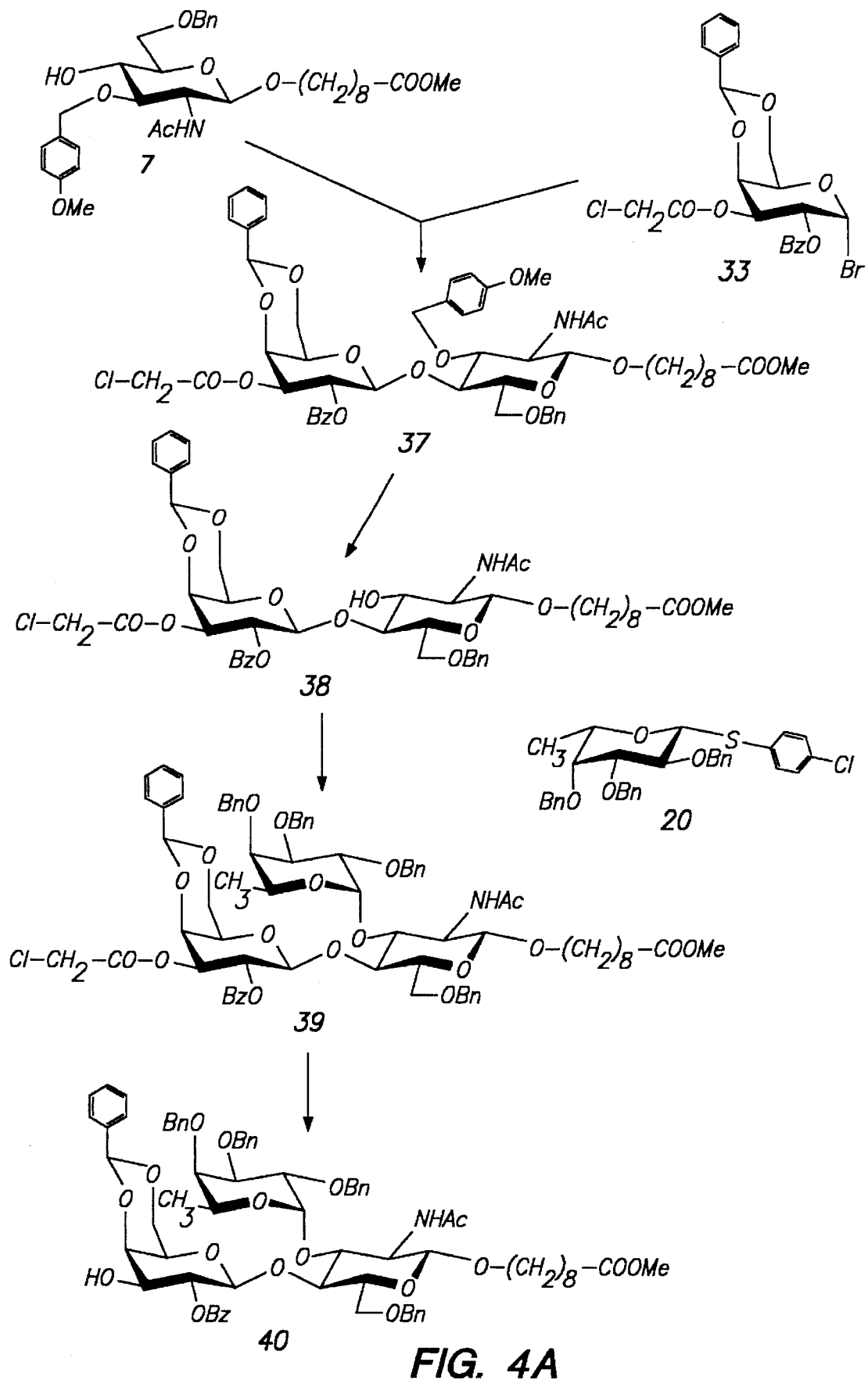
FIGS. 4A and 4B illustrates the synthesis of modified Lewis$^x$ compounds having a sulfate substituent in the 3 position of the galactose unit. In this scheme, the 2,3 positions of galactose are differentially blocked so that the 3-position can be selectively deblocked and then selectively converted to the sulfate substituent.
Figure 4B:
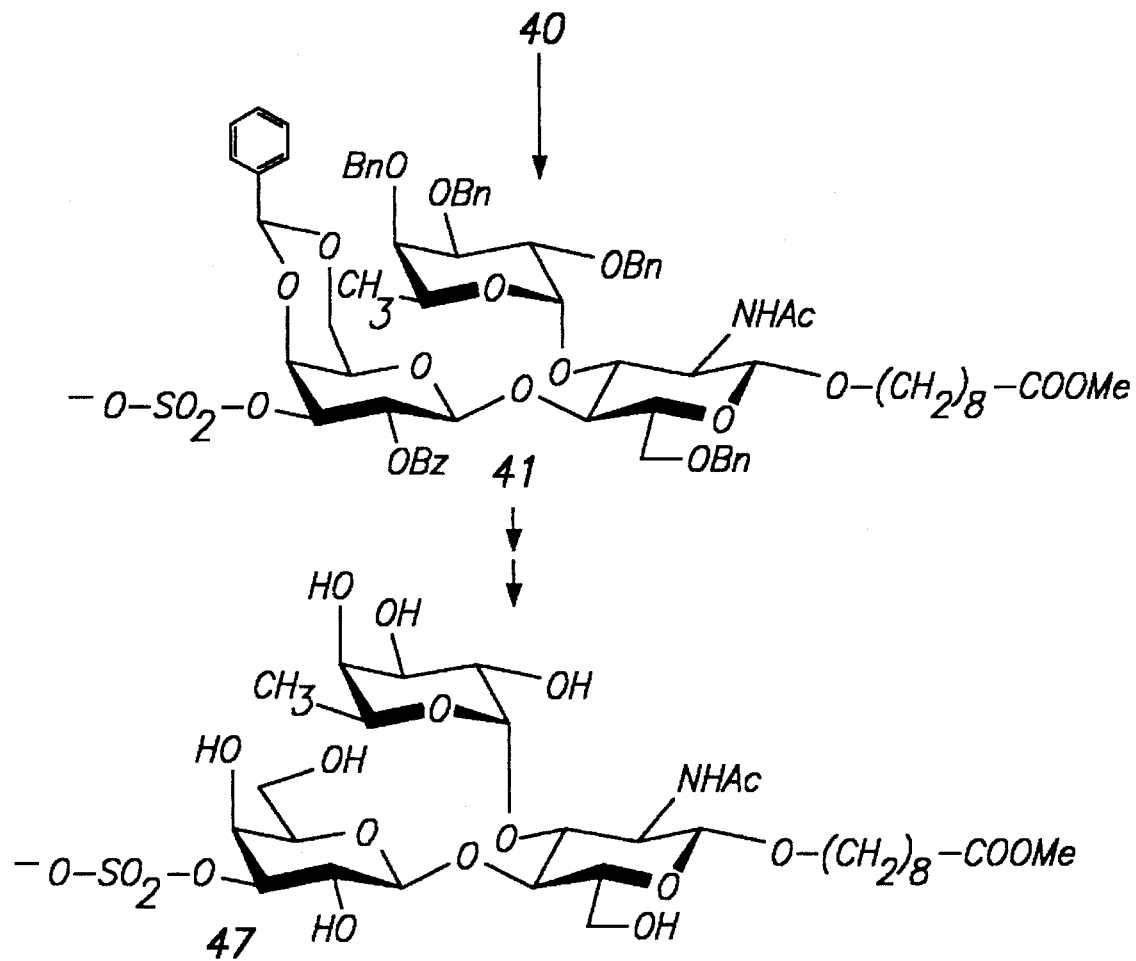

FIGS. 4A and 4B illustrates one method for synthesizing blocked type II backbones and conversion to blocked Lewis$^x$ structures. In this figure, the 2,3 hydroxyl groups of the galactose are differentially blocked so that at the appropriate point in the synthesis of Lewis$^x$ and Lewis$^a$ derivatives, the chloroacetyl protecting group at the 3-position of galactose is selectively removed and then converted to the sulfate, phosphate or —OCHR$_{18}$COOH group. Also, as noted above, the chloroacetyl protecting group can be selectively placed at the 6-position of the galactose and then selectively removed so as to allow for the formation of the sulfate, phosphate or —OCHR$_{18}$COOH group at the 6-position of galactose.

Specifically, in FIGS. 4A and 4B, compound 7 and compound 33 are combined to form compound 37. This is accomplished by dissolving compound 7 and approximately 1.5 equivalents of compound 33 in dichloromethane containing molecular sieves to which is added about 1 equivalent (based on compound 7) of 2,6-di-t-butyl-4-methylpyridine. The reaction is stirred for 30 minutes at room temperature and then cooled to –50° C. An anhydrous toluene solution containing approximately a slight excess (e.g., about 1.2 equivalents) of silver trifluoromethane sulfonate is then added to the solution and the reaction is allowed to warm to –15° C. over 2 hours and maintained at that temperature for an additional 5 hours.

At this time, the molecular sieves are removed by filtration by passing through celite and the recovered solution is quenched by addition to a saturated sodium bicarbonate solution. The organic extract is then washed with water, with aqueous 0.5N HCl, and then with water. The organic solution is then dried and concentrated in vacuo to provide a crude product of compound 37. This is then purified by conventional techniques such as column chromatography using silica gel and hexane-ethyl acetate (1:1) as the eluant.

To a dichloromethane solution containing compound 37 is added an excess of dichlorodicyanoquinone (DDQ) which selectively removes the p-methoxybenzyl protecting group to provide compound 38. This compound is fucosylated with an excess of compound 20 (about 1.3–1.5 equivalents) in dichloromethane containing mercuric bromide or cupric bromide and about 1–1.5 volume percent DMF to give blocked Lewis$^x$ compound 39. After work-up and chromatography compound 39 is treated with thiourea to remove the chloroacetyl group and the compound is sulfated with sulphur trioxide/pyridine complex in DMF at 0° C. for 2 hours to provide compound 41. The blocking groups on compound 41 are then removed by conventional techniques to provide for the Lewis$^x$ analogue having a sulfate group at the 3-position of the galactose unit.

Alternatively, compound 25 (or the 3-chloroacetyl analogue of compound 25 described above—not shown) can be used in place of compound 20 in the above synthesis. Removal of the chloroacetyl blocking groups on the 3-hydroxyl of the galactose and the 4-hydroxyl of the fucose provides an facile route to the preparation of a disulfated or diphosphorylated Lewis$^x$ derivatives.

In another embodiment, compound 40 can then be alkylated by first adding an appropriated base (e.g., silver oxide, barium hydroxide, sodium hydride) and then adding benzyl bromide acetate (BrCH$_2$COOBn) or other similar acetates (e.g., BrCHR$_{18}$, COOBn—where R$_{18}$, is alkyl of from 1 to 7 carbon atoms or —COOBn) to the reaction medium in an appropriate solvent such as DMF. After reaction completion, the benzyl ester(s) is (are) readily removed by conventional hydrogenation techniques which additionally removes the other benzyl protecting groups and the benzylidine protecting group. Treatment with sodium methoxide/methanol provides for a —OCH$_2$COOH (or —OCHR$_{18}$COOH where R$_{18}$ is alkyl of from 1 to 7 carbon atoms or —COOH) substituted to the 3-position of galactose. Similar type chemistry can be performed at the 6-hydroxyl group of the galactose or at the 4-hydroxyl group of the fucose by use of appropriate blocking groups.

In another embodiment, compound 40 can be treated by known methods[48] to provide for the 3-phosphate compound. Specifically, compound 40 can be treated with diphenylphosphorochloridate and 4-dimethylaminopyridine (1:1) in pyridine at 0° C. The solution is allowed to warm to room temperature over 0.5 hours and stirred for 15 hours. The resulting compound is then hydrogenated under conventional conditions (first with $H_2$ in EtOH with Pd on carbon for 15 hours and then with $H_2$ in EtOH with $PtO_2$ for 3 hours) to provide for the phosphate derivative at the 3-position of galactose. Further deprotection leads to the modified Lewis$^x$ compound having a phosphate substituent at the 3-position of galactose) which is purified and converted to its disodium salt by contacting a solution of this compound with a sodium form of Dowex 50×8.

As is apparent, the procedures set forth above can also be used to introduce a phosphate or a —$OCHR_{18}COOH$ group at the 6-position of galactose or a phosphate group on the fucose.

Figure 5A:
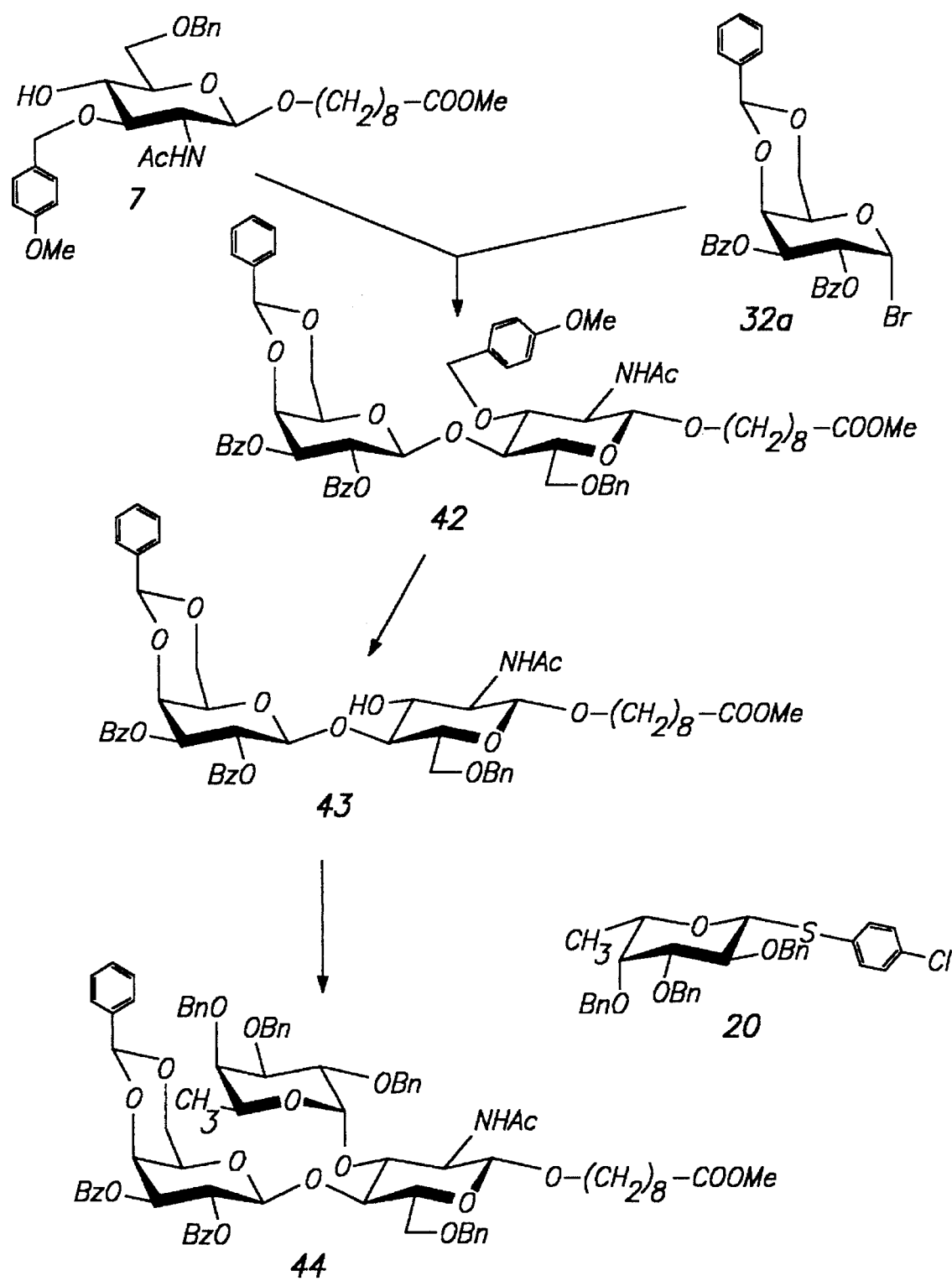
FIGS. 5A and 5B illustrates the synthesis of modified Lewis$^x$ compounds having a sulfate substituent in the 3 position of the galactose unit. In this scheme, 25 the 2,3 positions of galactose are not differentially blocked. Accordingly, deprotection of the 3-position of the galactose unit also results in deprotection of the 2-position and subsequent reaction to form the sulfate at the 3-position does not proceed with 100% yield but rather some of the product has a sulfate substituent at the 2-position of the galactose which is then separated by chromatography.
Figure 5B:
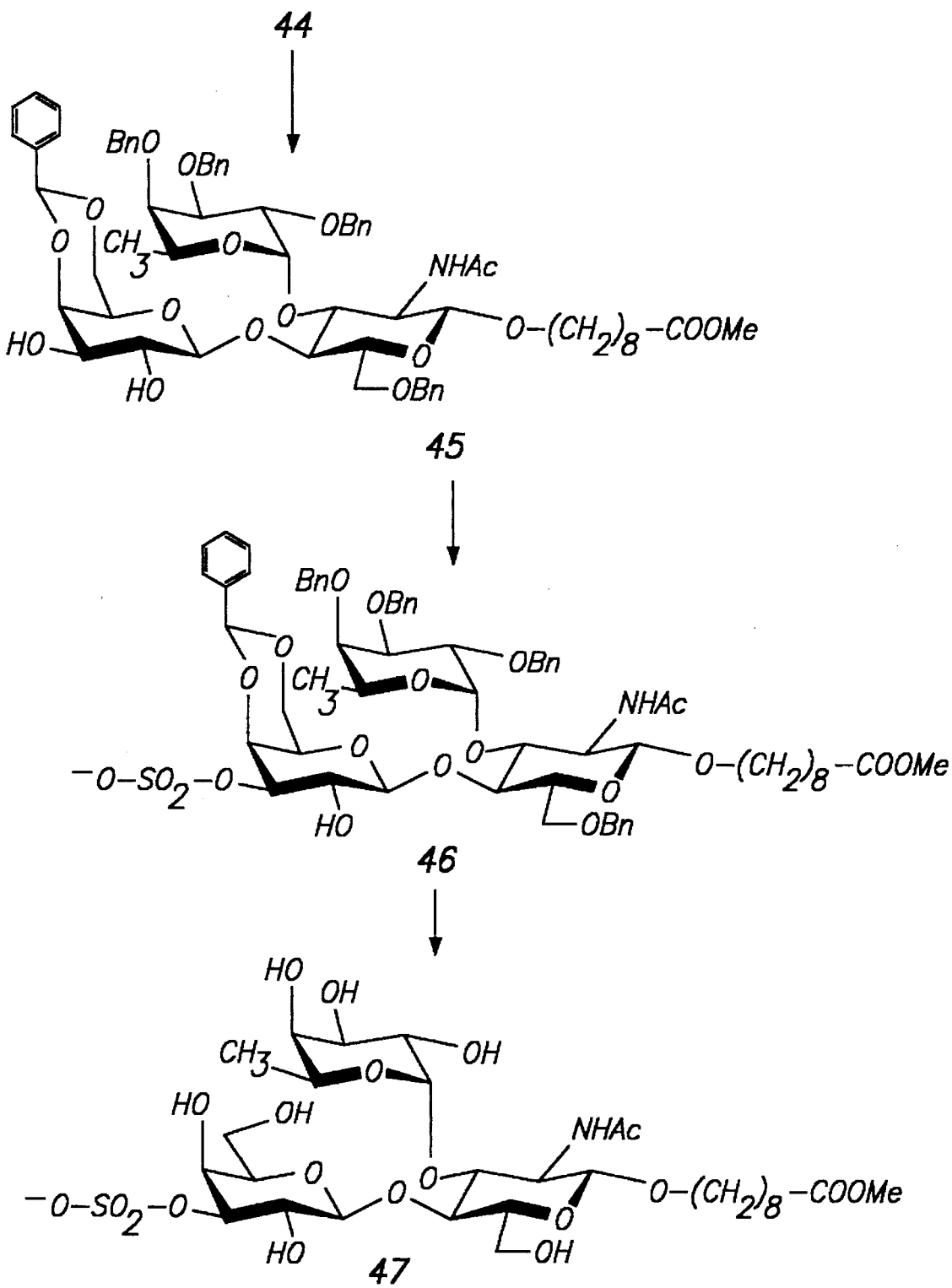

FIGS. 5A and 5B illustrates another method for synthesizing blocked type II backbones and conversion to blocked Lewis$^x$ structures. In this figure, the 2,3 hydroxyl groups of the galactose are not differentially blocked and, accordingly, while the resulting compound 45 (and the type I analogue) is useful for preparing the 3-sulfate (as part of a mixture with the 2-sulfate which can be purified by chromatography) it is not as versatile as the synthetic scheme set forth in FIGS. 4A and 4B.

In any event, in FIG. 5, compound 7 and approximately 1.6–1.7 equivalents of compound 32a are dissolved in dichloromethane containing molecular sieves to which is added about 1 equivalent (based on compound 7) of 2,6-di-t-butyl-4-methylpyridine. The reaction is stirred for 30 minutes at room temperature and then cooled to −50° C. An anhydrous toluene solution containing approximately a slight excess (e.g., about 1.2 equivalents) of silver trifluoromethane sulfonate is then added to the solution and the reaction was allowed to warm to −15° C. over 2 hours and maintained at that temperature for an additional 5 hours.

After reaction completion, the reaction system was worked up to provide a crude product of compound 42. This is then purified by conventional techniques such as column chromatography using silica gel and toluene-ethyl acetate (1:1) as the eluant.

To a dichloromethane solution containing compound 42 is added an excess of dichlorodicyanoquinone (DDQ) which selectively removes the p-methoxybenzyl protecting group to provide compound 43. This compound is fucosylated with an excess of compound 20 (about 1–3 equivalents and preferably about 1.3–1.5 equivalents) in dichloromethane containing mercuric bromide or cupric bromide and about 12 volume percent DMF to give blocked Lewis$^x$ compound 44. After work-up and chromatography compound 44 is treated with sodium methoxide/methanol to remove the benzoyl blocking groups at the 2,3-positions of the galactose so as to provide for compound 45. This compound is then sulphonated with sulphur trioxide/pyridine complex in DMF at 0° C. for 2 hours to provide compound 46. Compound 46 is produced as a mixture of the 3-sulfate and the 2-sulfate (or 2,3-disulfate) which is separated by chromatography (e.g., column chromatography on silica). Conventional deprotection of the removable protecting groups provides for the sulfate derivative at the 3-position of galactose for Lewis$^x$, compound 47, which can be passed onto an anion exchange resin (sodium form) to generate the sodium salt.

Additionally, lactose can be used in the methods of this invention in place LacNAc by merely a suitable blocking group at the 2-hydroxy of the glucose moiety of the lactose structure[49]. Differential blocking of the lactose provides for a composition having a selectively removable blocking group at the 3 and/or 6 position of the galactose. This compound is then selectively deblocked at the 3 and/or 6 position and then derivatized to the 3 and/or 6 sulfate, phosphate or —$OCHR_{18}COOH$. Afterwards, the remaining blocking groups are removed and the fucosyl unit added enzymatically (see below).

2C. SYNTHESIS OF LEWIS$^A$ STRUCTURES [βGal(1→3) [αFuc(1→4)]βGlcNAc-OR]

While FIGS. 4A and 4B and FIGS. 5A and 5B illustrate the synthesis of Lewis$^x$ structures, Lewis$^a$ structures are readily prepared in a similar manner, as illustrated in FIGS. 8A and 8B, using appropriately blocked GlcNAc-OR structures. The βGal(1→3)βGlcNAc-OR structures can be prepared, for example, from compounds 5 and 35. Specifically, compound 35 is first converted to the 1-α-bromo derivative via known methodology (Norberg et al.[26]) using bromine ($Br_2$) and tetraethylammonium bromide ($Et_4N^+Br^-$) at about 0° C. About 1.5 equivalents of this compound and compound 5 are dissolved in dichloromethane ($Cl_2CH_2$) containing molecular sieves to which is added about 1 equivalent (based on compound 5) of 2,6-di-t-butyl-4-methylpyridine. The reaction is stirred for 30 minutes at room temperature and then cooled to −50° C. An anhydrous toluene solution containing approximately a slight excess (e.g., about 1.2 equivalents) of silver trifluoromethane sulfonate (silver triflate) is then added to the solution and the reaction is allowed to warm to −15° C. over 2 hours and maintained at that temperature for an additional 5 hours. Afterwards, the solution is allowed to come to room temperature and stirred overnight.

At this time, pyridine and dichloromethane are added and the molecular sieves are removed by filtration by passing through celite and the recovered solution is quenched by addition to a saturated sodium bicarbonate solution. The organic extract is then washed with water, with aqueous 0.5N HCl, and then with water. The organic solution is then dried and concentrated in vacuo to provide a crude product which is then purified by conventional techniques such as column chromatography using silica gel and hexane-ethyl acetate (1:1) as the eluant to provide for compound 100. The benzylidine protecting group of compound 100 is then selectively removed by treatment with 80% acetic acid (AcOH) in water ($H_2O$) to provide for compound 101. Compound 101 is selectively acetylated at the 6-hydroxy group of the GlcNAc unit by treatment with acetic anhydride (AcOAc) in pyridine at about −20° C. to provide for compound 102. (i.e., 8-methoxycarbonyloctyl-2-acetamido-3(2-O-benzoyl-3-chloroacetyl-4,6-di-O-acetyl-β-D-galactopyranosyl)-6-O-acetyl-2-deoxy-β-D-glucopyranoside. This compound is then fucosylated in the manner similar to compound 38 as described above to provide for compound 103 and then deblocked and sulfated in the manner described above for compounds 40, 41, and 47 to provide for compounds 104, 105, and 106.

Alternatively, compound 32 is converted to the 1-α-bromo derivative via known methodology (Norberg et al.[26]) as described above and the resulting compound is then treated with sodium cyanoborohydride and ceric chloride to provide for the benzyl-2,3-O-dibenzoyl-4-O-benzyl-β-D-thiogalactopyranoside (not shown). In turn, this compound is chloroacetylated at the 6-hydroxyl group and then reacted with compound 5 in the manner described above to provide for the 8-methoxycarbonyloctyl-2-acetamido-3(4-O-benzoyl-6-chloroacetyl-2,3-di-O-benzoyl-β-D-galactopyranosyl)-6-O-acetyl-2-deoxy-β-D-glucopyranoside. This compound is then treated in the manner described above for compound 102 so as to provide for a Lewis$^a$ derivative having a sulfate at the 6-position of the galactose.

In yet another embodiment, both type I and type II structures can be made simultaneously by combining compound 15 and compound 33 under appropriate conditions well known in the art. For example, compound 15 and approximately 1.5 equivalents of compound 33 are added to dichloromethane containing molecular sieves to which is added about 1 equivalent (based on compound of 2,6-di-t-butyl-4-methylpyridine. The reaction is stirred for 30 minutes at room temperature and then cooled to −50° C. An anhydrous toluene solution containing approximately a slight excess (e.g., about 1.2 equivalents) of silver trifluoromethane sulfonate is then added to the solution and the reaction is allowed to warm to −15° C. over 2 hours and maintained at that temperature for an additional 5 hours. Afterwards, the solution is allowed to come to room temperature and stirred overnight.

At this time, pyridine and dichloromethane are added and the molecular sieves are removed by filtration by passing through celite and the recovered solution is quenched by addition to a saturated sodium bicarbonate solution. The organic extract is then washed with water, with aqueous 0.5N HCl, and then with water. The organic solution is then dried and concentrated in vacuo to provide a crude product which contains both the type I and type II structures which are separated and purified by conventional techniques such as column chromatography using silica gel and hexane-ethyl acetate (1:1) as the eluant.

The ratio of type I structure to type II structure resulting from this reaction can be improved by using the 2-NAc derivative of GlcNH$_2$ compound 15. This compound can be readily prepared by reacting compound 15 with hydrazine, acetylating the resulting product with acetic anhydride/pyridine and then deacetylating the 3,4-hydroxyl groups by treatment with sodium methoxide/methanol.

2D. ENZYMATIC REACTIONS

In addition to the chemical syntheses of the Lewis$^a$ and Lewis$^x$ analogues described above, the appropriately blocked type I [βGal(1→3)βGlcNAc-OR] and type II [βGal(1→4)βGlcNAc-OR] structures (e.g., compound 37) can be selectively deblocked to provide for a hydroxyl group at the 3-position of galactose (or at the 6-position) and then sulfonated, phosphorylated, or converted to —OCHR$_{18}$COOH (each of which are described above). The resulting compound is then totally deblocked and fucosylated by using, for example, βGal(1→¾)βGlcNAc α(1→¾) fucosyltransferase29. The enzymatic transfer of fucose onto the 4-position of GlcNAc to form Lewis$^a$ and to the 3-position of GlcNAc to form Lewis$^x$ structures requires the prior synthesis of its nucleotide (GDP) derivatives. Synthesis of GDP-fucose is preferably accomplished in the manner recited by Jiang et al.17 and which is exemplified in the examples hereunder.

GDP-fucose (GDP-Fuc) is then combined with the derivatized βGal(1→4)βGlcNAc-OR compound or the derivatized βGal(1→3)βGlcNAc-OR compound in the presence of a suitable fucosyltransferase (e.g., βGal(1→¾)βGlcNAc α(1→¾)fucosyltransferase) under conditions wherein fucose is transferred to the 3 position of GlcNAc of the derivatized βGal(1→4)βGlcNAc-OR or the 4-position of the derivatized βGal(1→3)βGlcNAc-OR compound to form a Lewis$^x$ or Lewis$^a$ structures respectively.

Suitable fucosylations conditions, known in the art, include the addition of the fucosyltransferase to a mixture of the derivatized βGal(1→4)βGlcNAc-OR (or alternatively the derivatized βGal(1→3)βGlcNAc-OR compound) and the GDP-fucose in a appropriate buffer such as 50 mM sodium cacodylate in appropriate conditions of pH and temperature such as at a pH of 6.5 and a temperature between 30° and 45° C., preferably 35° to 40° C. while incubating for about 12 hours to 4 days. The resulting fucosylated product can be isolated and purified using conventional methodology comprising HPLC, ion exchange-, gel-, reverse-phase- or adsorption chromatography.

It is also contemplated that the deblocked type I and II structures can be sulfated by use of an appropriate sulfotransferase.

2E. MODIFICATION ON THE 2 AND/OR 6 POSITIONS OF GlcNAc

FIGS. 6A and 6B and FIGS. 7A and 7B illustrate two different syntheses for the retention of the 2-amino substituent on the glucosamine (i.e., a derivative of βGal(1→3)βGlcNAc-OR or βGal(1→4)βGlcNAc-OR where the NAc group of GlcNAc has been converted to an amine). As shown below, the retention of the amino group on the glucosamine unit allows for the facile preparation of different 2-substituted derivatives.

In FIGS. 6A and 6B, compounds 1, 13, 14, and 15 are prepared in the manner described above and illustrated in FIGS. 6A and 6B. Likewise, 1-α-bromo-2,3,4,6-tetracetyl-galactose is prepared by first forming the peracetylated derivative of galactose, compound 26. Compound 26 is then converted to the 1-α-bromo derivative via known methodology (HBr/Acetic acid—at about 0° C. to 20° C.) so as to provide for 1-α-bromo-2,3,4,6-tetracetylated galactose.

The 1-α-bromo-2,3,4,6-tetracetylated galactose (about 1.2 to about 1.5 equivalents) is added dropwise to a solution of compound 15 in dichloromethane at about −50° C. in the presence of excess calcium sulfate, about 4 equivalents of silver carbonate and about 0.5 equivalents of silver triflate. The reaction is then allowed to warm to −30° C. and maintained there for about 1–3 days. The reaction is then quenched by the addition of methanol, warmed to room temperature, and filtered through celite. The filtrate is washed with aqueous sodium bicarbonate and aqueous ethylene diamine tetraacetic acid (EDTA). The recovered solution is dried and then stripped in vacuo to provide a crude product containing both the type I structure (not shown) and the type II structure (compound 48). The residue is chromatographed on a silica gel column eluted with toluene:acetone:methanol (20:3:1) to give compound 48 as well as the type I analogue (not shown).

For convenience sake, further reactions are shown on compound 48, it being understood however, that the same reactions could be conducted on the type I analogue to provide modified Lewis$^a$ compounds.

Compound 20 is then reacted with one equivalent of bromine in dichloromethane at −20° C. for about 1 hour to provide for the 1-α-bromo derivative of compound 20. The solution is then quenched with a cold aqueous sodium bicarbonate solution. The organic solution is dried and concentrated to approximately half the original volume in vacuo at room temperature. About 2 equivalents of this compound are then add to a dichloromethane solution of compound 48 that contains about 2 equivalents of mercuric bromide (HgBr$_2$), molecular sieves and tetraethylammonium bromide. The reaction is stirred at room temperature for approximately 48 hours and the solution is filtered through celite and the filtrate washed with water, a 5% EDTA solution, saturated aqueous sodium bicarbonate, and then water. The organic layer is then dried and the solvent removed in vacuo to provide for compound 49 which is purified by chromatography on silica gel.

Compound 49 is converted to compound 50 by conventional Zemplen conditions and compound 50 is then converted to compound 51 by conventional methodology (e.g., benzaldehyde dimethylacetal, DMF, pTSA). In turn, compound 51 is treated with hydrazine acetate in methanol at room temperature for about 1–5 hours to provide for compound 52 which is converted to compound 53 by contacting with trifluoroacetic anhydride in methanol. Alternatively, compound 52 serves as a convenient point in the synthesis to convert this amine to an amide, a carbamate, an urea, a $-NHSO_3H$ group, etc. in the manner described below.

Compound 53 can then be sulfated in the same manner as described above for compound 45. Alternatively, compound 53 can be differentially blocked at the 2,3 hydroxyl groups of the galactose in the same set forth above for compounds 29–31 so as to provide for compounds 54 and 55. In turn, compound 55 is selectively deblocked with thiourea to provide for compound 56 in the same manner described above for compound 39 (to provide compound 40). Compound 56 is then selectively sulfated in the manner described above to provide for compound 57. Alternatively, compound 56 can be converted to the 3-phosphate group on the galactose by reaction with diphenylphosphorochloridate and 4-dimethylaminopyridine (1:1) in pyridine at 0° C. The solution is allowed to warm to room temperature over 0.5 hours and stirred for 15 hours. The resulting compound is then hydrogenated under conventional conditions (first with $H_2$ in EtOH with Pd on carbon for 15 hours and then with $H_2$ in EtOH with $PtO_2$ for 3 hours) to provide for the phosphate derivative at the 3-position of galactose. Further deprotection leads to the modified Lewis$^x$ compound having a phosphate substituent at the 3-position of galactose) which is purified and converted to its disodium salt by contacting a solution of this compound with a sodium form of Dowex 50×8. Compound 56 can also be converted to the $-CHR_{18}COOH$ in the manner described above.

Lastly, compound 57 is deblocked by conventional techniques to provide for compound 60 which is a Lewis$^x$ analogue having a 2-amino glucose saccharide unit instead of a GlcNAc saccharide and further having a sulfate at the 3-position of the galactose saccharide unit.

Figure 6A:
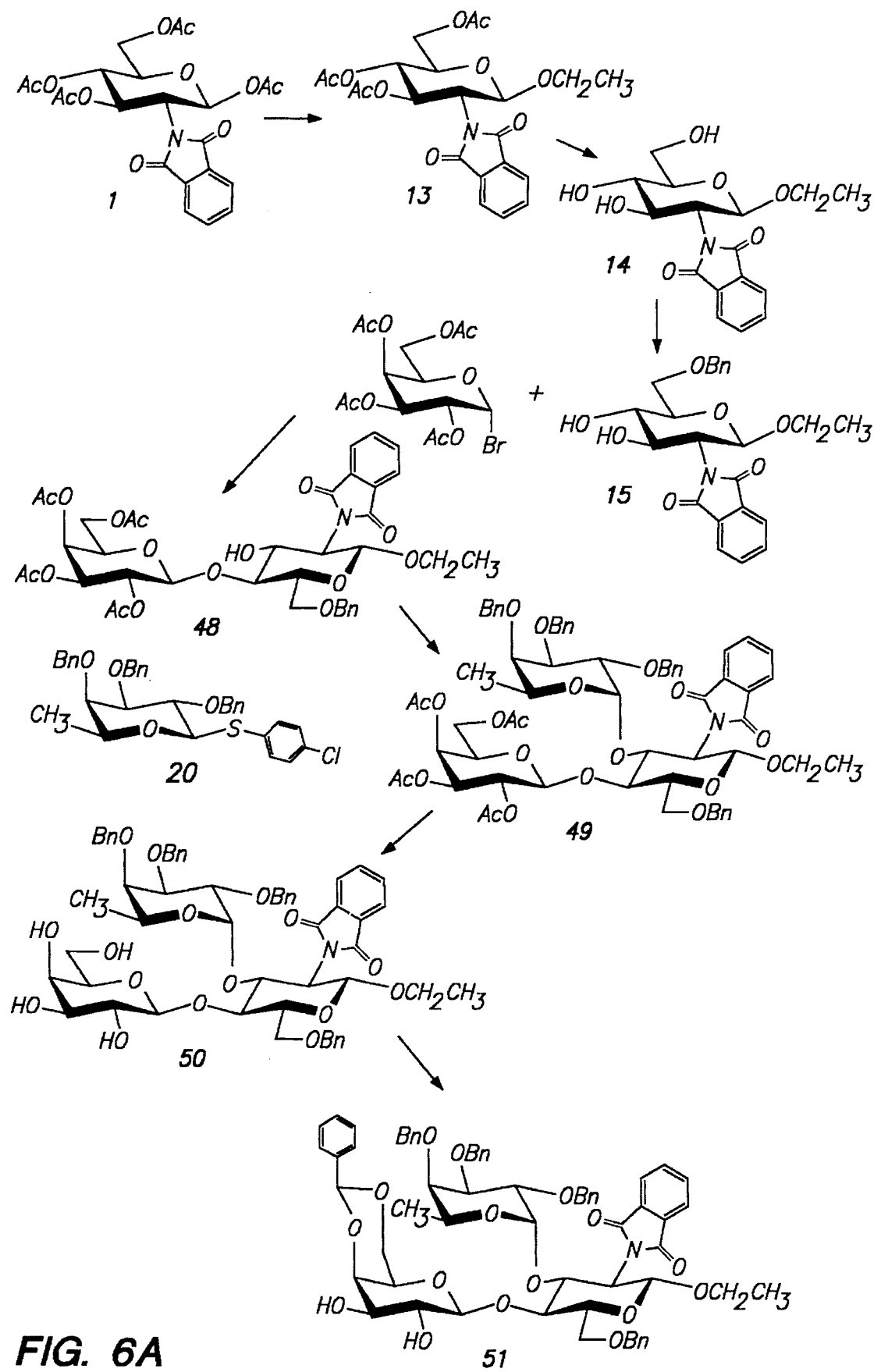
FIGS. 6A and 6B illustrates the synthesis of modified Lewis$^x$ derivatives bearing a sulfate substituent at the 3-position of the galactose and which utilize a 6-benzyl and 2-N-phthaloyl blocked glucosamine which can be later deblocked to provide for a glucosamine derivative.
Figure 6B:
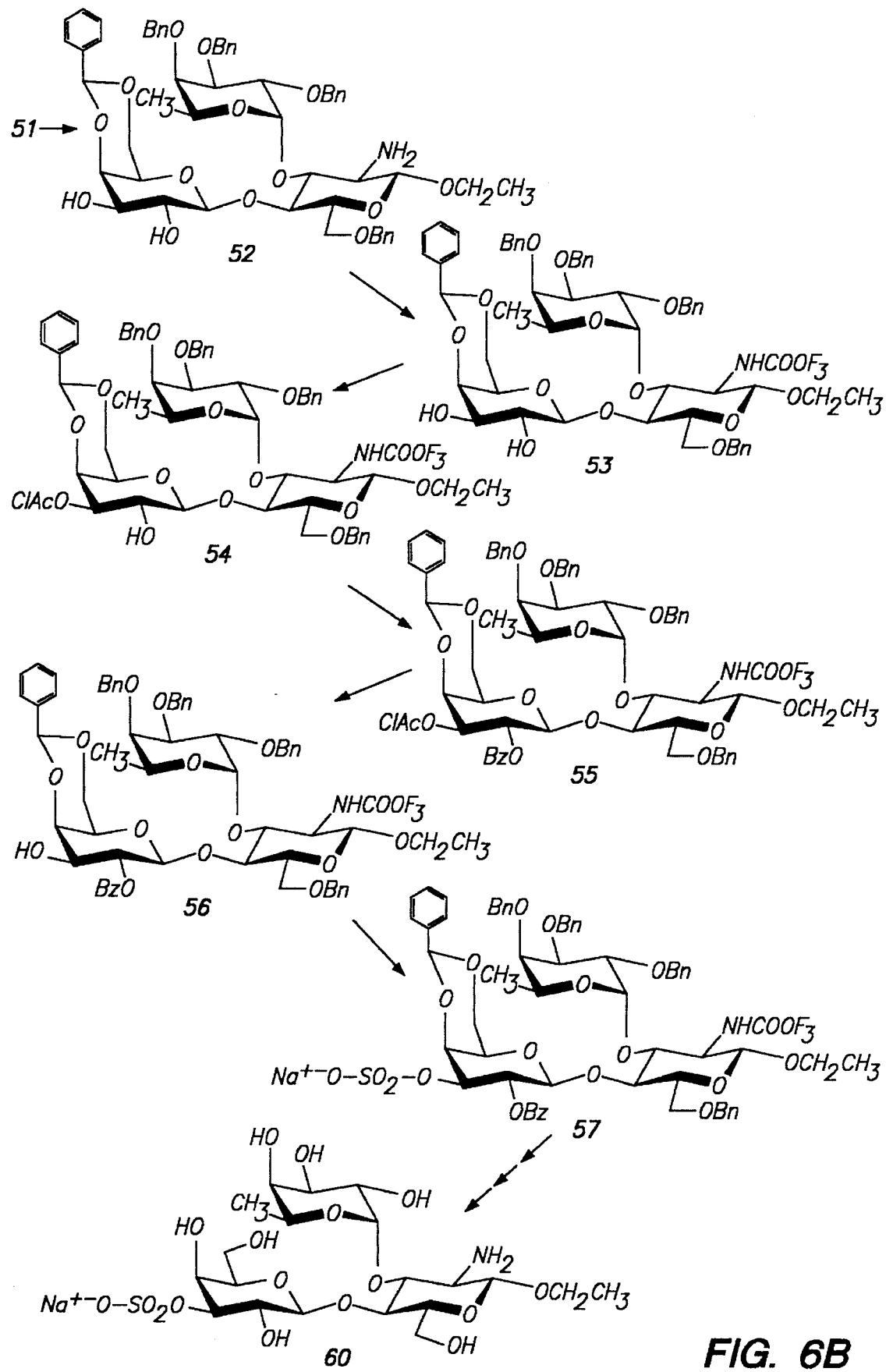

FIGS. 7A and 7B parallels somewhat the chemistry depicted in FIGS. 6A and 6B but, because the 3-hydroxyl group of the GlcNH$_2$ derivative is blocked (compound 69), this synthesis results only in type II structures. In particular, in FIG. 7, compound 13 is prepared by the methods described above. This compound is then deacetylated by conventional techniques (sodium methoxide/methanol) to provide for compound 14 which is then benzylidenated under conventional techniques to provide compound 66. Compound 66 is then treated with benzyl chloride and sodium hydride in dimethylformamide at about −20° C. to 20° C. to provide for compound 67. The benzylidine group of compound 67 is then removed with 80% aqueous acetic acid at about 80° C. for about 1–4 hours to provide for compound 68. This compound is then selectively acetylated at the 6-position by use of approximately equimolar amounts of acetyl chloride/pyridine in dichloromethane at about −10° C. to provide for compound 69. Approximately 1.2–1.5 equivalents of the 1-α-bromo-2,3,4,6-tetraacetylated galactose (described above) is added dropwise to a solution of compound 69 in dichloromethane maintained at about −30° C. in the presence of about 1.3 equivalents of 2,6,-di-t-butyl-4-methyl-pyridine and about 1.3 equivalents of silver triflate. The reaction is then maintained at −30° C. for 1 hour and then allowed to warm to 5° C. and maintained there for about 2 hours. The reaction is then quenched by the addition of methanol, warmed to room temperature, and filtered through celite. The filtrate is washed with aqueous sodium bicarbonate. The recovered solution is dried and then stripped in vacuo to provide a crude product containing compound 70 which is purified by chromatography on a silica gel column eluted with ethyl acetate:hexanes (1:2) to give compound 70.

The benzyl protecting group is then removed by hydrogenolysis ($H_2$/Pd on C) to provide for compound 71. Compound 71, in turn, is fucosylated in the same manner as described above for compound 48 (to provide for compound 49 as illustrated in FIGS. 6A and 6B) so as to provide for compound 72. Compound 72 is deacetylated by conventional techniques described above to provide for compound 73. Compound 73 is then converted to compound 74 by conventional methodology (e.g., benzaldehyde dimethylacetal, DMF, pTSA), followed by selective acetylation at the 6-position of the partially protected GlcNH$_2$ derivative by an approximately equivalent amount of acetyl chloride/pyridine in dichloromethane maintained at about −50° to about −20° C.). Compound 74 is then converted to compound 79 in the same manner (described above) as compound 53 was treated to provide for compound 60.

Alternatively, the free hydroxyl groups of compound 74 can be acetylated with acetyl chloride/pyridine in the manner described above and the benzylidine group selectively opened by sodium cyanoborohydride and ceric or aluminum chloride to give the 2,3-diacetyl-4-benzyl-6-hydroxy derivative on the galactose moiety (not shown). This compound is then functionalized at the 6-position of the galactose so as to contain a sulfate, phosphate or $-CHR_{18}COOH$ group at this position.

In addition to the above, the 2,6 positions of the GlcNAc unit can be modified prior to coupling so as to provide for type I and type II structures modified at these positions which are then further modified in the manner described above to prepare the sulfated, phosphorylated or $-CHR_{18}COOH$ substituted Lewis$^a$ and Lewis$^x$ structures. As shown by Venot et al., U.S. patent application Ser. No. 07/887,747, filed May 22, 1992 as Attorney Docket No. 000475-011 and entitled "MODIFIED SIALYL LEWIS$^A$ COMPOUNDS" and by Venot et al., U.S. patent application Ser. No. 07/887,746, filed May 22, 1992 as Attorney Docket No. 000475-029 and entitled "MODIFIED SIALYL LEWIS$^X$ COMPOUNDS" modification at the 2 and/or 6-positions of the GlcNAc moiety of type I structures [βGal(1→3)βGlcNAc-OR] and on type II structures [βGal(1→3)βGlcNAc-OR—LacNAc-OR] still permit the use of the βGal(1→¾)βGlcNAc α(1→¾)fucosyltransferase on the deblocked compound. The disclosures of both of these applications are incorporated herein by reference in their entirety.

i. Modification at the 2-position of GlcNAc

Modification at the 2-position of GlcNAc can be accomplished by a variety of ways. For example, the known[8] 2-azido-2-deoxy-glucose-OR compound (prepared, for example, by azidonitration of 4,5,6-triacetylglucal) can be protected at the 6 position with a removable protecting group (i.e., Si(C$_6$H$_5$)$_2$tBu) by conventional techniques[8] and then combined with an appropriate blocked galactose compound in the manner described above to provide a mixture of blocked βGal(1→3)GlcN$_3$-OR and βGal(1→4)GlcN$_3$-

OR derivatives which are readily separated by conventional techniques.

At the appropriate time during synthesis of the Lewis$^a$ or Lewis$^x$ structures, the azido group is reduced to an amino group which can be protected as N-trifluoroacetamido. In turn, the trifluoroacetamido group is removed at the appropriate point in the synthesis thereby unmasking the amino group.

The amino group can also be derivatized by conventional methods to provide for —$NR_{11}C(O)R_{10}$, —$N=C(R_{11})_2$, —$NHCH((R_{11})_2$, —$NHR_{12}$, and —$N(R_{12})_2$ groups by conventional methods. For example, the —$NH_2$ group can be reacted, using conventional techniques, with:

- a carboxylic acid, anhydride or chloride to provide for amides. Alternatively, the desired acid can be activated, as reported by Inazu et al[37] and then reacted with the amino group. The carboxylic acid, anhydride, chloride, or activated acid is selected so as to provide for an $R_{10}$ group (i.e., as part of the —$NR_{11}C(O)R_{10}$ substituent) which is hydrogen or alkyl of from 1 to 4 carbon atoms,

- with an aldehyde or ketone (of from 1 to 4 carbon atoms) at controlled pH to form an imine [—$N=C(R_{11})_2$] which upon reduction (e.g., with sodium cyanoborohydride) provides for an alkylamine substituent [i.e., —$NHCH(R_{11})_2$] as reported by Bernotas et al.[38],

- with a cyclic carbonate such as ethylene carbonate or propylene carbonate which ring opens upon reaction with the amine to form a carbamate group having an HO-alkylene-OC(O)NH— substituent where alkylene is from 2 to 4 carbon atoms as reported by Wollenberg et al.[39], U.S. Pat. No. 4,612,132,

- with a chloroformate [i.e., ClC(O)$OR_{13}$] in the manner disclosed by Greig et al.[40]. In this case, the chloroformate has an $R_{13}$ group which is alkyl of from 1 to 4 carbon atoms,

- with O=C(O—$C_6H_4$—$pNO_2$)$_2$ which leads to an activated intermediate which is then reacted with an amine (HN$R_{14}R_{15}$) to provide for ureas [—NHC(O)N$R_{14}R_{15}$] as described by Piekarska-Bartoszewicz et al.[41],

- with trimethylamine, sulfur trioxide (SO$_3$) so as to form the —NHSO$_3$H group as described by Petitou[42], and

- with derivatized formic acid or other materials to form a formamide (—NH—CHO)[43] which can be further functionalized to the isocyano (—N=C=O) and reduced to the deoxy derivative by tributyltin hydride (Bu$_3$SnH)[43].

Alternatively, the 2-deoxy (R$_2$=H) and 2-alkoxy glucose derivatives [i.e., derivatives of GlcNAc where the NAc has been replaced by —H (deoxy) or by an —$OR_{12}$(alkoxy)] are prepared using a synthetic scheme similar to that recited by Trumtez et al.[43] Specifically, the known 3,4,6-triacylated 1,2-ortho ester of glucose is deacylated under conventional conditions to give the 1,2-ortho ester of glucose. This compound is then converted to the 3,4,6-tribenzyl 1,2-ortho ester of glucose using conventional techniques. The 1,2-ortho ester of the resulting compound is then opened by conventional techniques to provide a protected glycosyl donor such as the 1 α-bromo-2-acetyl-3,4,6-tribenzyl derivative of glucose. This 1 α-bromo derivative is then converted to the glycoside (—OR) by conventional techniques and the 2-acetyl group is then removed. The 2-position is now ready for formation of the 2-deoxy by conventional methods such as first treating with carbon disulfide and methyl iodide in the presence of one equivalent of a base to form the —C(S)SCH$_3$ derivative, followed by reaction with tributyltin hydride) or for the preparation of the 2-alkoxy. The remaining protecting groups are removed so as to provide for 2-deoxy-glucose glycoside or a 2-alkoxy-glucose glycoside which can then be derivatized in the manner described above and illustrated in FIGS. 1A and 1B without the need to form the aglycon.

ii. Modification at the 6-Position of GlcNAc

The 6-deoxy derivative of GlcNAc-OR is synthesized from a known benzylidene ring blocked saccharide (8-methoxycarbonyloctyl-2-acetamido-4,6-O-benzylidene-2-deoxy-β-D-glucopyranoside)[44] which is protected at the 3-hydroxy position with a removable benzoyl blocking group (Bz) by reaction with benzoic anhydride in pyridine. Further conversion of this compound by reaction with N-bromosuccinimide and barium carbonate in carbon tetrachloride (CCl$_4$) at 65° C. leads to the 3,4-dibenzoyl-6-bromo-GlcNAc-OR compound. This compound is, in turn, converted to the 3,4-dibenzyl-6-deoxy-GlcNAc-OR by reaction with (C$_4$H$_9$)$_3$SnH in the presence of AIBN (azo bis-isobutyronitrile) at 110° C. followed by treatment with methanol/sodium methoxide. This compound can then be deprotected by conventional techniques to provide for the 6-deoxyGlcNAc-OR glycoside which can then be derivatized in the manner described above and illustrated in FIGS. 1A and 1B without the need to form the aglycon.

The 6-azido derivatives of GlcNAc-OR can be prepared in the manner described in FIG. 9. Specifically, GlcNAc-OR, compound 140, is converted to the p-methoxybenzylidine blocked compound 141 by reaction with (CH$_3$O)$_2$CH—$C_6H_4$—p—OCH$_3$. This compound is then protected at the 3-hydroxyl position by reaction with 4-CH$_3$O—$C_6H_4$—CH$_2$Br to provide for compound 142 where X' is 4-CH$_3$O—$C_6H_4$—CH$_2$—. Compound 142 is partially deprotected at the 4 and 6 positions by reaction with acetic acid (AcOH) in water at about 45° C. to provide for compound 143. The 6-mesylate, compound 144, is prepared by reacting compound 143 with mesyl chloride in pyridine (MsCl/py). The 6-azido derivative, compound 145, is then formed by reaction with sodium azide in dimethylformamide (DMF) and removal of the 3-blocking group with dichlorodicyanoquinone (DDQ) yields compound 146.

The 6-mesyl compound 144 can also be derivatized to any of a number of 6-substituents including alkoxy substituents, and the like by well known chemistry.

The 6-azido compound 145 can be derivatized to the 6-amino at an appropriate point in the synthesis of the Lewis$^a$ or Lewis$^x$ analogues in the manner described above. The 6-amino derivative can then be further functionalized by conventional methods to provide for —$NR_5C(O)R_4$, —NHSO$_3$H, —$N=C(R_5)_2$, —$NHCH(R_5)_2$, —$NHR_6$ and —$N(R_6)_2$. For example, the —$NH_2$ group can be reacted, using conventional techniques, with:

- a carboxylic acid, anhydride or chloride to provide for amides. Alternatively, the desired acid can be activated, as reported by Inazu et al[37] and then reacted with the amino group. The carboxylic acid, anhydride, chloride, or activated acid is selected so as to provide for an $R_4$ group (i.e., as part of the —$NR_5C(O)R_4$ substituent) which is hydrogen or alkyl of from 1 to 4 carbon atoms,

- with an aldehyde or ketone (of from 1 to 4 carbon atoms) at controlled pH to form an imine [—$N=C(R_5)_2$] which upon reduction (e.g., with sodium cyanoborohydride) provides for an alkylamine substituent [i.e., —$NHCH(R_5)_2$] as reported by Bernotas et al.[38],

- with a cyclic carbonate such as ethylene carbonate or propylene carbonate which ring opens upon reaction with the amine to form a carbamate group having an HO-alkylene-OC(O)NH— substituent where alkylene is from 2 to 4 carbon atoms as reported by Wollenberg et al.[39], U.S. Pat. No. 4,612,132, with a chloroformate [i.e., ClC(O)OR$_7$] in the manner disclosed by Greig et al.[40]. In this case, the chloroformate has an R$_7$ group which is alkyl of from 1 to 4 carbon atoms, with O=C(O—C$_6$H$_4$—pNO$_2$)$_2$ which leads to an activated intermediate which is then reacted with an amine (HNR$_8$R$_9$) to provide for ureas [—NHC(O)NR$_8$R$_9$] as described by Piekarska-Bartoszewicz et al.[41], with trimethylamine, sulfur trioxide (SO$_3$) at pH 9.5 so as to form the —NHSO$_3$H group as described by Petitou[42], and with derivatized formic acid or other materials to form a formamide (—NH—CHO)[43] which can be further functionalized to the isocyano (—N=C=O) and reduced to the deoxy derivative by tributyltin hydride (Bu$_3$SnH)[43].

The 6-alkoxy derivatives of GlcNAc can be prepared in the manner described in FIG. 10. Specifically, GlcNAc-OR, compound 140, is reacted with C$_6$H$_5$CH(OCH$_3$)$_2$ in an acidic medium in acetonitrile to provide for the 4,6-diprotected benzylidine compound 147. In turn, compound 147 can be reacted with benzyl (Bn) bromide and sodium hydride in the presence of dimethylformamide at around 0° C. to provide for a benzyl protecting group at the 3-position, i.e., compound 148. Deprotection at the 4,6 positions by contacting compound 148 with acetic acid and water at about 80°–90° C. provides for compound 149. Reaction of compound 149 with dibutyltin oxide [(Bu)$_2$SnO] and R$_6$Br provides for the 6-alkoxy compound 150. Conventional deprotection of the benzyl group with hydrogen in palladium/carbon yields compound 151.

In another embodiment, compound 147 can be reacted with [C$_6$H$_5$C(O)]$_2$O in pyridine to provide for a benzoyl protecting group (Bz) at the 3-position, i.e., compound 152. Reaction of compound 152 with N-bromosuccinimide in carbon tetrachloride yields the 6-bromo compound 153. Compound 153 can be reacted with tributyltin hydride [(Bu)$_3$SnH] in toluene to provide for the 6-deoxy compound 155 which after conventional deprotection of the benzoyl groups with sodium methoxide in methanol gives the 6-deoxy compound 156.

The 6-SR$_6$ compounds are prepared from the 6-mesyl derivative, compound 144, by reaction with potassium thioacetate, CH$_3$C(O)S$^-$K$^+$, to give the thioacetate derivative at the 6-position. This derivative is then treated with mild base to produce the 6-SH derivative. The 6-SH can be reacted with an alkyl halide (e.g., CH$_3$Br) to provide the —SR$_6$ derivatives which, in turn, can be partially or fully oxidized to the 6-sulfone or the 6-sulfoxide derivatives, —S(O)R$_6$ and —S(O)$_2$R$_6$ where R$_6$ is alkyl of from 1 to 4 carbon atoms.

C. Utility

Without being limited to any theory, it is believed that the modified Lewis$^x$ and Lewis$^a$ glycosides disclosed herein affect the cell mediated immune response in a number of ways. Specifically, these compounds can inhibit the ability of the immune response to become educated about a specific antigen when the compound is administered simultaneously with the first exposure of the immune system to the antigen. Also, the modified Lewis$^x$ and Lewis$^a$ glycosides disclosed herein can inhibit the effector phase of a cell-mediated immune response (e.g., the inflammatory component of a DTH response) when administered after second or later exposures of the immune system to the same antigen. Additionally, the modified Lewis$^x$ and Lewis$^a$ glycosides disclosed herein can induce tolerance to antigens when administered at the time of second or later exposures of the immune system to the antigen.

The suppression of the inflammatory component of the immune response by the modified Lewis$^x$ and Lewis$^a$ glycosides disclosed herein is believed to require the initiation of a secondary immune response (i.e., a response to a second exposure to antigen). The modified Lewis$^x$ and Lewis$^a$ glycoside is generally administered to the patient at least about 0.5 hours after an inflammatory episode, preferably, at least about 1 hour after, and most preferably, at least about 5 hours after an inflammatory episode or exacerbation.

The modified Lewis$^x$ and Lewis$^a$ glycosides disclosed herein are effective in suppressing cell-mediated immune responses to an antigen (e.g. the inflammatory component of a DTH response) when administered at a dosage range of from about 0.5 mg to about 50 mg/kg of body weight, and preferably from about 0.5 to about 5 mg/kg of body weight. The specific dose employed is regulated by the particular cell-mediated immune response being treated as well as by the judgment of the attending clinician depending upon factors such as the severity of the adverse immune response, the age and general condition of the patient, and the like. The modified Lewis$^x$ or Lewis$^a$ analogue is generally administered parenterally, such as intranasally, intrapulmonarily, transdermally and intravenously, although other forms of administration are contemplated. Preferably, the suppression of a cell-mediated immune response, e.g. the inflammatory component of a DTH response, is reduced by at least about 10% as opposed to control measured 24 hours after administration of the challenge to the mammal and 19 hours after administration of the modified Lewis$^x$ or Lewis$^a$ glycoside as per this invention.

In addition to providing suppression of the inflammatory component of the cell-mediated immune response to an antigen, administration of the modified Lewis$^x$ and Lewis$^a$ glycosides disclosed herein also imparts a tolerance to additional challenges from the same antigen. In this regard, re-challenge by the same antigen weeks after administration of the modified Lewis$^x$ or Lewis$^a$ glycoside results in a significantly reduced immune response.

Administration of the modified Lewis$^x$ and Lewis$^a$ glycosides disclosed herein simultaneously with first exposure to an antigen imparts suppression of a cell-mediated immune response to the antigen and tolerance to future challenges with that antigen. In this regard the term "reducing sensitization" means that the modified Lewis$^x$ or Lewis$^a$ glycoside, when administered to a mammal in an effective amount along with a sufficient amount of antigen to induce an immune response, reduces the ability of the immune system of the mammal to become educated and thus sensitized to the antigen administered at the same time as the modified Lewis$^x$ or Lewis$^a$ glycoside compound. An "effective amount" of this compound is that amount which will reduce sensitization (immunological education) of a mammal, including humans, to an antigen administered simultaneously as determined by a reduction in a cell-mediated response to the antigen such as DTH responses as tested by the footpad challenge test. Preferably the reduction in sensitization will be at least about 20% and more preferably at least about 30% or more. Generally, modified Lewis$^x$ and Lewis$^a$ glycoside compounds related to blood group determinants are effective in reducing sensitization when administered at a dosage range of from about 0.5 mg to about 50 mg/kg of body weight, and preferably from about 0.5 mg to about 5 mg/kg of body weight. The specific dose employed is regulated by the sensitization being treated as well as the judgement of the attending clinician depending upon the age and general condition of the patient and the like. "Simultaneous" administration of the compound with the antigen with regard to inhibiting sensitization means that the compound is administered once or continuously throughout a period of time within 3 hours of the administration of an antigen, more preferably the compound is administered within 1 hour of the antigen.

The methods of this invention are generally achieved by use of a pharmaceutical composition suitable for use in the parenteral administration of an effective amount of an oligosaccharide glycoside related to a blood group determinant. These compositions comprise a pharmaceutically inert carrier such as water, buffered saline, etc. and an effective amount of a modified Lewis$^x$ or Lewis$^a$ glycoside compound so as to provide the above-noted dosage of the oligosaccharide glycoside when administered to a patient. It is contemplated that suitable pharmaceutical compositions can additionally contain optional components such as an adjuvant, a preservative, etc.

It is also contemplated that other suitable pharmaceutical compositions can include oral compositions, transdermal compositions or bandages etc., which are well known in the art.

The following examples are offered to illustrate this invention and are not to be construed in any way as limiting the scope of this invention. Unless otherwise stated, all temperatures are in degrees Celsius. Also, in these examples, unless otherwise defined below, the abbreviations employed have their generally accepted meaning:

| | |
|---|---|
| Å | = Angstroms |
| AB | = AB pattern |
| ax | = axial |
| bs | = broad singlet |
| BSA | = bovine serum albumin |
| $^{13}$C-n.m.r | = C$^{13}$ nuclear magnetic resonance |
| d | = doublet |
| dd | = doublet of doublets |
| ddd | = doublet of doublets of doublets |
| DDQ | = dichlorodicyanoquinone |
| DTH | = delayed-type hypersensitivity |
| eq | = equatorial |
| g | = gram |
| $^1$H-n.m.r. | = proton nuclear magnetic resonance |
| i.r. | = infra red |
| kg | = kilogram |
| L | = liter |
| m | = multiplet |
| mL | = milliliter |
| q | = quartet |
| s | = singlet |
| t | = triplet |
| t.l.c. | = thin layer chromatography |
| U | = Units |
| μm | = microns |

AG 1×8 (formate form)=ion exchange resin AG 1×8 (formate form) available from Bio-Rad Laboratories, Richmond, Calif.

Dowex 50W×8 (H$^+$ form)=ion exchange resin Dowex 50×8 (H$^+$ form) available from Dow Chemical, Midland, Mich.

IR-120 resin (H$^+$ form)=amberlite resin available from Rohm & Haas, Philadelphia, Pa.

IR-C50 resin (H$^+$ form)=ion exchange resin IR-C50 (H$^+$ form) available from Rohm & Haas, Philadelphia, Pa.

Commercially available components are listed by manufacturer and where appropriate, the order number. Some of the recited manufacturers are as follows:

| | |
|---|---|
| Merck | = E. Merck AG, Darmstadt, Germany |
| Millipore | = Millipore Corp., Bedford, MA. |
| Waters | = Waters Associates, Inc., Milford, MA. |

The following examples are divided into two parts. The first part (part I) relates to the synthetic procedures to make the recited compounds whereas the second part (part II) relates to the biological results.

Part I—Synthetic Procedures

Examples 1–24 illustrate syntheses of the described compounds.

EXAMPLE 1

Synthesis of
Benzyl-2-O-benzoyl-4,6-O-benzylidene-3-
O-chloroacetyl-β-D-thiogalactopyranoside
(compound 31)

Dry a 20 L stirred reactor equipped with reflux condenser, heating mantle and 1 L addition funnel. Charge to this reactor 10 L of dichloroethane. Begin to stir the reactor then charge 1 kg D-galactose and 500 g anhydrous sodium acetate to the dichloroethane. Heat this slurry to reflux. Add dropwise 4 L of acetic anhydride to the reaction mixture using the 1 L addition funnel on the reactor. Reflux is to be maintained during the 2–4 hour addition period. Continue to stir and heat the mixture at reflux overnight.

When the reaction is complete as determined by t.l.c., turn off the heat to the reactor and add 250 mL of water in slow dropwise fashion using the addition funnel. This reaction is quite vigorous but is controlled by slowing the addition of the water. Stir the reaction for 1–2 hours. Charge 30 L of cold water to a 50 L stirred reactor and begin stirring. Drain the contents of the 20 L reactor into a 20 L polyethylene pail and pour into the stirring ice water in the 50 L reactor. Stir this mixture for twenty minutes. Drain the lower organic layer into a 20 L polyethylene pail. Extract the aqueous layer in the 50 L reactor with an additional 5 L of dichloromethane. Combine the dichloromethane extract with the first organic layer. Drain the aqueous layer to polyethylene pails and discard as aqueous waste.

Return the combined organic layers to the 50 L reactor and extract twice with 5 L portions of ice water for 10 minutes. Drain the organic layer to a clean 20 L polyethylene pail. Drain the aqueous to waste, return the organic layer to the 50 L reactor, stir and add 1 kg of anhydrous sodium sulfate. Stir for 1–2 hours and then drain the solution into a clean 20 L polyethylene pail and filter the solution using a 4 L vacuum filtration set [or large Buchner attached to a collector].

Concentrate the filtrate to 8 L then transfer into a clean 20 L reactor equipped with stirrer, 1 L addition funnel and cooling bath. Additional solvent can be added if the level of the solution is below the thermowell. Cool the organic solution to 0° C. using a cooling bath. Charge to this cool solution 724 g of benzyl mercaptan. Add a total of 1.1 L of colorless boron trifluoride etherate in slow dropwise fashion over 2 hours using the 1 L addition funnel. Stir the reaction 3–4 hours after the addition is complete maintaining the temperature at 0° C. The reaction is checked for completion by t.l.c. on silica gel. [The reaction can be left to sit overnight].

The reaction mixture is drained into a clean 20 L polyethylene pail. The 50 L reactor is charged with 15 L of saturated sodium carbonate solution. The 20 L polyethylene pail is slowly transferred into the slowly stirring carbonate solution at such a rate that the gas evolution is not overly vigorous. Stir the solution for 20 minutes then increase the rate of stirring. When gas evolution ceases bubble air through the entire solution for 24–36 hours. Drain the organic layer into a clean 20 L polyethylene pail and store in a hood. Extract the sodium carbonate solution with 3–5 L of dichloromethane and drain this solution into the same 20 L polyethylene pail.

Once the smell has been reduced the organic solution can be filtered using a 4 L vacuum filtration set and the filtrate evaporated under reduced pressure on the 20 L rotovap. 7 L of methanol is introduced into the rotavap flask and the residue heated with the rotavap bath till the residue dissolves in the warm methanol. The flask is rotated and allowed to cool. Cool ice water is added to the rotavap bath and the flask slowly rotated for several hours. The flask is removed from the rotovap and the white crystalline product filtered using a 4 L vacuum filtration set.

The benzyl 2,3,4,6-tetra-O-acetyl-β-D-thiogalactopyranoside (~1.3 kg) is charged into a clean dry 20 L reactor with stirring motor and 7 L of dry methanol is added to dissolve the material. The solution is treated with 3 g of freshly surfaced sodium and stirred for two hours. The reaction is checked by t.l.c. on silica gel using a retained sample of the benzyl 2,3,4,6-tetra-O-acetyl-β-D-thiogalactopyranoside with 80:20 ethyl acetate: methanol (v/v) the eluant. The absence of starting material indicates the reaction is complete.

50 g of fresh methanol washed $H^+$ ion exchange resin is added, the reaction stirred for 15 minutes. The pH is checked using pH paper to ensure a neutral solution. The resin is filtered off under reduced pressure and the methanol is removed under reduced pressure using the 20L rotovap. To the residue, 5 L of acetone is added to the 20 L flask and the solution warmed to reflux. The residue dissolves and is allowed to cool to room temperature at which time ice is added to the bath, the solution rotated with cooling overnight. 800–900 g of benzyl β-D-thiogalactopyranoside crystallizes and is filtered and dried under vacuum.

To 8 L of dry acetonitrile is added 800 g of benzyl β-D-galactopyranose, 600 g of benzaldehyde dimethyl acetal and 2–5 g of p-toluenesulphonic acid. The solution is stirred at room temperature overnight. The reaction progress is checked by t.l.c. When complete, the reaction is brought to pH 7 by the addition of triethylamine. The volume of acetonitrile is reduced to a minimum, 7 L of isopropanol is added and the mixture is heated to near reflux. Most of the product goes into the hot isopropanol after warming for several hours. The mixture is cooled and ice added to the bath and cooling continued overnight to give a precipitate. After filtering and drying the precipitate, 760 g of benzyl-4,6-O-benzylidene-β-D-thiogalactopyranoside is obtained.

180 g of benzyl-4,6-O-benzylidene-β-D-thiogalactopyranoside was dissolved in dry DMF and placed in a jacketed reactor. The reactor was cooled using a recirculating cooling bath maintained at a temperature of −25° C. and treated dropwise with 108 g of chloroacetyl chloride over 3 hours while stirring the reaction mixture. Stirring was continued 24 hours at this temperature then the reaction was quenched into several volumes of cold bicarbonate solution. The product was extracted into methylene chloride, water washed several times, dried over sodium sulphate and evaporated to dryness. The product was crystallized from isopropanol. Yield: 125 g of benzyl 4,6-O-benzylidene-3-O-chloroacetyl-β-D-thiogalactopyranoside.

5 g Benzyl 4,6-O-benzylidene-3-O-chloroacetyl-β-D-thiogalactopyranoside was benzoylated at room temperature in methylene chloride/pyridine using 3 equivalents of benzoyl chloride and a catalytic amount of dimethylaminopyridine. The solution is quenched into cold sodium bicarbonate solution, the organic layer is washed with saturated copper sulphate solution to remove the pyridine the organic layer dried and evaporated. The residue is taken up in hot isopropanol and benzyl 4,6-O-benzylidene-2-O-benzoyl-3-O-chloroacetyl-β-D-thiogalactopyranoside crystallizes from solution. $^1$H-n.m.r. (CDCl$_3$): δ=7.96, 7.4 (2m, 15H, aromatic, 5.79 (t, 1H, H-2), 5.5 (s, 1H, CH), 5.2 (q, 1H, H-4, $J_{2,3}$ 9.9 Hz, $J_{3,4}$ 3.3 Hz), 4.5 (m, 2H), 4.4 (d, 1H), 3.99 (m, 5H), 3.55 (s, 1H).

EXAMPLE 2

Synthesis of 4,6-O-benzylidene-2,3-di-O-benzoyl-β-D-galactopyranosyl bromide (compound 32A)

Benzyl-4,6-O-benzylidene-β-D-thiogalactopyranoside (10 g) was dissolved in 100 mL dichloromethane and 6.35 g of pyridine was added. To the solution was added 9 g of benzoyl chloride in dropwise fashion and after 1 hour, 50 mg of dimethylaminopyridine was added to the solution and the mixture was stirred for an addition 2 to 4 hours. The progress of the reaction was checked by t.l.c. on silica gel. Benzyl-4,6-O-benzylidene-2,3-di-O-benzoyl-β-D-thiogalactopyranoside (compound 32) was isolated by quenching the reaction mixture into saturated sodium bicarbonate solution and washing the organic extract with water, 5% copper sulfate solution, water, drying and evaporating the solvent. The residue was crystallized from isopropanol to give 10.7 g of compound 32.

Compound 32, benzyl-4,6-O-benzylidene-2,3-di-O-benzoyl-β-D-thiogalactopyranoside (9.89 g), was dissolved in 100 mL of dichloromethane, cooled to 0° C., and treated with a solution of bromine (2.85 g) in 10 mL of dichloromethane. After 15 minutes, 1.8 grams of tetraethylammonium bromide was added to the mixture and the mixture stirred for 2–3 hours at room temperature (followed by t.l.c. on silica gel). A small quantity of cyclohexane was added to quench excess bromine and the reaction mixture was quenched into cold saturate sodium bicarbonate solution, washed with water, dried and volume of the solution reduced to 30 mL. This dichloromethane solution of compound 32a was used directly in the synthesis of compound 42 without further isolation and/or purification.

EXAMPLE 3

Synthesis of p-Chlorophenyl 2,3,4-tri-O-benzyl-β-L-thiofucopyranoside (compound 20)

Dry a 2 L three neck round bottomed flask, reflux condenser and 500 mL addition funnel. Then cool under a flow of nitrogen. Charge to the flask 1000 g of L-fucose, 500 g of anhydrous sodium acetate and 800 mL of dry dichloroethane. Heat the mixture with stirring to 50° C. Charge to the addition funnel 400 mL of acetic anhydride. Add the acetic anhydride to the stirring, warm (50°–55° C.) slurry in dropwise fashion at a rate that does not cool the reaction appreciably. Upon completion of the addition stir the mixture for 72 hours at this temperature, removing aliquots from the reaction mixture every 24 hours to check the progress of the reaction by t.l.c.

When the reaction appears to be complete add 200 mL of water to the warm stirring mixture dropwise over 30 min. and stir for 1 hour at this temperature. This converts the remaining acetic anhydride to acetic acid. The reaction mixture is quenched into 3–4 volumes of water. The organic layer is removed and the aqueous layer is extracted with 4 L dichloromethane. The combined organic layers are backwashed three times with 2 L portions of water. The organic layers are dried over sodium sulphate and concentrated under reduced pressure to approximately 5 L.

To the organic layer is added 925 g of p-chlorothiophenol. The organic layer is cooled with cold water. To the mixture of p-chlorothiophenol and fucose acetates is added 1.72 kg of boron trifluoride etherate in dropwise fashion. The mixture is then stirred for 6 hours (overnight is acceptable) allowing the reaction mixture to come to ambient temperature. A small aliquot is removed from the reaction mixture and quenched into sodium bicarbonate solution. Once $CO_2$ evolution has ceased, the reaction is checked for completion by t.l.c. If complete, the whole reaction mixture is quenched into 1 L of saturated sodium bicarbonate and the organic layer separated after $CO_2$ evolution has finished. The organic layer is separated and air bubbled through this layer for 1 hour.

The separated organic layer is then dried over sodium sulphate and evaporated to dryness. The residue is taken up in 1 L of dry methanol in a 2 L round bottom flask and treated with 1 g of freshly surfaced sodium. The reaction is kept under nitrogen for several hours then checked by t.l.c. for removal of the acetate groups. The reaction is neutralized with $H^+$ ion exchange resin and filtered and evaporated under reduced pressure. The residue is taken up in a minimum of hot isobutanol and the p-chlorophenyl-β-L-thiofucopyranoside crystallizes from solution after cooling overnight at 0° C. Yield: 1060 g.

p-Chlorophenyl-β-L-thiofucopyranoside is dissolved in 7 L of dry dimethylsulphoxide. To the solution is added 600 g of powdered KOH and the reaction mixture stirred for 30 minutes. Benzyl chloride (1.275 L) is added dropwise to the stirring solution and the mixture stirred overnight at room temperature. T.l.c. indicates incomplete reaction so an additional 300 g of powdered KOH is added to the reaction mixture followed 30 minutes later by 425 mL of benzyl chloride. The solution is stirred at room temperature until t.l.c. indicates the reaction is complete. If the reaction is not complete after 24 hours, powdered KOH is added followed by 200 mL of benzyl chloride. The reaction is quenched into several volumes of water, extracted with methylene chloride, backwashed twice with water, dried and evaporated. The residue is taken up in hot hexanes. p-Chlorophenyl-2,3,4-tri-O-benzyl-β-L-thiofuco-pyranoside crystallizes and is filtered and dried under vacuum. Yield: 1.3 kg. $^1$H-n.m.r. (CDCl$_3$): δ=7.57 (m, 19H, aromatic), 4.99 (d, 1H), 4.65 (m, 5H), 4.55 (d, 1H, $J_{1,2}$ 9.5 Hz), 3.98 (t, 1H), 3.55 (m, 3H), 1.26 (d, 3H, $J_{5,6}$ 6.2 Hz, H-6).

EXAMPLE 4

Synthesis of
8-methoxycarbonyloctyl-2-acetamido-4,6-di-
O-benzylidene-2-deoxy-β-D-glucopyranoside
(Compound 5)

A 20 L glass reactor was charged with 8 L of dichloroethane, 1 L of acetic anhydride and 1 kg of anhydrous sodium acetate. To the stirring mixture was added 1 kg of glucosamine hydrochloride and the mixture was brought to reflux. A further 3.5 L of acetic anhydride was added dropwise to the refluxing solution over 3–4 hours and the solution maintained at reflux for 36 hours. During the last hour of reflux 200 mL of water was added dropwise to the solution. The reaction was then cooled and added to 35 L of ice water in a 50 L stirred reactor. The organic layer was removed and then water washed a second time with an additional 20 L of water. The organic layer was dried over sodium sulphate, filtered, and saturated with anhydrous gaseous HCl for 2 hours. The reaction was allowed to sit for 6 days being saturated with HCl for 1 hour every second day. 2-acetamido-2-deoxy-3,4,6-tri-O-acetyl-β-D-glucopyranosyl chloride was isolated by quenching into ice cold sodium bicarbonate solution. The organic layer was dried over sodium sulphate and evaporated to a brown solid.

Four hundred grams of 2-acetamido-2-deoxy-3,4,6-tri-O-acetyl-β-D-glucopyranosyl chloride was dissolved in 2 L of anhydrous dichloromethane containing 200 g of activated molecular sieves. 266 g of 8-methoxycarbonyloctanol was charged to the reaction mixture along with 317 g of mercuric cyanide. The solution was stirred rapidly at room temperature for 24 hours. After checking for reaction completion by t.l.c. the reaction mixture was filtered through a buchner funnel of silica and the organic layer washed twice with water, twice with a 5% solution of potassium iodide and twice with a saturated solution of sodium bicarbonate. The solution was dried over sodium sulphate and evaporated to dryness. The residue was taken up in anhydrous methanol and treated with 1 g of freshly cut sodium then stirred at room temperature overnight. The solution of 8-methoxycarbonyloctyl 2-acetamido-2-deoxy-β-D-glucopyranoside was neutralized with acid ion exchange resin and filtered and evaporated to yield 218 g of product after crystallization from isopropanol/diisopropyl ether.

Two hundred grams of 8-methoxycarbonyloctyl 2-acetamido-2-deoxy-β-D-glucopyranoside was dissolved in 1.2 L of anhydrous dimethylformamide and treated with 169 mL of dimethoxytoluene (benzylaldehyde dimethyl acetal) and 1–2 g of p-toluenesulphonic acid. The reaction was stirred and heated to 40° C. for 5 hours, then checked for completion by t.l.c. When the reaction appears complete the mixture was neutralized with triethylamine and quenched into several volumes of ice water, extracted into dichloromethane and backwashed several times with water. The organic layer was dried over sodium sulphate, evaporated to dryness and taken up in hot isopropanol. After cooling 8-methoxycarbonyloctyl-2-acetamido-4,6-O-benzylidene-2-deoxy-β-D-glucopyranoside precipitates. It is filtered and dried to yield 106 g of product. $^1$H-n.m.r. (CDCl$_3$): δ=7.41 (m,5H, aromatic), 6.11 (d, 1H, NH), 5.5 (s, 1H, CH), 4.63 (d, 1H, H-1, $J_{1,2}$ 7.4 Hz), 2.29 (t, 2H), 1.99 (s, 3H, Ac), 1.58 (m, 4H), 1.29 (bs, 8H).

EXAMPLE 5

Synthesis of
8-Methoxycarbonyloctyl-2-acetamido-3-
O-p-methoxybenzyl-4,6-O-benzylidene-β-
D-glucopyranoside (compound 6).

To a stirred solution of compound 5 (17.5 g, ~3 mmol) in dry dichloromethane (100 mL) and catalytic amount of p-toluenesulfonic acid (0.25 to 3 weight percent based on compound 5) was added dropwise a solution of p-methoxybenzyl trichloroacetimide (10 g in 25 mL CH$_2$Cl$_2$). The reaction mixture was stirred at room temperature overnight. Triethylamine was added to quench the reaction, the organic layer was washed with sodium bicarbonate solution and the organic layer dried and evaporated to dryness, Crystallization in hot ethanol gave 20 g of the desired product. $^1$H-n.m.r. (CDCl$_3$): δ7.56–6.90 (m, 9H, aromatic), 5.60 (d, 1H, NH), 5.30 (s, 1H, PhCH), 4.94 (d, 1H, J$_{1,2}$ 8.0 Hz, H-1), 3.80 (s, 3H, CH$_3$), 3.60 (s, 3H, CH$_3$Ph), 2.30 (t, 2H, CH$_2$CO), 1.90 (s, 3H, AcNH), 1.80–1.10 (m, 12H, (CH$_2$)$_6$).

EXAMPLE 6

Synthesis of 8-Methoxycarbonyloctyl-2-acetamido-2-deoxy-3-O-p-methoxybenzyl-6-O-benzyl-2-β-D-glucopyranoside (compound 7)

To a stirred solution of compound 6 (15.0 g, ~3 mmol) in 200 mL of dry THF were added, 11.0 g of sodium cyanoborohydride, 10 g of molecular sieves 4 Å and 5 mg of methyl orange. The solution was cooled to −10° C. and then ethereal hydrochloric acid was added dropwise until the solution remained acidic. On completion of the reaction, it was diluted with dichloromethane (200 mL), filtered through celite and washed successively with aqueous sodium bicarbonate (2×100 mL) and water (2×100 mL) and then the solvent dried and evaporated to give a syrup. Purification of the mixture on column chromatography using silica gel as adsorbent and eluting with hexane:ethyl acetate:ethanol (20:10:1) gave 7 in 70% yield. $^1$H-n.m.r. (CDCl$_3$): δ7.40–6.90(m, 9H, aromatic), 5.70(d, 1H, NH), 4.64(d, 1H, J$_{1,2}$ 8.0 Hz, H-1), 3.86(s, 3H, CH$_3$O), 3.68(s, 3H, CH$_3$OPh), 2.30(t, 2H, CH$_2$CO), 1.90(s, 3H, NHAc), 1.80–1.10(m, 12H, (CH$_2$)$_6$).

EXAMPLE 7

Synthesis of 8-Methoxycarbonyloctyl 2-acetamido-2-deoxy-3-O-p-methoxybenzyl-4-O-(4,6-O-benzylidene-2,3-O-dibenzoyl-β-D-galactopyranosyl)-6-O-benzyl-2-deoxy-β-D-glucopyranoside (compound 42)

A solution of compound 7 (10.61 g, 19.7 mmol) and compound 32A (1.6–1.7 equivalents based on compound 7) and 2,6-di-t-butyl-4-methyl pyridine (3.11 g, 15.2 mmol) in 250 L of dichloromethane and 40 g of molecular sieves (4 Å) was stirred at room temperature for 30 minutes, and then cooled to −50° C. under nitrogen. A dry solution of silver triflate (4.47 g, 17.3 mmol) in toluene (40 mL) was added to the stirred mixture. The mixture was warmed to −15° C. during two hours and kept at −15° C. for an additional 5 hours. At the end of which the mixture was warmed to room temperature and stirred overnight. 3 mL of pyridine and 250 mL of dichloromethane were added to the mixture and was filtered over celite, filtrate was washed with saturated aqueous sodium hydrogen carbonate (200 mL) and then with water (200 mL), aqueous hydrogen chloride (0.5N, 200 mL) and water (200 mL), concentrated in vacuo. 6.0 g of compound 8 was crystallized as white crystals from ethyl acetatediethyl ether-hexane. The mother liquor was concentrated, purified over chromatography (300 g silica gel, toluene:ethyl acetate, (1:1) to give 4.5 g pure compound 42. Total yield was 10.5 g (68%). Rf 0.48 (methanol:dichloromethane, 4:96). $^1$H-n.m.r. (CDCl$_3$): δ5.80(t, 1H, J$_{2',3'}$ 11.0 Hz, H-2'), 5.52(s, 1H, CHPh), 5.25(dd, 1H, J$_{3,4}$ 4.0 Hz, H-3'), 4.88(d, 1H, J$_{1',2'}$ 11.0 Hz, H-1'), 4.70(d, 1H, J$_{1,2}$ 9.0 Hz, H-1), 3.78(s, 2H, CH$_3$O), 3.64(s, 3H, CH$_3$OPh).

EXAMPLE 8

Synthesis of 8-Methoxycarbonyloctyl 2-acetamido-4-O-(4,6-O-benzylidene-2'3'-di-O-benzoyl-β-D-galacto-pyranosyl)-6-O-benzyl-2-deoxy-β-D-glucopyranoside (compound 43)

DDQ (126 mg, 0.5 mmol) was added to a stirred solution of compound 42 (350 mg, 185 μmol) in dichloromethane (10 mL) saturated with water. After 2 hours at room temperature, the reaction was complete, and organic layer was successively washed with aqueous sodium bicarbonate and water, dried and concentrated. Column chromatography gave the desired compound 43 in 85% yield. $^1$H-n.m.r. (CDCl$_3$): δ5.65(dd, 1H, J$_{2',3'}$ 10.8 Hz, H-2'), 5.61(d, 1H, J$_{3',4'}$ 4.0 Hz, H-3'), 4.68(d, 1H, J$_{1',2'}$ 11.0 Hz, H-1'), 4.62(d, 1H, J$_{1,2}$ 10 Hz, H-1), 3.60(s, 3H, COO$\underline{C}$H$_3$).

EXAMPLE 9

Synthesis of 8-methoxycarbonyloctyl 2-acetamido-3-O-(2,3,4-tri-O-benzyl-α-L-fucopyranosyl)-4-O-(4,6-O-benzylidene-2,3-di-O-benzoyl-β-D-galactopyranosyl)-6-O-benzyl-2-deoxy-β-D-glucopyranoside (compound 44)

To a mixture of copper (cupric) bromide (40 g, 17.7 mmol) and 5 g of molecular sieves 4 Å in 10 mL of dry dichloromethane were added 1.2 mL of dry DMF and tetraethylammonium bromide (1.85 g, 8.8 mmol). The mixture was stirred at room temperature for 1 hour and then a solution of compound 43 (5.0 g, 5.75 mmol) and the thiofucoside 20 (7.5 g, 11.8 mmol) in 30 mL dry dichloromethane was added dropwise at 0° C. for 30 minutes. The mixture was stirred at room temperature for 48 hours, at the end of which time 5 mL of methanol was added and stirred for 30 minutes. Further, 3 mL of pyridine, 100 mL of ethyl acetate and 100 mL of toluene were added to the reaction mixture. The mixture was filtered over celite pad and the solvent evaporated to give a brown syrup. Purification over column chromatography with silica gel and eluted with toluene:ethyl acetate (2:1) gave the compound 44 in 86% yield. $^1$H-n.m.r. (CDCl$_3$): δ5.80(dd, 1H, J$_{2',3'}$ 11.0 Hz, H-2'), 5.60(s, 1H, CHPh), 5.50(d, 1H, NH), 5.10(dd, 1H, J$_{3',4'}$ 4.0 Hz, H-3'), 3.60(s, 3H, OCH$_3$), 1.20(d, 3H, CH$_3$, fucose).

EXAMPLE 10

Synthesis of 8-methoxycarbonyloctyl 2-acetamido-3-O-(2,3,4,-tri-D-benzyl-α-L-fucopyranosyl)-4-O-(4,6-O-benzylidene-β-D-galactopyranosyl)-6-O-benzyl-2-deoxy-β-D-glucopyranoside (compound 45)

compound 44 (200 mg) was treated with 20 mL of sodium methoxide in methanol. After 3 hours, t.l.c. (toluene-ethyl acetate, 1:1) indicated the disappearance of the starting material and the appearance of a slower moving spot. The solution was neutralized with amberlite resin IR-120 H$^+$ and the solvent evaporated under reduced pressure to give a quantitative yield of crude compound 45. The product was purified on silica gel using tolueneethyl acetate (2:1) as eluant. $^1$H-n.m.r. (CDCl$_3$): δ7.15–7.55 (aromatic, 25H), 5.62 (d, 1H,NH), 5.58 (s, 1H, CH-benzylidene), 5.06(d, 1H, J$_{1'',2''}$ 7.0 Hz, H-1''), 4.95 (d, 1H, J$_{1',2'}$ 3.8 Hz, H-1') 4.85 (d, 1H, J$_{1,2}$=9.0 Hz, H-1) 3.62 (s, 3H, COOCH$_3$) 1.0(d, 2H, Fuc-CH$_3$).

EXAMPLE 11

Synthesis of 8-methoxycarbonyloctyl 2-acetamido-3-O-(α-L-fucopyranosyl)-4-O-(3-O-sulphate-β-D-galactopyranosyl)-2-deoxy-β-D-glucopyranoside (compound 47)

Diol (100 mg—compound 45) was dissolved in 5 mL dry dimethylformamide. Pyridine:sulfur trioxide complex (120 mg) was added to the solution and the reaction mixture stirred ar room temperature for 1 hour. The reaction was followed by t.l.c. to monitor the disappearance of the diol ($R_f$=0.28 in EtOAc: MeOH 80:20). Solvent was evaporated to dryness and taken up in 50 mL of methanol then treated with $Na^+$ resin to convert it to the sodium salt. Purification by column chromatography on silica gel gave 65 mg of compound 46 which was immediately hydrogenated with 10% $Pd(OH)_2$ on carbon to give 35 mg of compound 47. $^{13}C$-n.m.r. ($D_2O$ ): δ103.94(C-1, Gal), 103.44(C1, GlcNAc), 101.07(C-1, Fuc), 82.7(C-3, Gal), 63.83(C-6, Gal), 62.2(C6, GlcNAc), 54.55 (C-N, GlcNAc), 17.75 (C6-Fuc).

EXAMPLE 12

Synthesis of 2-O-benzoyl-4,6-O-benzylidene-3-O-chloroacetyl-β-D-galactopyranosyl bromide (compound 33)

Compound 32, benzyl 4,6-O-benzylidene-2-O-benzoyl-3-chloroacetyl-β-D-thiogalactopyranoside (8.87 g) was dissolved in 100 mL of dichloromethane, cooled to 0° C. and treated with a solution of bromine (2.7 g) in 10 mL of dichloromethane. After 15 minutes, 1.7 g of tetraethylammonium bromide was added to the mixture and the mixture stirred for 2 to 3 hours at room temperature (followed by t.l.c. on silica gel). A small quantity of cyclohexene was added to quench excess bromine and the reaction mixture was quenched into cold saturate sodium bicarbonate solution, washed with water, dried, and the volume of the solution reduced to 30 mL so as to provide a dichloromethane solution of compound This solution was used directly in the synthesis of compound 38.

EXAMPLE 13

Synthesis of 8-methoxycarbonyloctyl 2-acetamido-4-O-(2'-O-benzoyl-4',6'-O-benzylidene-3'-O-chloroacetyl-β-D-galactopyranosyl)-6-O-benzyl-2-deoxy-3-O-p-methoxybenzyl-β-D-glucopyranoside (compound 37)

A solution of the compound 7 (5.0 g, 0.9 mmol) and compound 33 (1.4 to 1.5 equivalents—from example 12) and 2,6-di-t-butyl-4-methyl pyridine (1.78 g, 1.0 mmol) in 50 mL of dichloromethane and 20 g of molecular sieves (4 Å) was stirred at room temperature for 30 minutes, and then cooled to −50° C. under nitrogen. A dry solution of silver triflate (3.3 g, 1.5 mL) in toluene (10 mL) was added to the stirred mixture. The mixture was warmed to −15° C. over two hours and kept at −15° C. for an additional 5 hours, then allowed to warm to room temperature and stirred overnight. 1 mL of pyridine and 100 mL of dichloromethane were added to the mixture and it was filtered over celite, the filtrate was washed with aqueous sodium bicarbonate (100 mL) and then with water (100 mL), aqueous hydrogen chloride (0.5N, 100 mL) and water (100 mL), then concentrated in vacuo. Purification of the crude mixture on column chromatography with silica gel as adsorbent eluted with hexane:ethyl acetate (1:1) gave 5.2 g of pure compound 37. $^1H$-n.m.r. ($CDCl_3$): δ5.85(d, 1h, NH), 5.62(t, 1H, $J_{2',3'}$ 10.8 Hz, H-2'), 5.52(s, 1H-CH-benzylidene), 5.08 (dd, 1H, $J_{3',4'}$ 4 Hz, H-3'), 4.85 (d, 1H, $J_{1',2'}$ 11.0 Hz, H-1'), 4.68 (d, 1H, $J_{1,2}$ 9.0 Hz, H-1), 3.72 and 3.64 (2s, 6H, $OCH_3$ and $COOCH_3$); $^{13}C$-n.m.r.: 159.0(aromatic c-p-methoxyl) 165.15(c=0, chloroacetyl), 167.12(c-0, acetyl), 174.2 (c=0, $COOCH_3$), 99.64(c-1), 100.26(c-1'), 101.0(PhCH).

Compound 37 was then treated with DDQ in the same manner as Example 8 to give compound 38 in near quantitative yields.

EXAMPLE 14

Synthesis of 8-methoxycarbonyloctyl 2-acetamido-3-O-(2,3,4-tri-O-benzyl-α-L-fucopyranosyl)-4-O-(2-O-benzoyl-4,6-O-benzylidene-3-O-chloroacetyl-β-D-galactopyranosyl)-6-O-benzyl-2-deoxy-β-D-glucopyranoside (compound 39)

Thiofucoside 20 (4 g) was stirred in dry dichloromethane (50 mL) and bromine (0.60 g) was added. The mixture was cooled to −20° C. The conversion to the bromide was complete in 1 hour and the reaction mixture was washed with cold aqueous sodium bicarbonate, dried and concentrated to 10 mL and syringed into a flask containing the alcohol 38 (2.97 g, 3.56 mmol), $CuBr_2$ (2.39 g), tetraethylammonium bromide (2.24 g), molecular sieves 4 Å (4 g) in dimethylformamide (1 mL) in dry dichloromethane (75 mL). The mixture was stirred at room temperature for 48 hours after which the t.l.c. showed the disappearance of the alcohol 38 and a faster moving spot (Rf 0.56—toluene:ethyl acetate 2:1). After the usual work up, the crude mixture was purified by column chromatography to give compound 39 (4.2 g, about 80% yield). $^1H$-n.m.r. ($CDCl_3$): δ7.1–8.0 (m,aromatic-30H), 5.58, 5.61 (m, 2H, NH and CH-benzylidene, overlapping), 5.56 (d, 1H, $J_{1'',2''}$ 7.0 Hz, H-1''), 4.98 (d, 1H, $J_{1,2}$ 8.0 Hz, H-1), 4.95 (d, 1H, $J_{1',2'}$ 3.8 Hz, H-1'), 3.65 (s, 3H, $COOCH_3$) and 1.1 (d, 3H, $CH_3$-Fuc).

Compound 39 is then dechloroacetylated by treatment with thiourea and the compund is sulphated with sulfur trioxide/pyridine complex in dimethylformamide at 0° C. for 2 hours to provide for compound 41. The blocking groups on compound 41 are then removed by conventional techniques to provide for compound 47.

EXAMPLE 15

Synthesis of 2-deoxy-2-phthalimido-1,3,4,6-tetra-O-acetyl-β-D-glucopyranoside (compound 1)

(D+) Glucosamine hydrochloride (100 g, 0.46 mol) was added to a solution of sodium methoxide in methanol which was prepared from equimolar amount of sodium metal in methanol (0.5 L). The resultant mixture was treated with equimolar equivalent of phthalic anhydride and triethylamine (80 mL). The mixture was then stirred for 2 hours, filtered and the solid was dried in vacuum for 12 hours. The dry solid was dissolved in pyridine (300 mL) and treated with acetic anhydride (200 mL, 2.1 mol). The mixture was then stirred at room temperature for 48 hours. The reaction mixture was then treated with an ice-water mixture, and the resultant precipitate was filtered, concentrated and crystallized from diethylether to 98.3 g (45%) of the title compound. $^1H$-n.m.r. ($CDCl_3$): δ7.75 (m, 4h, aromatic), 6.45 (d, 1H, H-1, $J_{1,2}$ 9.0 Hz), 5.85 (t, 1H), 5.15 (t, 1H), 4.4 (t, 1H), 4.3 (q, 1H), 4.1 (q, 1H), 4.00 (m, 1H), 2.05, 2.00, 1.95, 1.80 (4s, 12H, 4Ac). $^{13}$C-n.m.r. (CDCl$_3$) δ89.7 (C-1), 72.6, 70.5, 68.3 (3C, C-3, C-4, C-5), 61.45 (C-6), 53.42 (C-2).

EXAMPLE 16

Synthesis of 2-deoxy-2-phthalamido-3,4,6-tri-O-acetyl-β-D-glucopyranosyl bromide (compound 12)

2-deoxy-2-phthalamido-1,3,4,6-tetra-O-acetyl-β-D-glucopyranoside 1 (20 g, 41.9 mmol) was treated with hydrogen bromide solution in acetic acid (30%, 200 mL) and stirred at room temperature for 2 hrs. The mixture was then poured into an ice water mixture and extracted with dicloromethane. The extract was washed with NaHCO$_3$ solution and water followed by MgSO$_4$ drying. The mixture is filtered, dried and concentrated in vacuo to give compound 12 as a dry syrup (compound 12)

EXAMPLE 17

Synthesis of Ethyl 2-deoxy-2-phthalimido-3,4,6-tri-O-acetyl-β-D-glucopyranoside (compound 13)

2-Deoxy-2-phthalamido-3,4,6-tri-O-acetyl-β-D-glucopyranosyl bromide (compound 12) from example 16 was taken up in dry ethanol and treated directly with dry ethanol (200 mL), mercuric cyanide (13.7 g. 55 mmol) and stirred at room temperature for 48 hr. The mixture was then filtered and concentrated. The residue was taken up in 200 mL of dichloromethane and washed with a solution of 10% potassium iodide, 5% sodium bicarbonate, water, dried over MgSO$_4$ and concentrated to a syrup.

EXAMPLE 18

Synthesis of Ethyl 2-deoxy-2-phthalimido-β-D-glucopyranoside (Compound 14)

Ethyl 2-deoxy-2-phthalamido-3,4,6-tri-O-acetyl-β-D-glucopyranosyide (compound 13) from example 17 was taken up in 100 mL of dry methanol and treated with 100 mg of sodium metal. The solution was stirred at room temperature for 24 hours and then neutralized with Amberlite [R-120(H+)] resin, filtered, and evaporated to dryness in vacuo. This compound was used in the preparation of compound 15 and compound 66.

EXAMPLE 19

Synthesis of Ethyl 2-deoxy-2-phthalimido-6-O-benzyl-β-D-glucopyranoside (Compound 15)

Compound 14 (2.1 g, 6.23 mmol) was taken up in 100 mL of toluene. To it was added bis(tributyl tin) oxide (2.22 mL, 4.35 mmol) and tetrabutylammonium bromide (0.983 g, 3.05 mmol). The mixture was heated at 150° C. for 4 hours and then toluene (50 mL) was distilled off from the mixture. The reaction mixture was cooled to room temperature and benzyl bromide (2.17 mL, 18.27 mmol) was added and the reaction heated to 110° C. for 36 hours. Toluene was evaporated and the residue taken up in ethyl acetate (22 mL), washed successively with aqueous sodium bicarbonate, saturated sodium chloride solution and water. The organic layer was dried and evaporated to dryness to give a crude solid. Purification by column chromatography on silica gel gave a crystalline solid 15 (1.4 g, 70%). $^1$H-n.m.r. (CDCl$_3$) δ7.3–8.1 (9H, aromatic), 4.5 (dd, 2H, C$\underline{H}_2$Ph), 5.18 (d, 1H, $J_{1,2}$ 10.0 Hz, H-1), 4.36 (dd, 1H, H-3), 4.25 (dd, H, $J_{2,1}$ 10.0 Hz, $J_{2,3}$ 8.0 Hz, H-2) and 1.0(t, 3H, CH$_3$).

EXAMPLE 20

Synthesis of Ethyl 6-O-benzyl-2-deoxy-2-phthalimido-3-O-(2,3,4,-tri-O-benzyl-α-L-fucopyranosyl)-4-O-(2,3,4,6-tetra-O-acetyl-β-D-galactopyranosyl)-β-D-glucopyranoside (Compound 49)

To a stirred solution of compound 15 (2.49, 5.71 mmol) in dry dichloromethane (50 mL) was added dry CaSO$_4$ (7.5 g), silver triflate (0.73 g, 2.8 mmol) and silver carbonate (7.0 g, 25.7 mmol) and the reaction mixture cooled to −50° C. 2,3,4,6-tetraacetyl-1-α-bromogalactose (3.5 g, 8.5 mmol) in dry dichloromethane (15 mL) was added dropwise through a dropping funnel. The reaction mixture was warmed to −30° C. and stirred for 48 hours and then methanol (5 mL) was added to cease the reaction and the mixture allowed to warm to room temperature. After filtration through a celite pad and the filtrate was washed with aqueous bicarbonate and 5% EDTA solution. Evaporation of the solvent in vacuo gave a reddish brown syrup which was chromatographed on silica with toluene: acetone:MeOH (20:3:1) as eluant to give compound 48 (Rf 0.528) as the major compound.

Thiofucoside 20 (1.5 g, 2.8 mmol) was stirred in dry dichloromethane (50 mL) cooled to −20° C. and bromine (0.40 g) was added. The conversion to bromide was complete in 1 hour and the reaction mixture was washed with cold aqueous bicarbonate, dried and concentrated to 50 ml and syringed into a flask containing compound 48 (1 g, 1.4 mmol), HgBr$_2$ (1.08 g, 3 mmol), molecular sieves 4 Å (2 g) and tetraethylammonium bromide (1 g) in dry dichloromethane (50 mL). The mixture was stirred at room temperature for 48 hours. T.l.c. showed a faster moving spot. The reaction mixture was filtered through celite, and the filtrate washed with water, 5% EDTA, saturated aqueous sodium bicarbonate, water, then dried over sodium sulphate, filtered and evaporated to dryness in vacuo. Purification of the crude product by silica gel chromatography gave the title compound 49 (1.2 g, 70%, Rf 0.669 in toluene; acetone; MeOH 20:3:1).

$^1$H-n.m.r. (CDCl$_3$): δ7.00–7.8 (aromatic 24H) 5.35(d,1H, $J_{1,2}$ 9.0 Hz, H-1), 5.15 (d, 1H, $J_{1,2}$ 3.8 Hz, H-1-Fuc), 4.35(dd, 1H, $J_{2',3'}$ 10.0 Hz, H-3') 2.1(s, 3H, acetyl C$\underline{H}_3$) 1.95(s, 6H, acetyl C$\underline{H}_3$), 1.90(S, 3H, acetyl C$\underline{H}_3$), 1.1(t, 3H, CH$_3$), and 0.6 (d, 3H, C$\underline{H}_3$-Fuc). $^{13}$C-n.m.r.: δ168, 170 (C=O, phthalimido and acetyl), 101.0 (C-1, Gal), 100.0(C-1, GlcNPhth) 97.7(C-1-Fuc), 20.6(CH$_2$-C$\underline{H}_3$) and 15.98(C-6-Fuc).

EXAMPLE 21

Synthesis of Ethyl 2-acetamido-6-O-acetyl-3-O-benzyl-2-deoxy-β-D-glucopyranoside A solution of compound 90 (described below-2 g, 4.68 mmol) in aqueous acetic acid (80%, 150 mL) was heated at 80° C. for 2 hours. The mixture then was evaporated and the resultant solid was dried over P$_2$O$_5$ in high vacuum. The dry solid was selectively acetylated with acetyl chloride (0.33 mL, 4.7 mmol) and pyridine (10 mL) in dichloromethane (100 mL) at ⁻10° C. to 5° C. The mixture was then diluted with dichloromethane (50 mL), washed with aqueous NaHCO$_3$, dried over MgSO$_4$ and evaporated. The residue was chromatographed on a silica gel column using EToAc: hexanes, 3:1 (v:v) as eluant to give 0.82 g (46%) of the title compound: $^1$H-n.m.r. (300 MHz, CDCl$_3$): δ7.3 (m, 5H, aromatic), 5.67(bs, 1H, NH), 4.86(d, 1H, H-1), 4.75(m, 2H), 4.48(q, 1H), 4.27(d, 1H), 4.1(t, 1H), 3.85(m, 1H), 3.5(m, 3H), 3.16(m, 1H), 2.70(bs, 1H, OH), 2.1(s, 3H, Ac), 1.9(s, 3H, Ac), 1.18(t, 3H, CH$_3$), $^{13}$C-n.m.r. (CDCl$_3$): δ99.45(C-1), 79.85, 74.5(CH$_2$ph), 73.7, 71.09, 65.25 (C-6), 63.36(CH$_2$—), 57.7(C-2), 23.6(Ac), 20.86(Ac), 15.06(CH$_3$).

EXAMPLE 22

Synthesis of Ethyl 6-O-acetyl-3-O-benzyl-2-deoxy-2-phthalimido-β-D-glucopyranoside (compound 69)

A solution of ethyl 2-deoxy-2-phthalimido-β-D-glucopyranoside (compound 14) from Example 18 was taken up in dry acetonitrile (100 mL) and treated with benzaldehyde dimethylacetal (9.6 g) and a catalytic amount of p-toluenesulphonic acid (100 mg). The mixture was stirred for 17 hours at room temperature and then neutralized to pH 7 with triethylamine. The mixture was evaporated and crystallized from hot hexanes to give 12.7 grams of ethyl 4,6-O-benzylidene-2-deoxy-2-phthalimido-β-D-glucopyranoside compound 66.

Compound 66 (10 g) was dissolved in dry dimethylformamide (DMF) at −5° C. and treated with 1.1 g (46.6 mol) sodium hydride and benzoyl bromide (5.46 mL, 22 mmol). The mixture was stirred at 0° C. for 2 hours and then treated slowly with 20 mL methanol then slowly brought to room temperature and treated with HCl (1N) to pH 7 and then extracted three times with dichloromethane. The organic layer was dried over anhydrous magnesium sulfate then filtered, concentrated to dryness and taken up in hot ethanol to give 7.2 g of compound 67. Compound 67 (5.43 g, 10.50 mmol) in aqueous acetic acid (80%, 200 mL) was heated at 80° C. for 2 hours. The mixture was evaporated and the resultant solid was dried over P$_2$O$_5$ in high vacuum. The dry solid was selectively acetylated with acetyl chloride (0.8 mL, 11.0 mmol) and pyridine (10 mL) in dichloromethane (200 mL) at ⁻10° C. to 0° C. The mixture was then diluted with dichloromethane (10 mL), washed with aqueous NaHCO$_3$, dried over MgSO$_4$ and evaporated. The residue was chromatographed on a silica gel column using EtOAc:hexane, 1:2 (v:v) as eluant to give 3.5 g (71%) of the compound 69: $^1$H-n.m.r. (300 MHz, CDCl$_3$): δ7.7 (m, 4H, aromatic), 7.0 (m, 5H, aromatic), 5.16(d, 1H, H-1), 4.7(d, 1H), 4.5(m, 2H), 4.2(m, 3H), 3.8(m, 1H), 3.6(m, 2H), 3.45(m, 1H), 2.9(bs, 1H, OH), 2.1(s, 3H, Ac), 1.95(t, 3H, CH$_3$). $^{13}$C-n.m.r. (CDCl$_3$): δ98.09(C-1), 78.45, 74.5, 73.9, 71.7, 65.1, 63.1, 55.5, 20.87 (Ac), 14.92 (CH$_3$).

EXAMPLE 23

Synthesis of Ethyl 6-O-acetyl-3-benzyl-2-deoxy-2-phthalimido-4-O-(2,3,4,6-tetra-O-acetyl-β-D-galactosyl)-β-D-glucopyranoside (compound 70)

To a stirred solution of compound 9 (80 mg, 0.17 mmol) in dichloromethane (10 mL) containing molecular sieves (3A°, 1 g), 2,6-di-tert-butyl-4-methyl-pyridine (45 mg, 0.22 mmol) and silver triflate (57 mg, 0.22 mmol) was added, at ⁻30° C. under nitrogen, 2,3,4,6-tetra-O-acetyl-α-D-galactosyl bromide in dichloromethane (5 mL). The mixture was stirred at this temperature for 1 h and then warmed up to 5° C. over 2 h. The mixture was then diluted with dichloromethane (10 mL), filtered and the insoluble material was washed with dichloromethane (5 mL). The combined filtrates were washed with saturated aqueous sodium hydrogen carbonate and water, dried over MgSO$_4$, and concentrated. The residue was chromatographed on a silica gel column using ethyl acetate: hexanes, 1:2 (v:v) as eluant to give 120 mg (80%) of the title compound: $^1$H-n.m.r. (300 MHz, CDCl$_3$): δ7.68, 6.96(2m, 9H, aromatic), 5.3(m, 2H), 5.13(d, 1H, H- 140 , J$_{1',2'}$ 8.0 Hz), 4.99(q, 1H), 4.82(d, 1H), 4.62(d, 1H, H-1, J$_{1,2}$ 7.7 Hz), 4.54(d, 1H), 4.42(d, 1H), 4.3(q, 1H), 4.15(m ,2H), 3.99(m, 2H), 3.87(m, 2H), 3.72(m, 2H), 3.46(m, 1h), 2.15, 2.12, 2.09, 2.00, 1.98(5s, 15H, 5XAc), 1.00(t, 3H, CH$_3$). $^{13}$C-n.m.r. (CDCl$_3$): δ101.2, 97.8(C-1, C-1'), 14.85(CH$_3$).

The 2-amine of Compound 67 above can be regenerated by contacting this compound with hydrazine acetate and then acetylated with acetic anhydride/pyridine or other acetylating agents to provide for a disaccharide (compound 90)

EXAMPLE 24

Synthesis of Ethyl 2-acetamido-6-O-acetyl-2-deoxy-4-O-(2,3,4,6-tetra-O-acetyl-β-D-galactosyl)-3-O-(2,3,4-tri-O-benzyl-α-L-fucosyl)-β-D-glucopyranoside To a stirred solution of the disaccharide 90 (80 mg, 0.129 mmol) in dichloromethane (2 mL) containing molecular sieves (3A°, 1 g), tetraethylammonium bromide (41 mg, 0.195 mmol), dimethylformamide (0.1 mL) and diisopropylethylamine (0.087 mL, 0.5 mmol) was added, at room temperature under nitrogen, a solution of 2,3,4-tri-O-benzylfucosyl bromide (130 mg, 0.26 mmol—as per Example 9) in dichloromethane (2 mL). The mixture was stirred at room temperature under nitrogen for 72 h and then filtered, and the insoluble material was washed with dichloromethane (10 mL). The combined filtrates were washed with saturated aqueous sodium hydrogen carbonate and water, dried over MgSO$_4$, and concentrated. The residue was chromatographed on a silica gel column using ethyl acetate-:hexanes, 3:1 (v:v) as eluant to give 115 mg (90%) of the title trisaccharide 6: $^1$H-n.m.r. (300 MHz, CDCl$_3$): δ7.30(m, 15H, aromatic), 6.00(d, 1H, NH, J 8.0 Hz), 5.38(d, 1H, H-1 Fuc, J$_{1,2}$ 3.3 Hz), 5.14(d, 1H, H-1 Glc, J$_{1,2}$ 7.8 Hz), 5.1(m, 1H), 4.98(m, 2H), 4.80(m, 6H), 4.40(m, 2H), 4.33(q, 1H), 4.1(m, 5H), 3.77(m, 7H), 3.48(m, 1H). 2.09, 2.07, 2.01, 2.00, 1.97(5XAc, 15H), 1.80(s, 3H, NAc), 1.18(d, 3H, H-6 Fuc, J$_{5,6}$ 6.6 Hz), 1.087 (t, 3H, CH$_3$ofEt). $^{13}$C-n.m.r. (CDCl$_3$): δ99.87 (C-1 Gal), 99.19(C-1 Glc), 97.18(C-1 Fuc), 16.67(C-6 Fuc), 14.79(CH$_3$ofEt).

EXAMPLE 25

Synthesis of GDP-Fucose

As noted above, fucosylation of the sulfated Lewis$^x$ and Lewis$^a$ structures can be achieved by use of an appropriate fucosyltransferase which are well known in the art. Enzymatic fucosylation requires the use of GDP-fucose. Accordingly, the purpose of this example is to illustrate the synthesis of GDP-fucose. This is achieved in a 3 step process as illustrated below:

A. Preparation of Bis (tetra-n-butylammonium) hydrogen phosphate

Tetra-n-butylammonium hydroxide (40% aq. w/w, about 150 g) was added dropwise to a solution of phosphoric acid (85% aq, w/w, 18 g, 0.155 mmol) in water (150 mL) until the pH reached 7. Water was then evaporated in vacuo to give a syrup which was co-evaporated with dry aceto-nitrile (2×400 mL) followed by dry toluene (2×400 mL). The resulting white solid (75 g) was dried in vacuo and stored over phosphorus pentoxide under vacuum until used.

B. Preparation of β-L-Fucopyranosyl-1-phosphate

A solution of bis(tetra-n-butylammonium) hydrogen phosphate (58 g, 127.8 mmol) in dry acetonitrile (300 mL) was stirred at room temperature under nitrogen in the presence of molecular sieves (4 Å, 20 g) for about one hour. A solution of tri-O-acetyl fucosyl-1-bromide (freshly prepared from 31 g, 93 mmol of L-fucose tetraacetate in the manner of Nunez et al.[53]) in dry toluene (100 mL) was added dropwise in about 0.5 hour to the above solution, cooled at 0° C. After one more hour at 0° C., the mixture was brought to room temperature and stirred for 3 hour. Tlc (1:1 toluene:ethyl acetate) indicated a main spot on the base line and several faster moving smaller spots.

The mixture was filtered over a pad of Celite (which was further washed with acetonitrile) and the solvents evaporated in vacuo to give a red syrup. This material was dissolved in water (400 mL) and extracted with ethyl acetate (250 mL, twice). The aqueous layer was then evaporated in vacuo leaving a yellowish syrup to which a solution of ammonium hydroxide (25% aq., 200 mL) was added. The mixture was stirred at room temperature for 3 hours after which tlc (65:35:8 chloroform:methanol:water) indicated a baseline spot. The solvent was evaporated in vacuo to give a yellowish syrup which was diluted with water (400 mL). The pH of this solution was checked and brought to 7, if necessary, by addition of a small amount of hydrochloric acid. The solution was slowly absorbed onto a column of ion exchange resin Dowex 2×8 [200–400 mesh, 5×45 cm, bicarbonate form which had been prepared by sequential washing of the resin with methanol (800 mL), water (1200 mL), ammonium bicarbonate (1M, 1600 mL) and water (1200 mL)]. Water (1000 mL) was then run through the column followed by a solution of ammonium bicarbonate (0.5M, 2.3 mL/minute, overnight). The eluate was collected in fractions (15 mL) and the product detected by charring after spotting on a tlc plate. Fractions 20 to 57 were pooled and evaporated in vacuo leaving a white solid which was further co-evaporated with water (3×300 mL) and freeze drying of the last 50 mL and then drying of the residue with a vacuum pump to give β-L-fucopyransyl-1-phosphate (9.5 g, 40%) as a 12:1 mixture of β and α anomers containing some ammonium acetate identified by a singlet at δ=1.940 in the $^1$H-n.m.r. spectrum. This product was slowly run through a column of Dowex 5×8 resin (100–200 mesh, triethylammonium form) and eluted with water to provide the bis triethylammonium salt of β-L-fucopyransyl-1-phosphate as a sticky gum after freeze drying of the eluate. $^1$H-n.m.r. δ:4.840 (dd, $J_{1,2}=J_{1,P}$=7.5 Hz, H-1), 3.82 (q, 1H, $J_{5,6}$ 6.5 Hz, H-5), 3.750 (dd, 1H, $J_{3,4}$ 3.5, $J_{4,5}$ 1.0 Hz, H-4), 3.679 (dd, 1H, $J_{2,3}$ 10.0 Hz, H-3), 3.520 (dd, 1H, H-2), 1.940 (s, acetate), 1.26 (d, H-6). Integral of the signals at 3.20 (q, J 7.4 Hz, NC$\underline{H}_2$) and 1.280 and 1.260 (NCH$_2$C$\underline{H}_3$ and H-6) indicates that the product is the bis-triethyl-ammonium salt which may loose some triethylamine upon extensive drying. $^{13}$C-n.m.r. δ:98.3 (d, $J_{C,1P}$ 3.4 Hz, C-1), 72.8 (d, $J_{C,2P}$ 7.5 Hz, C-2), 16.4(C-6); $^{31}$P-nmr δ: +2.6(s).

β-L-fucopyransyl-1-phosphate appears to slowly degrade upon prolonged storage (1+ days) in water at 22° C. and, accordingly, the material should not be left, handled or stored as an aqueous solution at 22° C. or higher temperatures. In the present case, this material was kept at −18° C. and dried in vacuo over phosphorus pentoxide prior to being used in the next step.

C. Preparation of Guanosine 5'-(β-1-fucopyranosyl)-diphosphate

Guanosine 5'-(β-1-fucopyranosyl)-diphosphate was prepared from β-L-fucopyranosyl-1-phosphate using two different art recognized procedures as set forth below:

PROCEDURE #1

β-L-fucopyranosyl-1-phosphate and guanosine 5'-monophosphomorpholidate (4-morpholine-N,N'-dicyclohexyl-carboxamidine salt, available from Sigma, St. Louis, Mo., "GMP-morpholidate") were reacted as described in a recent modification[54,56] of Nunez's original procedure[55]. Accordingly, tri-n-octylamine (0.800 g, available from Aldrich Chemical Company, Milwaukee, Wis.) was added to a mixture of β-L-fucopyranosyl-1-phosphate (triethylammonium salt, 1.00 g, about 2.20 mmol) in dry pyridine (10 mL) under nitrogen the solvent removed in vacuo. The process was repeated three times with care to allow only dry air to enter the flask. GMP morpholidate (2.4 g, about 3.30 mmol) was dissolved in a 1:1 mixture of dry dimethylformamide and pyridine (10 mL). The solvents were evaporated in vacuo and the procedure repeated three times as above. The residue was dissolved in the same mixture of solvents (20 mL) and the solution added to the reaction flask accompanied by crushed molecular sieves (2 g, 4 Å). The mixture was stirred at room temperature under nitrogen. Tlc (3:5:2 25% aq. ammonium hydroxide, isopropanol and water) showed spots corresponding to the starting GMP-morpholidate (Rf~0.8, U.V.), guanosine 5'-(β-1-fucopyranosyl)-diphosphate (Rf~0.5, U.V. and charring), followed by the tailing spot of the starting fucose-1-phosphate (Rf~0.44, charring). Additional U.V. active minor spots were also present. After stirring for 4 days at room temperature, the yellowish mixture was co-evaporated in vacuo with toluene and the yellowish residue further dried overnight at the vacuum pump leaving a thick residue (2.43 g). Water (10 mL) was then added into the flask to give a yellow cloudy solution which was added on top of a column of AG 50W-X12 (from Biorad) resin (100–200 mesh, 25×1.5 cm, Na$^+$ form). The product eluted with water after the void volume. The fractions which were active, both by U.V. and charring after spotting on a tlc plate, were recovered and the solution freeze-dried overnight in vacuo providing a crude material (1.96 g).

This residue was dissolved in water (10 mL overall) and slowly absorbed onto a column of hydrophobic $C_{18}$ silica gel (Waters, 2.5×30 cm) which had been conditioned by washing with water, methanol and water (250 mL each). Water was then run through the column (0.4 mL/min) and the eluate collected in fractions (0.8 mL) which were checked by tlc (3:5:2 25% aq. ammonium hydroxide, isopropanol and water). β-L-fucopyranosyl-1-phosphate, (Rf~0.54, charring) was eluted in fractions 29 to 45. A product showing a strongly U.V. active spot (Rf~0.51) eluted mainly in fractions 46 to 65. Other minor U.V. active spots of higher or lower Rf were observed. Fractions 59 to 86, which contained guanosine 5'-(β-1-fucopyranosyl)-diphosphate (Rf~0.62), also showed a narrow U.V. active spot (Rf~0.57). Fractions 59 to 86 were pooled and freeze-dried overnight providing 0.353 g of material enriched in guanosine 5'-(β-1-fucopyranosyl)-diphosphate. $^1$H-n.m.r. indicated that this material was contaminated by a small amount of impurities giving signals at δ=4.12 and δ=5.05.

Fractions 29 to 45 and 47 to 57 were separately pooled and freeze-dried providing recovered β-L-fuco-pyranosyl- 1-phosphate (0.264 g and 0.223 g, respectively, in which the second fraction contains some impurities). Occasionally, pooling of appropriate fractions provided some amount of guanosine 5'-(β-1-fucopyranosyl)-diphosphate in good purity ($^1$H-n.m.r.). Generally, all the material enriched in guanosine 5'-(β-1-fuco-pyranosyl)diphosphate was dissolved in a minimum amount of water and run on the same column which had been regenerated by washing with large amounts of methanol followed by water. The fractions containing the purified guanosine 5'-(β-1-fucopyranosyl)-diphosphate (tlc) were pooled and freezed dried in vacuo leaving a white fluffy material (187 mg, 16%). $^1$H-n.m.r. was identical to the previously reported data[53].

PROCEDURE #2

β-L-fucopyranosyl-1-phosphate and guanosine 5'-monophosphomorpholidate (4-morpholine-N,N'-dicyclohexylcarboxamidine salt—"GMP-morpholidate") were reacted in dry pyridine as indicated in the original procedure[55]. Accordingly, the β-L-fucopyranosyl-1-phosphate (triethylammonium salt, 0.528 g, about 1.18 mmol) was dissolved in dry pyridine (20 mL) and the solvent removed in vacuo. The process was repeated three times with care to allow only dry air to enter the flask. GMP-morpholidate (1.2 g, 1.65 mmol) and pyridine (20 mL) were added into the reaction flask, the solvent evaporated in vacuo and the process repeated three times as above. Pyridine (20 mL) was added to the final residue and the heterogeneous mixture was stirred for 3 to 4 days at room temperature under nitrogen. An insoluble mass was formed which had to be occasionally broken down by sonication.

The reaction was followed by tlc and worked up as indicated in the first procedure to provide the GDP-fucose (120 mg, 16%).

II. Biological Results

Examples 26–29 illustrate the immunomodulatory, anti-inflammatory, and tolerogenic properties of compounds disclosed herein.

EXAMPLE 26

Inhibition of DTH Inflammatory Response

DTH inflammatory responses were measured using the mouse footpad swelling assay as described by Smith and Ziola[50]. Briefly, groups of Balb/c mice were immunized with S-layer protein, a bacterial surface protein[51] from *Clostridium thermohydrosulfuricum* L111-69 [L111] or with SuperCarrier (SC) which have been shown to induce a strong inflammatory DTH response. Seven days later, each group of mice was footpad-challenged with 10 μg of L-111 S-Layer protein or with 20 μg of SC. The resulting inflammatory footpad swelling was measured with a Mitutoyo Engineering micrometer 24 hours after challenge.

To assess the effect on the DTH inflammatory response by sialyl Lewis$^x$-OR and sulfated Lewis$^x$-OR (compound 47), groups of mice challenged with 10 μg of the same antigen 7 days after immunization with the antigen received 100 μg of sialyl Lewis$^x$-OR or sulfated Lewis$^x$-OR [R=—(CH$_2$)$_8$COOCH$_3$] injected into the tail vein, 5 hours after challenge. Control groups were left untreated. The results of this experiment are shown in FIG. 11 which demonstrates that while mice injected with either sialyl Lewis$^x$-OR or sulfated Lewis$^x$-OR exhibited reduced inflammation, those injected with sialyl Lewis$^x$ exhibited the greater reduction in inflammation.

To assess the effect on the DTH inflammatory response by the modified Lewis$^x$-OR compound containing a sulfate substituent at the 3-position of galactose (compound 47), groups of mice challenged with either 10 μg of the L111 antigen (FIG. 11) or with 20 μg of the SC antigen (FIG. 12) 7 days after immunization with the antigen received 100 μg of sialyl Lewis$^x$ or sulfated Lewis$^x$ injected into the tail vein, 5 hours after challenge. Control groups were left untreated or received 100 μL of phosphate-buffered saline (PBS). The results of this part of this example are set forth in FIG. 12 which illustrates that the sulfated Lewis$^x$ provided roughly equivalent reduction in inflammation. This result is particularly surprising when compared to FIG. 11 and demonstrates that substitution of the sulfate group at the 3-position of the galactose of Lewis$^x$ significantly enhances the anti-inflammatory properties of these compounds.

EXAMPLE 27

Effect of Oligosaccharide Glycosides on LPS Caused Lung Injury

LPS (lipopolysaccharide) caused lung injury is measured by weighing the lungs of sacrificed mice 24 hours after mice are given LPS intranasally. Briefly, groups of 8–10 week old Balb/c mice were sensitized with 5 μg/mouse of LPS in 50 μl of PBS intranasally under light anesthesia.

The method of administering compound intranasally is described in Smith et al., Infection and Immunity, 31: 129 (1980), which is incorporated by reference. Briefly, mice are anethesitized with Metofane (Pitman-Moore Ltd., Mississauga, Ontario, Canada) and a 50 μl drop of compound is placed on the nares of the mouse and is inhaled.

Five hours later, 100 μg/mouse of sialyl Lewis$^x$ or sulfated Lewis$^x$ in 200 μl of PBS are given to the mouse intravenously. After 24 hours, the mice are sacrificed and the lungs removed and weighed. The weight of the lungs of mice treated with either sialyl Lewis$^x$ or sulfated Lewis$^x$ are compared against control (i.e., mice treated with LPS but to which neither sialyl Lewis$^x$ or Lewis$^x$ has been administered). The percent reduction is measured by subtracting from 100 the following:

The fraction derived by a numerator whose value is the weight of the treated lungs subtracted from the weight of normal lungs (lungs from mice not exposed to LPS, sialyl Lewis$^x$ or sulfated Lewis$^x$), and whose denominator whose value is the weight of the control lungs (mice that received only LPS) subtracted from the weight of normal lungs and multiplying the resulting fraction by 100.

The greater the percent reduction, the better the compound is in alleviating lung damage.

The results of this test are set forth in FIG. 13 which illustrates that sulfated Lewis$^x$ provides about 50% reduction whereas sialyl Lewis$^a$ provides only about a 30% reduction in the DTH inflammatory response in lungs. This suggests that sialyl Lewis$^x$ and sulfated Lewis$^x$ can be useful in reducing inflamation in lungs exposed to antigen, for example Acute Respiratory Distress Syndrome and that sulfated Lewis$^x$ actually provides significantly enhanced results.

EXAMPLE 28

Effect of Administration of Sialyl Lewis$^x$ and Sulfated Lewis$^x$ at the Time of Immunization on the Induction of an Immune Response to an Antigen Groups of Balb/c female mice were immunized with 20 μg/mouse SC in 100 μl of PBS intramuscularly into the hind leg muscle which formulation also contained 100 μg/mouse of sialyl Lewis$^x$ or sulfated Lewis$^x$. Seven day later the mice were footpad challenged with 20 μg/mouse of SC in 20 μL of PBS. Control groups were either not immunized or received 20 μL of phosphate-buffered saline (PBS) in place of either sialyl Lewis$^x$ or sulfated Lewis$^x$. The footpad swelling was measured 24 hours later with a Mitutoyo Engineering micrometer.

FIG. 14 shows that administering sialyl Lewis$^x$ or sulfated Lewis$^x$ to the mice at the time of immunization reduces the induction of an immune response to an antigen as compared to PBS control. This suggests that administration of a compound of this invention at the time of antigen immunization will reduce the ability of the mammal to become educated concerning this antigen.

EXAMPLE 29

Persistence of Suppression of the DTH Inflammatory Response at 6 Weeks After Challenge i. The identical groups of mice treated with sialyl Lewis$^x$ and sulfated Lewis$^x$ in Example 26 were re-challenged 6 weeks after primary immmunization with 20 μg/mouse with SC. Untreated controls responded with the usual degree of footpad swelling whereas all other groups showed reduced footpad swelling as shown in FIG. 15.

In addition to providing an anti-inflammatory effect as well as modulation of a cell-mediated immune response, the above data demonstrate that treatment with sulfated Lewis$^x$ as per this invention also imparts tolerance to additional challenges from the same antigen.

Additionally, other compounds disclosed herein can be used in place of the sulfated Lewis$^x$ including the following galactose substituted materials: 6-sulfated Lewis$^x$, 3- or 6-sulfated Lewis$^a$, 3- or 6-phosphated Lewis$^x$, 3-6-phosphated Lewis$^a$, and the following fucosed substituted materials: 3- or 4- sulfated or phosphated fucose groups on Lewis$^x$ or Lewis$^a$ and the like.

What is claimed is:

1. A compound of the formula:

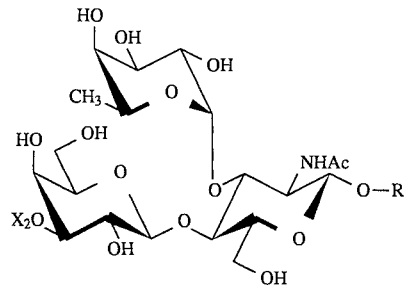

where

R is an aglycon of from 1 to 10 carbon atoms; and $X_2$ is selected from sulfate and phosphate and pharmaceutical salts thereof.

2. The compound according to claim 1 wherein $X_2$ is sulfate.

3. The compound according to claim 1 wherein $X_2$ is phosphate.

4. The compound according to claim 2 wherein R is —(CH$_2$)$_8$COOCH$_3$.

5. The compound according to claim 3 wherein R is —(CH$_2$)$_8$COOCH$_3$.

6. A pharmaceutical composition suitable for administration to a mammal which composition comprises a pharmaceutically inert carrier and a sufficient amount of a compound of claim 1 so as to provide a dosage range of from about 0.5 mg to about 50 mg/kg of body weight when administered to said mammal.

7. The pharmaceutical composition according to claim 6 wherein $X_2$ is sulfate.

8. The pharmaceutical composition according to claim 6 wherein $X_2$ is phosphate.

9. The pharmaceutical composition according to claim 7 wherein R is —(CH$_2$)$_8$COOCH$_3$.

10. The pharmaceutical composition according to claim 8 wherein R is —(CH$_2$)$_8$COOCH$_3$.

\* \* \* \* \*